(12) United States Patent
Lee et al.

(10) Patent No.: US 9,882,145 B2
(45) Date of Patent: Jan. 30, 2018

(54) HETERO RING COMPOUND AND ORGANIC LIGHT EMITTING DIODE COMPRISING SAME

(71) Applicant: LG Chem, Ltd., Seoul (KR)

(72) Inventors: Sangbin Lee, Daejeon (KR); Dong Uk Heo, Daejeon (KR); Jungi Jang, Daejeon (KR); Seong So Kim, Daejeon (KR); Dong Hoon Lee, Daejeon (KR); Boonjae Jang, Daejeon (KR); Minyoung Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/898,363

(22) PCT Filed: Nov. 7, 2013

(86) PCT No.: PCT/KR2013/010079
§ 371 (c)(1),
(2) Date: Dec. 14, 2015

(87) PCT Pub. No.: WO2014/208829
PCT Pub. Date: Dec. 31, 2014

(65) Prior Publication Data
US 2016/0141514 A1    May 19, 2016

(30) Foreign Application Priority Data
Jun. 28, 2013   (KR) .................. 10-2013-0075662

(51) Int. Cl.
*H01L 51/00*     (2006.01)
*C07D 251/24*    (2006.01)
(Continued)

(52) U.S. Cl.
CPC ........ *H01L 51/0067* (2013.01); *C07D 251/24* (2013.01); *C07D 401/10* (2013.01);
(Continued)

(58) Field of Classification Search
None
See application file for complete search history.

(56) References Cited

U.S. PATENT DOCUMENTS 6,057,048 A * 5/2000 Hu ..................... C07D 251/24
                                                    313/504
9,199,966 B2  12/2015 Kim et al.
(Continued)

FOREIGN PATENT DOCUMENTS

CN     102532000 A    7/2012
CN     102593374 A    7/2012
(Continued)

OTHER PUBLICATIONS

International Search Report from PCT/KR2013/010079, dated Mar. 19, 2014.
(Continued)

*Primary Examiner* — J. L. Yang
(74) *Attorney, Agent, or Firm* — Dentons US LLP

(57) ABSTRACT

The present specification provides a novel compound greatly improving the life span, efficiency, electrical and chemical stability and thermal stability of an organic light emitting device, and an organic light emitting device containing the compound in an organic compound layer.

14 Claims, 1 Drawing Sheet

(51) Int. Cl.
*C07D 403/10* (2006.01)
*C09K 11/06* (2006.01)
*C07D 401/10* (2006.01)
*C09K 11/02* (2006.01)
*H01L 51/50* (2006.01)

(52) U.S. Cl.
CPC .......... *C07D 403/10* (2013.01); *C09K 11/025* (2013.01); *C09K 11/06* (2013.01); *H01L 51/0052* (2013.01); *H01L 51/0058* (2013.01); *H01L 51/0072* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 9,406,891 | B2 | 8/2016 | Jung et al. |
| 9,614,161 | B2 | 4/2017 | Park et al. |
| 2007/0190355 | A1 | 8/2007 | Ikeda et al. |
| 2008/0111473 | A1 | 5/2008 | Kawamura et al. |
| 2009/0174312 | A1 | 7/2009 | Kim et al. |
| 2011/0156014 | A1 | 6/2011 | Kim et al. |
| 2011/0240983 | A1 | 10/2011 | Sekiguchi et al. |
| 2012/0104941 | A1 | 5/2012 | Jung et al. |
| 2012/0273771 | A1 | 11/2012 | Jung et al. |
| 2012/0280613 | A1 | 11/2012 | Kang et al. |
| 2012/0286249 | A1 | 11/2012 | Lee et al. |
| 2013/0153863 | A1 | 6/2013 | Wong et al. |
| 2014/0158999 | A1* | 6/2014 | Jung ................ C09K 11/06 257/40 |
| 2014/0203272 | A1* | 7/2014 | Hong ............... H01L 51/0052 257/40 |
| 2014/0367654 | A1* | 12/2014 | Kim ................. H01L 51/0052 257/40 |
| 2015/0340620 | A1 | 11/2015 | Park et al. |
| 2016/0141514 | A1 | 5/2016 | Lee et al. |
| 2017/0012221 | A1 | 1/2017 | Buesing et al. |

FOREIGN PATENT DOCUMENTS

| | | |
|---|---|---|
| JP | 2010138121 A | 6/2010 |
| JP | 2012-501091 A | 1/2012 |
| JP | 2012-028524 A | 2/2012 |
| JP | 2012-513987 A | 6/2012 |
| JP | 2013-518069 A | 5/2013 |
| JP | 2014-118410 A | 6/2014 |
| KR | 10-2007-0088728 A | 8/2007 |
| KR | 10-2008-0016007 A | 2/2008 |
| KR | 10-2011-0079197 A | 7/2011 |
| KR | 10-2011-0111093 A | 10/2011 |
| KR | 10-2012-0127683 A | 11/2012 |
| KR | 20130060157 A | 6/2013 |
| KR | 10-2013-0134471 A | 12/2013 |
| TW | 201402565 A | 1/2014 |
| WO | 2007105884 A1 | 9/2004 |
| WO | WO-2013/129835 A1 * | 9/2013 |

OTHER PUBLICATIONS

Written Opinion of the ISA from PCT/KR2013/010079, dated Mar. 19, 2014 and Jul. 21, 2015.
Written Opinion of the ISA from PCT/KR2014/005670, dated Oct. 31, 2014 and Jul. 21, 2015.
Office Action of Korean Patent Office in Appl'n. No. 10-2013-0134471, dated Jan. 15, 2015; and Sep. 18, 2014.
Office Action of Korean Patent Office in Appl'n No. 10-2014-0078411, dated May 21, 2015; and Nov. 21, 2014.
Office Action of Taiwanese Patent Office in Appl'n No. 102140663, dated Sep. 25, 2014.
Office Action of Taiwnese Patent Office in Appl'n No. 103122044, dated Apr. 14, 2015.

* cited by examiner

【FIG. 1】
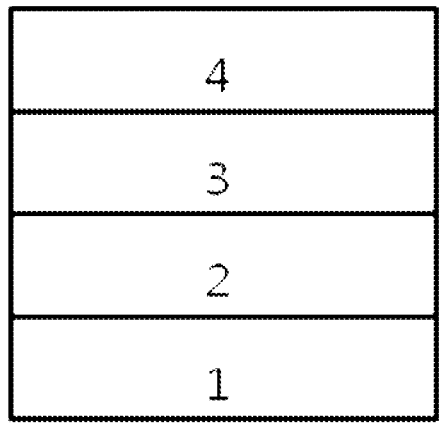
【FIG. 2】
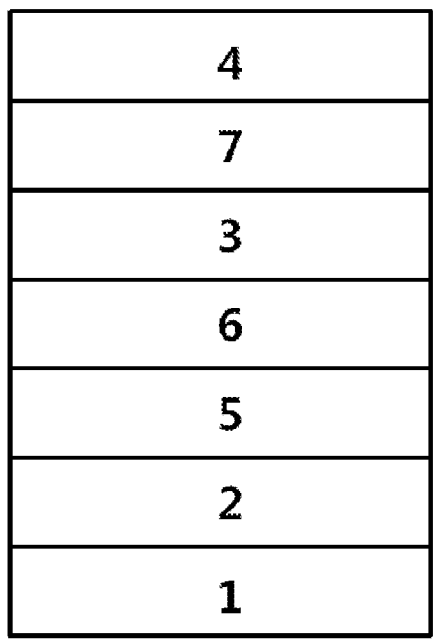

HETERO RING COMPOUND AND ORGANIC LIGHT EMITTING DIODE COMPRISING SAME

FIELD OF THE INVENTION

The present specification relates to a novel hetero-cyclic compound and an organic light emitting device comprising the same.

This application is a National Stage Entry of International Application No. PCT/KR2013/010079, filed Nov. 7, 2013, and claims the benefit of Korean Application No. 10-2013-0075662, filed on Jun. 28, 2013, all of which are hereby incorporated by reference in their entirety for all purposes as if fully set forth herein.

BACKGROUND OF THE INVENTION

An organic light emission phenomenon generally refers to a phenomenon that converts electric energy to light energy using an organic material. An organic light emitting device using an organic light emission phenomenon typically has a structure that includes an anode; a cathode, and an organic material layer therebetween. Herein, the organic material layer is usually formed as a multilayer structure formed with different materials in order to improve the efficiency and the stability of an organic light emitting device, and for example, may be formed with a hole injection layer, a hole transfer layer, a light emitting layer, an electron transfer layer, an electron injection layer, and the like. In the structure of such an organic light emitting device, holes from the anode and electrons from the cathode flow into the organic material layer when voltage is applied between the two electrodes, excitons form when the electrons and the holes injected are recombined, and light emits when these excitons fall back to the ground state.

There have been continuous demands for the development of new materials that can be used in organic light emitting devices such as above.

SUMMARY OF THE INVENTION

In view of the above, an objective of the present application is to provide a hetero-cyclic compound having a chemical structure that can perform various roles required in an organic light emitting device depending on substituents, and to provide an organic light emitting device including the hetero-cyclic compound.

In one embodiment of the present specification, a compound represented by the following Chemical Formula 1 is provided.

[Chemical Formula 1]

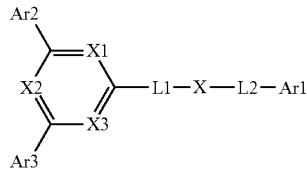

In Chemical Formula 1,
X is any one of the following structural formulae,

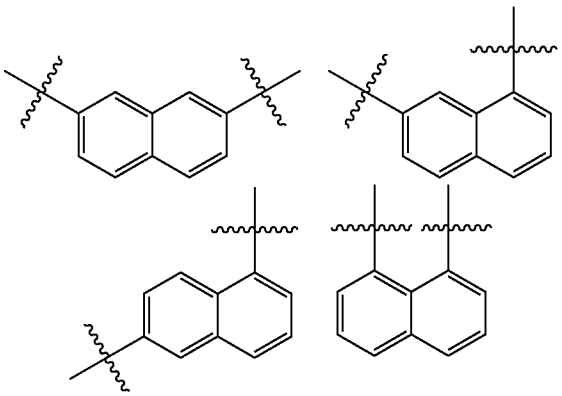

L1 and L2 are the same as or different from each other, each independently directly bonded; a substituted or unsubstituted arylene group; or a substituted or unsubstituted alkenylene group, Ar1 is a substituted or unsubstituted aryl, group; or a substituted or unsubstituted heteroring group including one or more of O, N and S as a heteroatom, L1 and L2 are different from each other, or

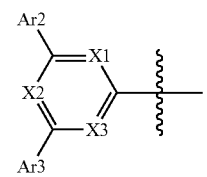

and Ar1 are different from each other,

X1 to X3 are the same as or different from each other, each independently a trivalent heteroatom or CH, and at least one of X1 to X3 is a trivalent heteroatom, Ar2 and Ar3 are the same as or different from each other, each independently a substituted or unsubstituted aryl group, or a substituted or unsubstituted heteroring group including one or more of O, N and S as a heteroatom.

In addition, in one embodiment of the present specification, an organic light emitting device that includes a first electrode; a second electrode provided opposite to the first electrode; and one or more layers of organic material layers provided between the first electrode and the second electrode, wherein one or more layers of the organic material layers include the hetero-cyclic compound represented by Chemical Formula 1.

Advantageous Effects

A novel compound according to the present specification can be used as the material of an organic material layer of an organic light emitting device, and by using the compound, an improvement of efficiency, a low driving voltage and/or an improvement of life span characteristics are possible.

BRIEF DESCRIPTION OF THE DRAWINGS

FIG. 1 shows an example of an organic electronic device in which a substrate (1), an anode (2), a light emitting layer (3) and a cathode (4) are laminated in consecutive order by a diagram.

FIG. 2 shows an example of an organic electronic device in which a substrate (1), an anode (2), a hole injection layer (5), a hole transfer layer (6), a light emitting layer (3), an electron transfer layer (7) and a cathode (4) are laminated in consecutive order by a diagram.

DETAILED DESCRIPTION OF THE EMBODIMENTS

The present specification provides a compound represented by Chemical Formula 1.

In the present specification,

means a site linking to other substituents.

In one embodiment of the present specification, in Chemical Formula 1, L1 and L2 are different from each other, or

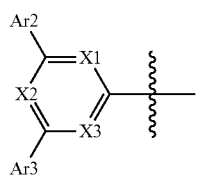

and Ar1 are different from each other.

Specifically, in one embodiment of the present specification, L1 and L2, and Ar1 and

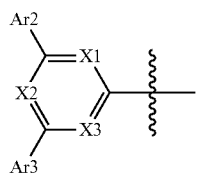

may be different from each other. In another embodiment, L1 and L2 different from each other, and Ar1 and

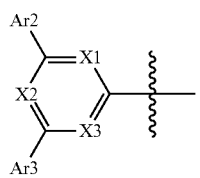

may be the same as each other. In another embodiment, L1 and L2 the same as each other, and Ar1 and

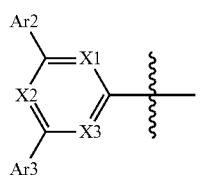

may be different from each other.

In one embodiment of the present specification, L1 and L2 are different from each other, each independently directly bonded; or a substituted or unsubstituted phenylene group.

In one embodiment of the present specification, L1 is directly bonded, and L2 is a substituted or unsubstituted phenylene group.

In one embodiment of the present specification, L1 is a substituted or unsubstituted phenylene group, and L2 is directly bonded.

In one embodiment of the present specification, L1 and L2 are substituted or unsubstituted phenylene groups, and each phenylene group has different substituents or has different bonding sites.

In one embodiment of the present specification, Ar1 and

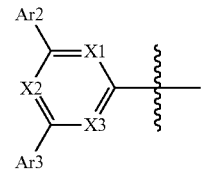

are different from each other, and Ar1 is represented by the following Chemical Formula 2.

[Chemical Formula 2]

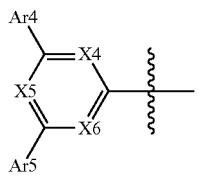

In Chemical Formula 2,

X4 to X6 are the same as or different from each other, each independently a trivalent heteroatom or CH, and at least one of X1 to X3 is a trivalent heteroatom, Ar4 and Ar5 are the same as or different from each other, each independently a substituted or unsubstituted aryl group or a substituted or unsubstituted heteroring group including one or more of O, N and S as a heteroatom.

In one embodiment of the present specification, Ar1 and

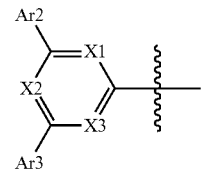

being different means that at least one of X1, X2, X3, Ar2 and Ar3 may be different from X4, X5, X6, Ar4 and Ar5.

In one embodiment of the present specification, Ar1 is represented by any one of the following Chemical Formula 3 to Chemical Formula 10.

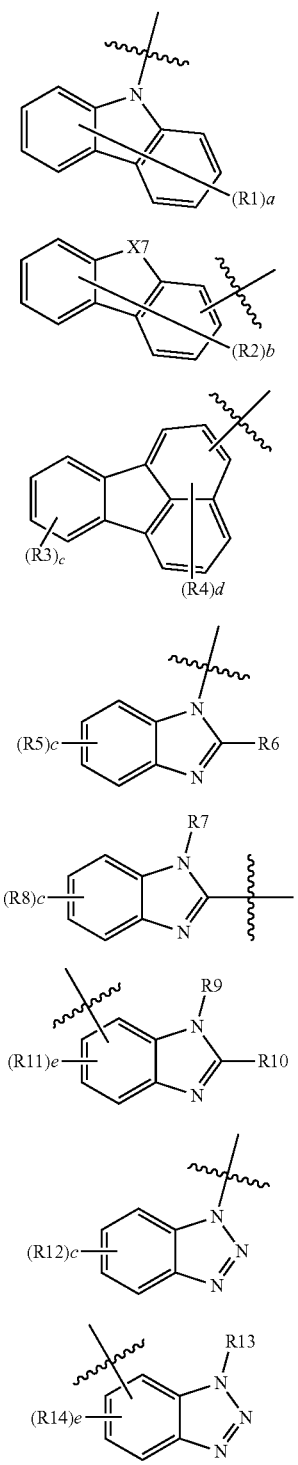

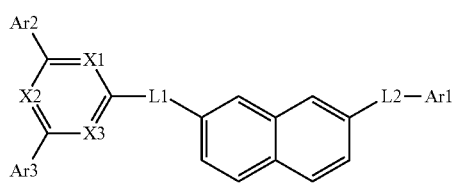

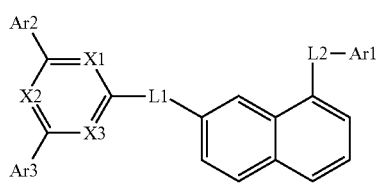

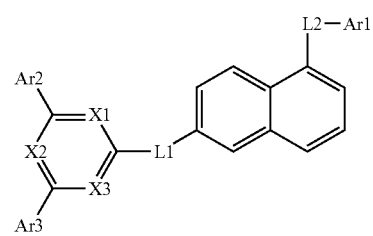

In Chemical Formulae 3 to 10,
a is an integer of 0 to 8,
b is an integer of 0 to 7,
c is an integer of 0 to 4,
d is an integer of 0 to 5,
e is an integer of 0 to 3,
X7 is S, O, NR or CRR', and
R, R' and R1 to R14 are the same as or different from each other, each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxide group; a substituted or unsubstituted arylsulfoxide group; a substituted or unsubstituted alkenyl group; a substituted or unsubstituted silyl group; a substituted or unsubstituted boron group; a substituted or unsubstituted amine group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heteroring group including one or more of O, N and S as a heteroatom.

In one embodiment of the present specification, positions 2 and 7 of the naphthylene of Chemical Formula 1 are substituted with L1 and L2, respectively.

In one embodiment of the present specification, positions 1 and 7 of the naphthylene of Chemical Formula 1 are substituted with L1 and L2, respectively.

In one embodiment of the present specification, positions 1 and 6 of the naphthylene of Chemical Formula 1 are substituted with L1 and L2, respectively.

In one embodiment of the present specification, positions 1 and 8 of the naphthylene of Chemical Formula 1 are substituted with L1 and L2, respectively.

In one embodiment of the present specification, the hetero-cyclic compound represented by Chemical Formula 1 is represented by any one of the following Chemical Formulae 1-1 to 1-4.

[Chemical Formula 1-4]

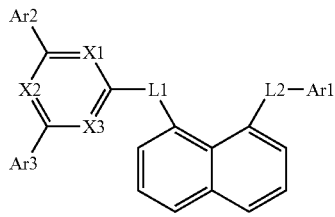

In Chemical Formulae 1-1 to 1-4, Ar1, Ar2, Ar3, X1 to X3, and L1 and L2 are the same as those defined above.

Examples of the substituents are described below, but are not limited thereto.

In the present specification, the term "substituted or unsubstituted" means being substituted with one or more substituents selected from the group consisting of deuterium; a halogen group; a nitrile group; a nitro group; an imide group; an amide group; a hydroxy group; a thiol group; an alkyl group; an alkenyl group; an alkoxy group; a cycloalkyl group; a silyl group; an arylalkenyl group; an aryloxy group; an alkylthioxy group; an arylthioxy group; an alkylsulfoxide group; an arylsulfoxide group; a silyl group; a boron group; an alkylamine group; an aralkylamine group; an arylamine group; an aryl group; an arylalkyl group; an arylalkenyl group; and a heteroring group including one or more of O, N and S as a heteroatom, or means having no substituents.

In the present specification, examples of the halogen group include fluorine, chlorine, bromine and iodine.

In the present specification, the number of carbon atoms of the imide group is not particularly limited, but is preferably 1 to 25. Specifically, compounds having the following structures may be included, but the compound is not limited thereto.

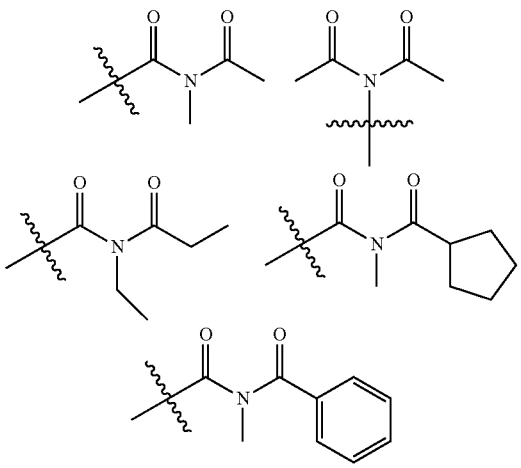

In the present specification, in the amide group, the nitrogen of an amide group may be once or twice substituted with hydrogen, a linear, branched or ring-chained alkyl group having 1 to 25 carbon atoms, or an aryl groups having 6 to 25 carbon atoms. Specifically, compounds having the following structures may be included, but the compound is not limited thereto.

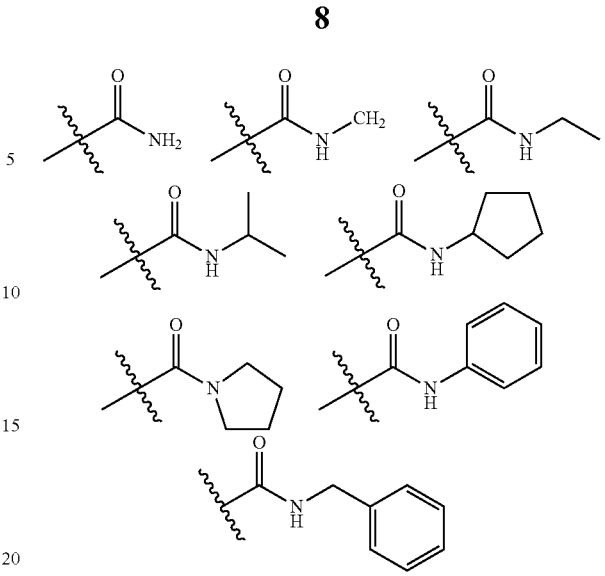

In the present specification, the alkyl group may be linear or branched, the number of carbon atoms is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl or the like, but are not limited thereto.

In the present specification, the cycloalkyl group is not particularly limited, but preferably has 3 to 60 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl or the like, but are not limited thereto.

In the present specification, the alkoxy group may be linear, branched or have a ring chain. The number of carbon atoms of the alkoxy group is not particularly limited, but is preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy or the like, but are not limited thereto.

In the present specification, the alkenyl group may be linear or branched, and although not particularly limited, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group or the like, but are not limited thereto.

In the present specification, the aryl group may be a monocyclic aryl group or a multicyclic aryl group, and includes a case in which an alkyl group having 1 to 25 carbon atoms or an alkoxy group having 1 to 25 carbon atoms is substituted. In addition, the aryl group in the present specification may mean an aromatic ring.

When the aryl group is a monocyclic aryl group, although not particularly limited, the number of carbon atoms is preferably 6 to 25. Specifically, a phenyl group, a biphenyl group, a terphenyl group, a stilbenyl group or the like may be included as the monocyclic aryl group, but the monocyclic aryl group is not limited thereto.

When the aryl group is a multicyclic aryl group, although not particularly limited, the number of carbon atoms is preferably 10 to 24. Specifically, a naphthyl group, an anthracenyl group, a phenanthryl group, a pyrenyl group, a perylenyl group, a crycenyl group, a fluorenyl group or the like may be included as the multicyclic aryl group, but the multicyclic aryl compound is not limited thereto.

In the present specification, the fluorenyl group has a structure in which two cyclic organic compounds are linked through one atom.

The fluorenyl group includes the structure of an open fluorenyl group, and herein, the open fluorenyl group has a structure in which the linkage of one cyclic organic compound is broken in the structure of two cyclic compounds linked through one atom.

When the fluorenyl group is substituted, it may become

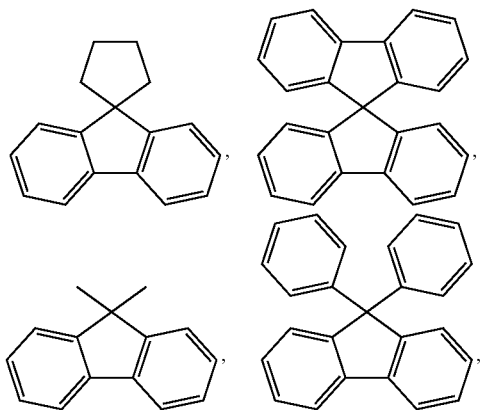

and the like. However, the examples are not limited thereto.

In the present specification, the silyl group specifically includes a trimethyl silyl group, a triethyl silyl group, a t-butyldimethyl silyl group, a vinyldimethyl silyl group, a propyldimethyl silyl group, a triphenyl silyl group, a diphenyl silyl group, a phenyl silyl group or the like, but is not limited thereto.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group or the like, but are not limited thereto.

In the present specification, the number of carbon atoms of the amine group is not particularly limited, but is preferably 1 to 50. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group or the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include a monocyclic aryl group, a multicyclic aryl group, or a monocyclic aryl group and a multicyclic aryl group at the same time.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, a carbazol and a triphenylamine group or the like, but are not limited thereto.

In the present specification, the heteroaryl group in the heteroarylamine group may be selected from among the examples of the heteroring group described above.

In the present specification, the heteroring group is a heteroring group including one or more of O, N and S as a heteroatom, and although not particularly limited, the number of carbon atoms is preferably 2 to 60. Examples of the heteroring group includes a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group or the like, but are not limited thereto.

In the present specification, the aryl group in the aryloxy group, the arylthioxy group, the arylsulfoxide group and the aralkylamine group is the same as the aryl group examples described above. Specific examples of the aryloxy group include phenoxy, p-tolyloxy, m-tolyloxy, 3,5-dimethyl-phenoxy, 2,4,6-trimethylphenoxy, p-tert-butylphonoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy or the like, and examples of the arylthioxy group include a phenylthioxy group, a 2-methylphenylthioxy group, a 4-tert-butylphenylthioxy group or the like, and examples of the arylsulfoxide group include a benzene sulfoxide group, p-toluene sulfoxide group or the like, but are not limited thereto.

In the present specification, the alkyl group in the alkylthioxy group and the alkylsulfoxide group is the same as the alkyl group examples described above. Specific examples of the alkylthioxy group include a methylthioxy group, an ethylthioxy group, a tert-butylthioxy group, a hexylthioxy group, an octylthioxy group or the like, and examples of the alkylsulfoxide group include a mesyl group, an ethyl sulfoxide group, a propyl sulfoxide group, a butyl sulfoxide group or the like, but are not limited thereto.

In the present specification, the arylene group and the alkenylene group mean having two binding sites in the aryl group and the alkenyl group, respectively, which mean a divalent group. Descriptions for the aryl group and the alkenyl group may be applied respectively, except that the arylene group and the alkenylene group are divalent groups.

In the present specification, the heteroatom of trivalent group includes N or P, but is not limited thereto.

In one embodiment of the present specification, the heteroatom of trivalent group is N.

In one embodiment of the present specification, X1 to X3 are the same as or different from each other, each independently N or CH, and at least one of X1 to X3 is N.

In one embodiment of the present specification, Ar2 and Ar3 are the same as or different from each other, each independently a substituted or unsubstituted phenyl group; a substituted or unsubstituted biphenyl group; or a substituted or unsubstituted naphthyl group.

In one embodiment of the present specification, L1 is a substituted or unsubstituted arylene group.

In one embodiment of the present specification, L1 is a substituted or unsubstituted phenylene group.

In one embodiment of the present specification, L1 is a phenylene group.

In one embodiment of the present specification, L1 is a phenylene group, and the phenylene group is

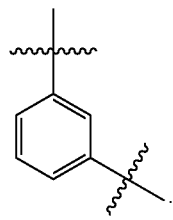 [SMILES: *c1cccc(*)c1]

In another embodiment, L1 is a phenylene group, and the phenylene group is

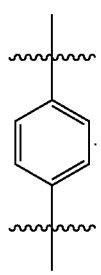

The

means being linked to

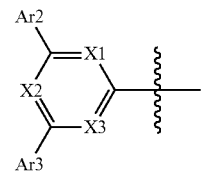

or to a naphthyl group in Chemical Formula 1.

In one embodiment of the present specification, L2 is a substituted or unsubstituted arylene group.

In one embodiment of the present specification, L2 is a substituted or unsubstituted phenylene group.

In one embodiment of the present specification, L2 is a phenylene group.

In one embodiment of the present specification, L2 is a phenylene group, and the phenylene group is

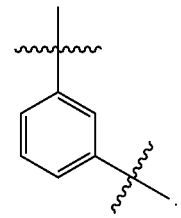 [SMILES: *c1cccc(*)c1]

In another embodiment, L2 is a phenylene group, and the phenylene group is

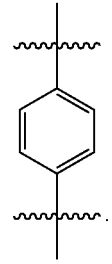 [SMILES: *c1ccc(*)cc1]

The

means being linked to Ar1 or a naphthyl group in Chemical Formula 1.

In one embodiment, at least any one of X1 to X3 in Chemical Formula 1 may be a heteroatom of trivalent group.

Specifically, at least any one of X1 to X3 may be N or P.

In one embodiment of the present specification, all of X1 to X3 may be N.

In one embodiment of the present specification, X1 may be N, and X2 and X3 may be CH.

In one embodiment of the present specification, X2 may be N, and X1 and X3 may be CH.

In one embodiment of the present specification, X3 may be N, and X1 and X2 may be CH.

In one embodiment of the present specification, X1 and X2 may be N. In this case, X3 is CH.

In one embodiment of the present specification, X1 and X3 may be N. In this case, X2 is CH.

In one embodiment of the present specification, X2 and X3 may be N. In this case, X1 is CH.

In one embodiment of the present specification, Ar2 and Ar3 in Chemical Formula 1 are the same as or different from each other, and each independently a substituted or unsubstituted aryl group.

In one embodiment of the present specification, Ar2 is a phenyl group.

In one embodiment of the present specification, Ar2 is a naphthyl group.

In one embodiment of the present specification, Ar2 is a naphthyl group, and may be

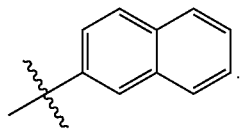 [SMILES: *c1ccc2ccccc2c1]

In another embodiment, Ar2 is a naphthyl group, and may be

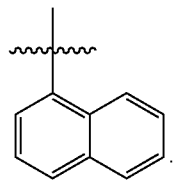

In one embodiment of the present specification, Ar2 is a biphenyl group.

In one embodiment of the present specification, Ar2 is a biphenyl group, and may be

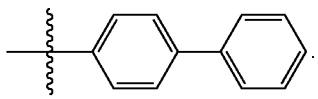

In one embodiment of the present specification, Ar3 is a phenyl group.

In one embodiment of the present specification, Ar3 is a naphthyl group.

In one embodiment of the present specification, Ar3 is a naphthyl group, and may be

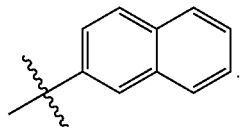 [SMILES: *c1ccc2ccccc2c1]

In another embodiment, Ar3 is a naphthyl group, and may be

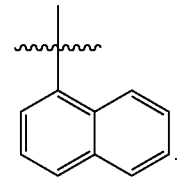

In one embodiment of the present specification, Ar3 is a biphenyl group.

In one embodiment of the present specification, Ar3 is a biphenyl group, and may be

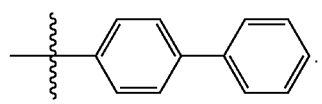 [SMILES: *c1ccc(-c2ccccc2)cc1]

The

means being linked to heterocyclic ring including X1 to X3 of Chemical Formula 1.

In one embodiment of the present specification, Ar4 and Ar5 in Chemical Formula 2 are the same as or different from each other, and each independently a substituted or unsubstituted aryl group.

In one embodiment of the present specification, Ar4 and Ar5 in Chemical Formula 2 are the same as or different from each other, and each independently a substituted or unsubstituted phenyl group; a substituted or unsubstituted biphenyl group; or a substituted or unsubstituted naphthyl group.

In one embodiment of the present specification, Ar4 is a phenyl group.

In one embodiment of the present specification, Ar4 is a naphthyl group.

In one embodiment of the present specification, Ar4 is a naphthyl group, and may be

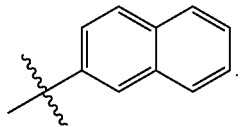 [SMILES: *c1ccc2ccccc2c1]

In another embodiment, Ar4 is a naphthyl group, and may be

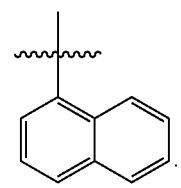

In one embodiment of the present specification, Ar4 is a biphenyl group.

In one embodiment of the present specification, Ar4 is a biphenyl group, and may be

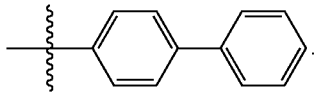

In one embodiment of the present specification, Ar5 is a phenyl group.

In one embodiment of the present specification, Ar5 is a naphthyl group.

In one embodiment of the present specification, Ar5 is a naphthyl group, and may be

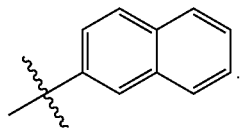 [SMILES: *c1ccc2ccccc2c1]

In another embodiment, Ar5 is a naphthyl group, and may be

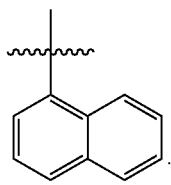 [SMILES: *c1cccc2ccccc12]

In one embodiment of the present specification, Ar5 is a biphenyl group.

In one embodiment of the present specification, Ar5 is a biphenyl group, and may be

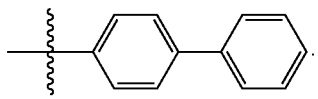

The

means being linked to heterocyclic ring including X4 to X6 of Chemical Formula 2.

In one embodiment of the present specification, Ar1 is Chemical Formula 2.

In one embodiment of the present specification, Ar1 is Chemical Formula 2, and X4 to X6 are N.

In one embodiment of the present specification, Ar1 is Chemical Formula 2, X4 to X6 are N, Ar4 and Ar5 are the same as or different from each other, and each independently a substituted or unsubstituted aryl group.

In one embodiment of the present specification, Ar1 is Chemical Formula 2, X4 to X6 are N, Ar4 and Ar5 are the same as or different from each other, and each independently a substituted or unsubstituted phenyl group.

In one embodiment of the present specification, Ar1 is Chemical Formula 2, X4 to X6 are N, and Ar4 and Ar5 are phenyl groups.

In one embodiment of the present specification, Ar1 is Chemical Formula 2, X4 to X6 are N, Ar4 and Ar5 are the same as or different from each other, and each independently a phenyl group or a naphthyl group.

In one embodiment of the present specification, Ar1 is Chemical Formula 2, X4 to X6 are N, Ar4 and Ar5 are the same as or different from each other, and each independently a phenyl group or a biphenyl group.

In one embodiment of the present specification, Ar1 is Chemical Formula 2, X5 is CH, and X4 and X6 are N.

In one embodiment of the present specification, Ar1 is Chemical Formula 2, X4 is CH, and X5 and X6 are N.

In one embodiment of the present specification, Ar1 is Chemical Formula 3.

In one embodiment of the present specification, Ar1 is Chemical Formula 3, R1 is hydrogen.

In one embodiment of the present specification, Ar1 is Chemical Formula 4.

In one embodiment of the present specification, Ar1 is Chemical Formula 4, L1 and Chemical Formula 4 are bonded at position 2 of Chemical Formula 4.

In one embodiment of the present specification, Ar1 is Chemical Formula 4, and X4 is CRR'.

In one embodiment of the present specification, Ar1 is Chemical Formula 4, X4 is CRR', and R and R' are each independently a substituted or unsubstituted alkyl group.

In one embodiment of the present specification, Ar1 is Chemical Formula 4, X4 is CRR', R and R' are methyl groups, and R2 is hydrogen.

In one embodiment of the present specification, Ar1 is Chemical Formula 5.

In one embodiment of the present specification, Ar1 is Chemical Formula 5, L1 and Chemical Formula 5 are bonded at position 3 of Chemical Formula 5.

In one embodiment of the present specification, Ar1 is Chemical Formula 5, and R3 and R4 are hydrogen.

In one embodiment of the present specification, Ar1 is Chemical Formula 6.

In one embodiment of the present specification, Ar1 is Chemical Formula 6, and R6 is hydrogen.

In one embodiment of the present specification, R5 is hydrogen.

In one embodiment of the present specification, Ar1 is Chemical Formula 7.

In one embodiment of the present specification, Ar1 is Chemical Formula 7, and R7 is a substituted or unsubstituted aryl group.

In one embodiment of the present specification, R7 is a substituted or unsubstituted phenyl group.

In one embodiment of the present specification, R7 is a phenyl group.

In one embodiment of the present, specification, R8 is hydrogen.

In another embodiment, Ar1 is Chemical Formula 8.

In one embodiment of the present specification, Ar1 is Chemical Formula 8, R9 is a substituted or unsubstituted aryl group.

In another embodiment, R9 is a substituted or unsubstituted phenyl group.

In one embodiment of the present specification, R9 is a phenyl group.

In one embodiment of the present specification, R10 is hydrogen.

In one embodiment of the present specification, R11 is hydrogen.

In one embodiment of the present specification, Ar1 is Chemical Formula 9.

In another embodiment, Ar1 is Chemical Formula 9, and R12 is hydrogen.

In one embodiment of the present specification, the compound represented by Chemical Formula 1 is represented by any one of the following Chemical Formulae 1-a-1 to 1-a-14, 2-a-1 to 2-a-14, 3-a-1 to 3-a-14, and 4-a-1 to 4-a-14.

In one embodiment of the present specification, the compound represented by Chemical Formula 1 is represented by any one of the following Chemical Formulae 1-b-1 to 1-b-26, 2-b-1 to 2-b-26, 3-b-1 to 3-b-26, and 4-b-1 to 4-b-26.

In one embodiment of the present specification, the compound represented by Chemical Formula 1-1 is represented by any one of the following Chemical Formulae 1-a-1 to 3-a-14, and 1-b-1 to 1-b-26.

Chemical Formula 1-a-1

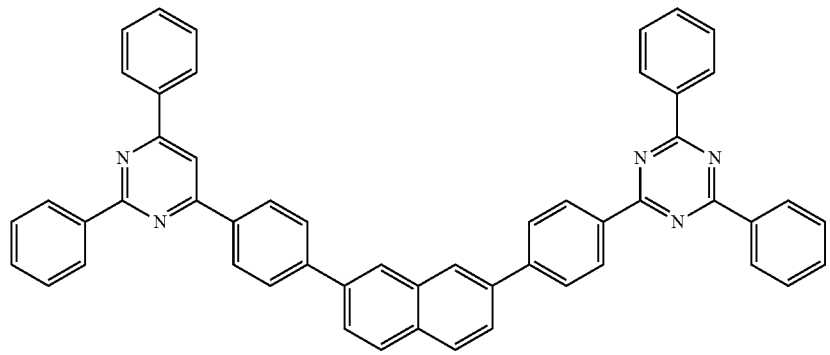

Chemical Formula 1-a-2

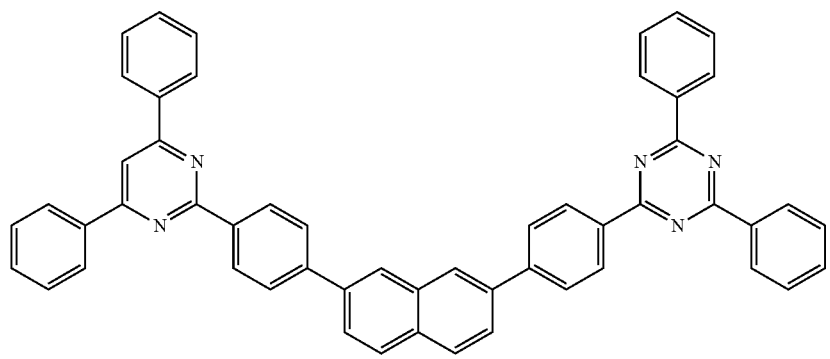

Chemical Formula 1-a-3

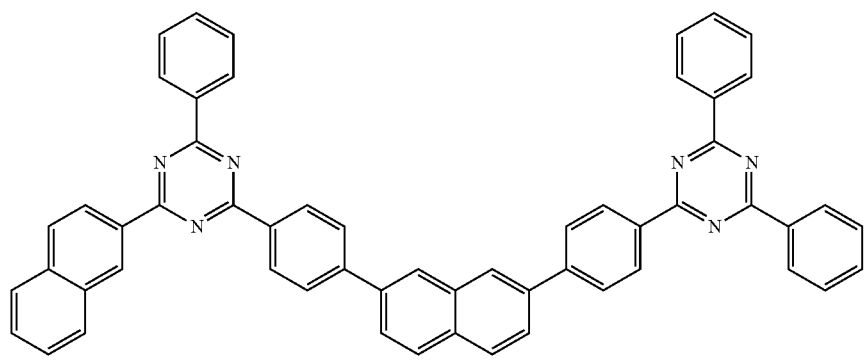

Chemical Formula 1-a-4
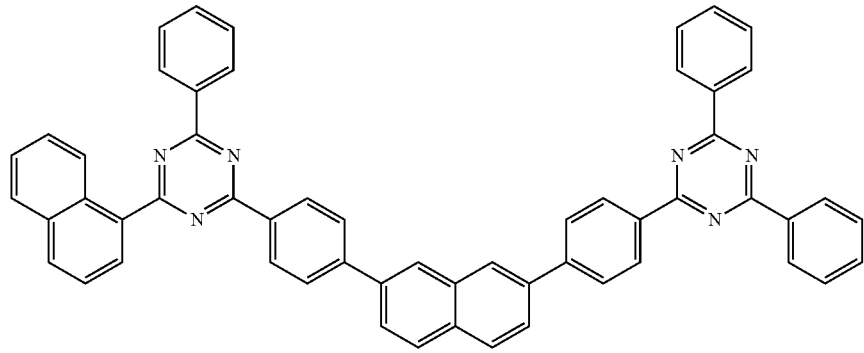
Chemical Formula 1-a-5
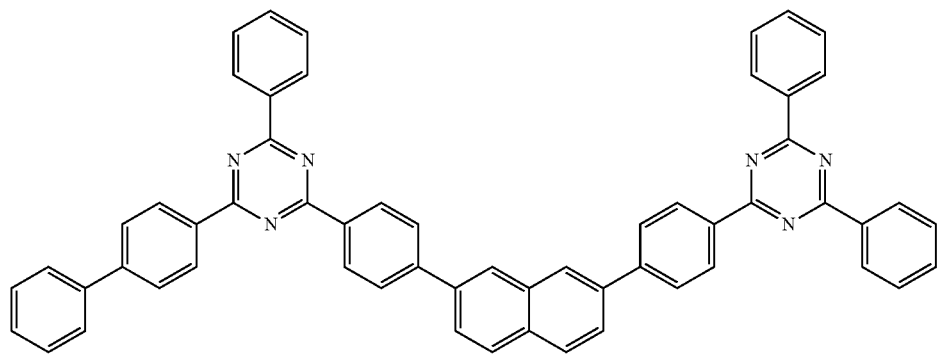
Chemical Formula 1-a-6
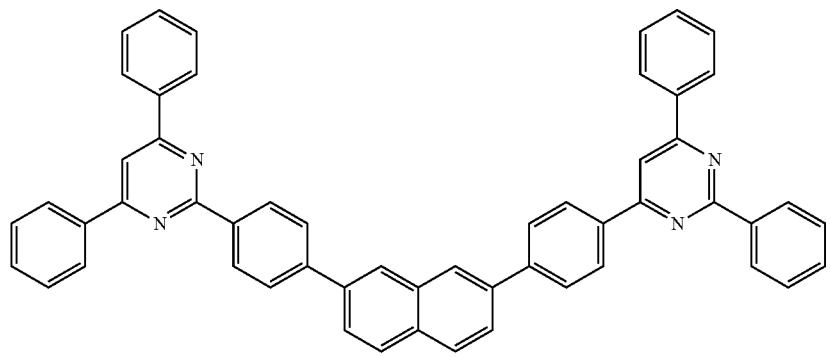
Chemical Formula 1-a-7
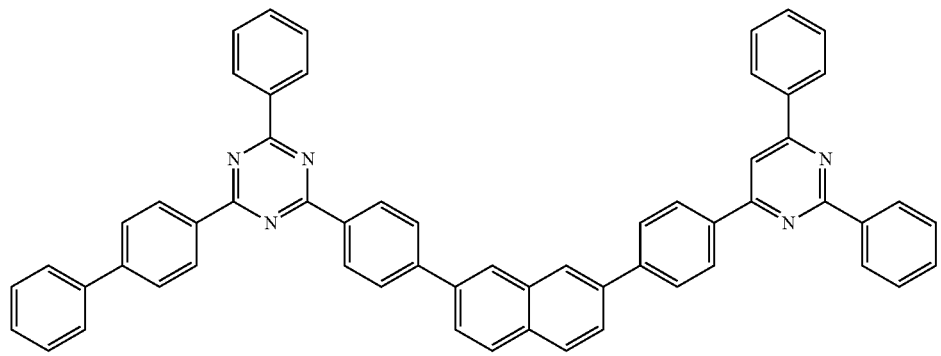

Chemical Formula 1-a-8
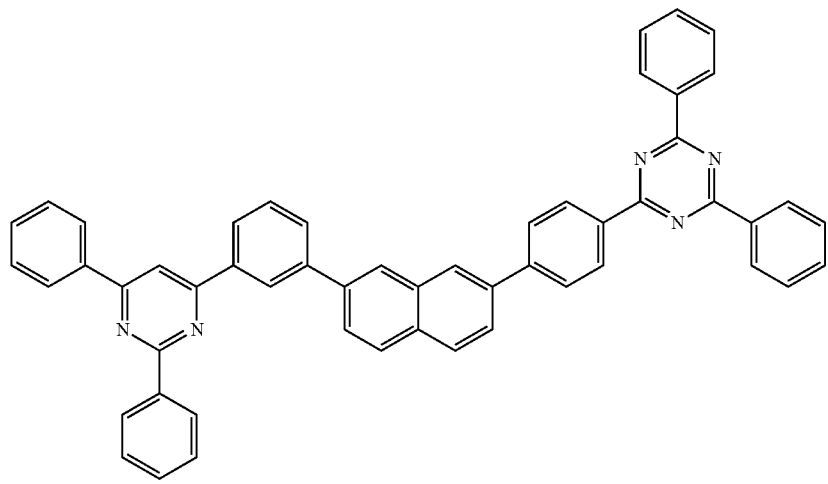
Chemical Formula 1-a-9
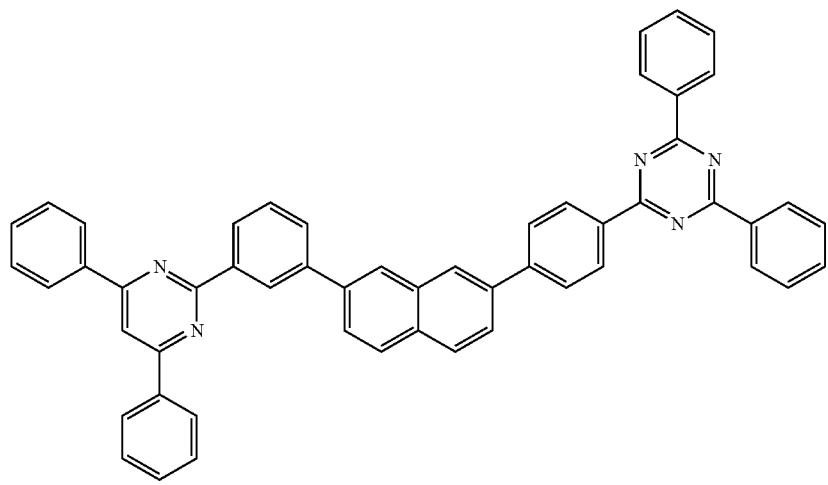
Chemical Formula 1-a-10
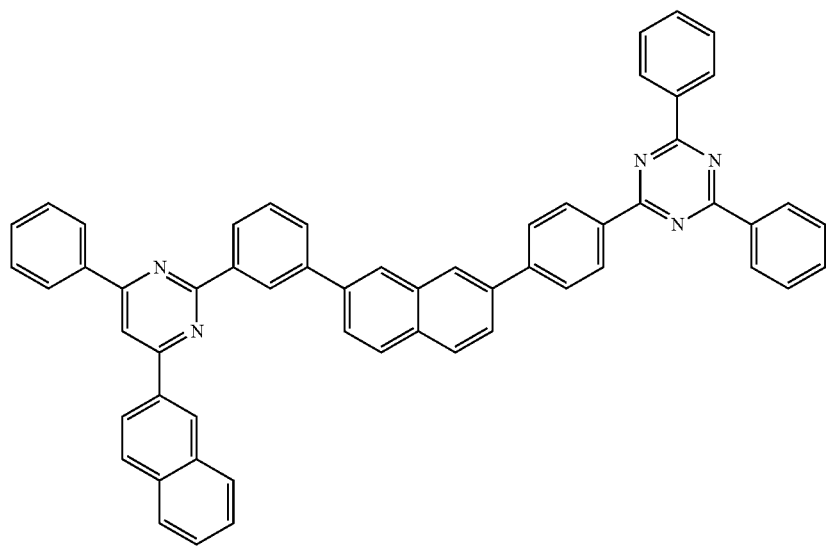

Chemical Formula 1-a-11
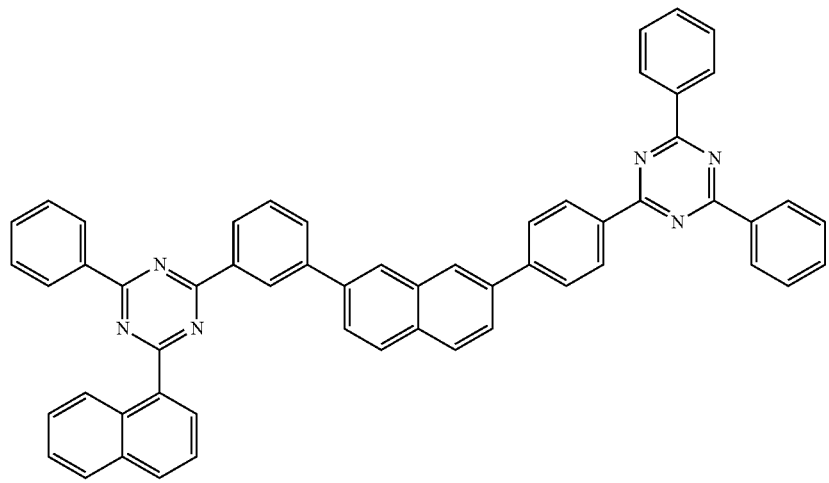
Chemical Formula 1-a-12
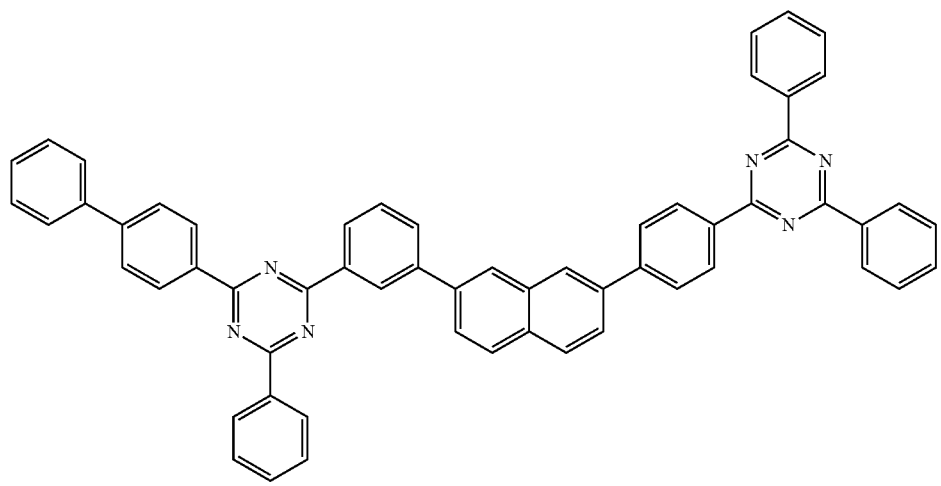
Chemical Formula 1-a-13
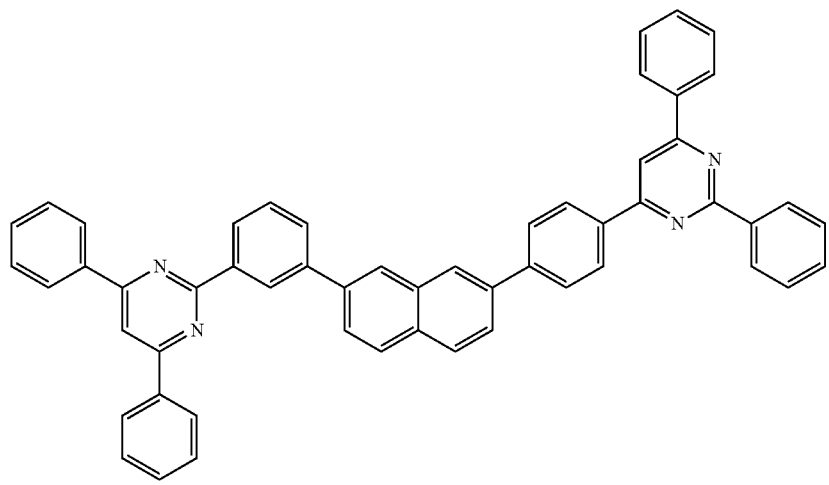

Chemical Formula 1-a-14
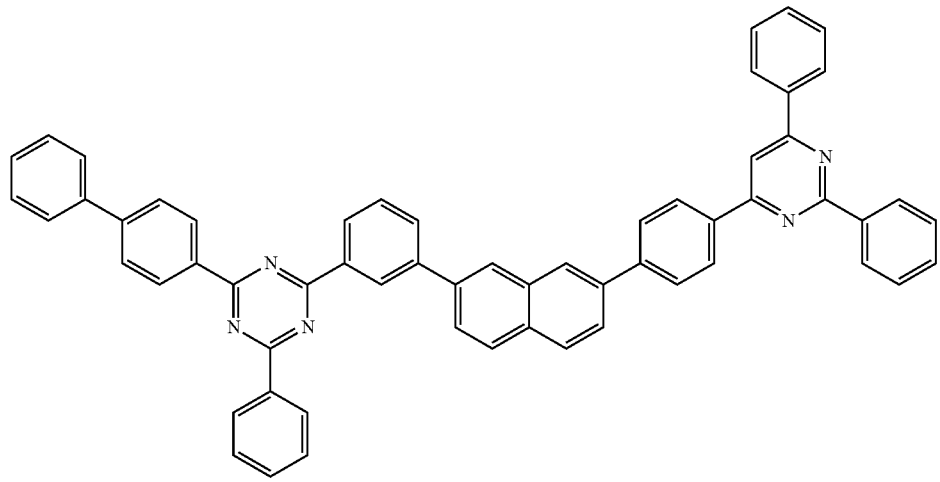
Chemical Formula 1-b-1
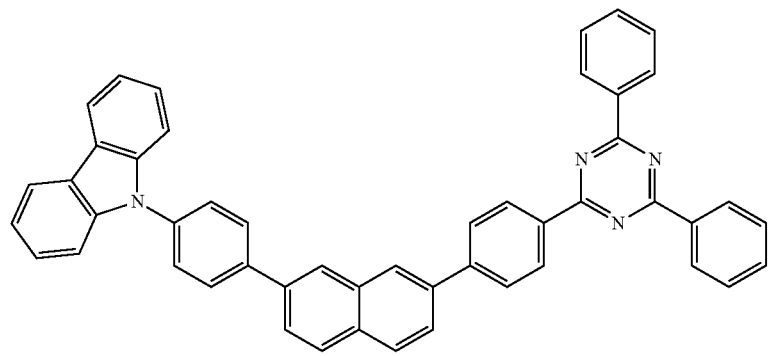
Chemical Formula 1-b-2
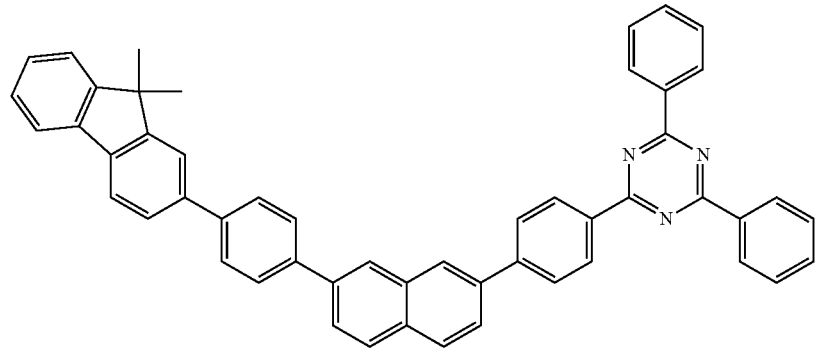
Chemical Formula 1-b-3
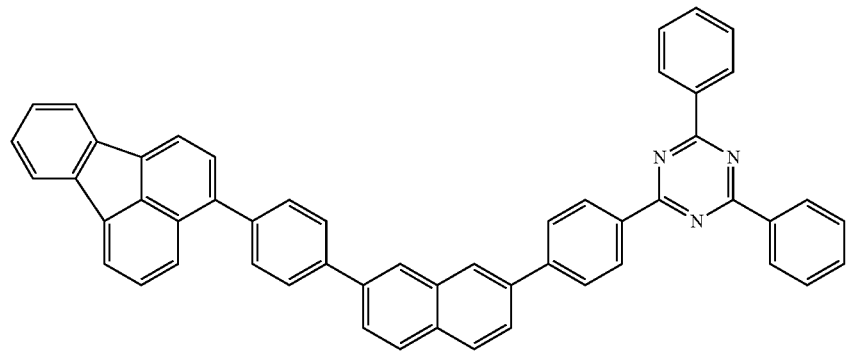

Chemical Formula 1-b-4
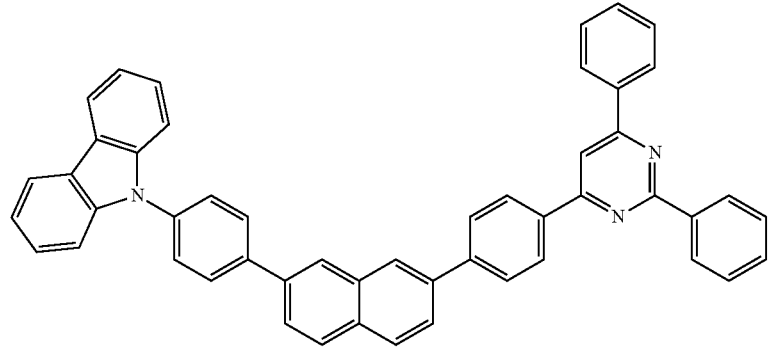
Chemical Formula 1-b-5
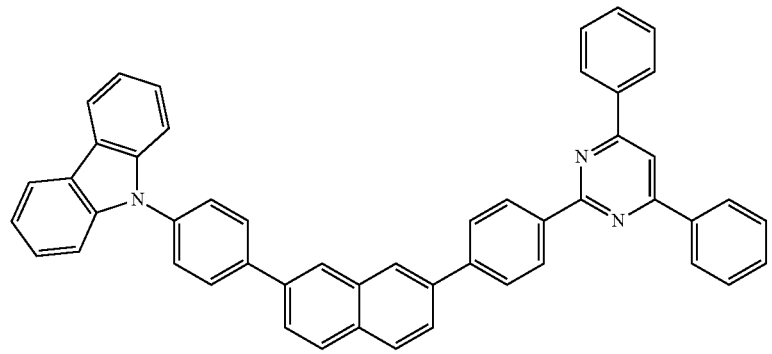
Chemical Formula 1-b-6
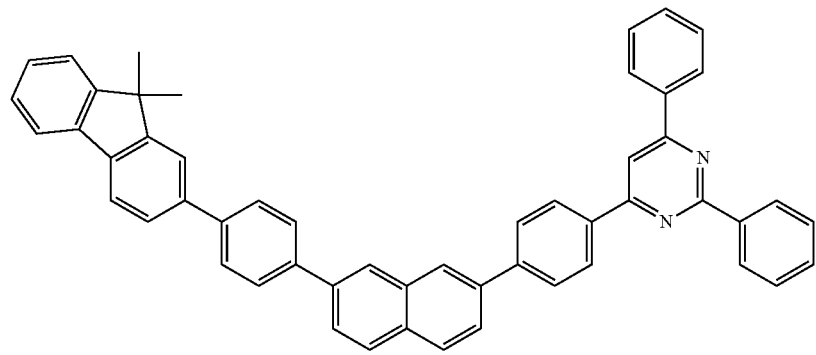
Chemical Formula 1-b-7
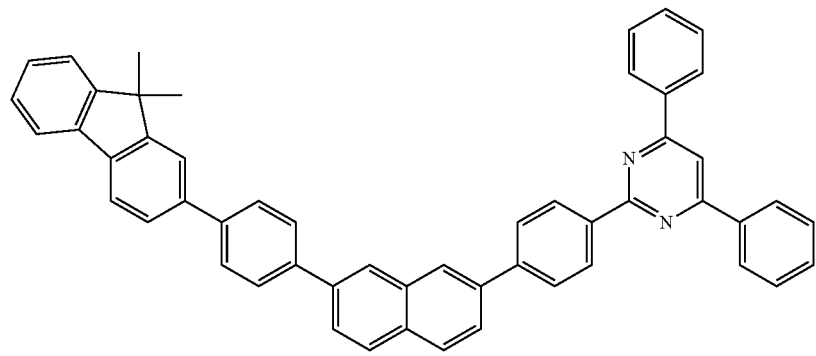

-continued
Chemical Formula 1-b-8
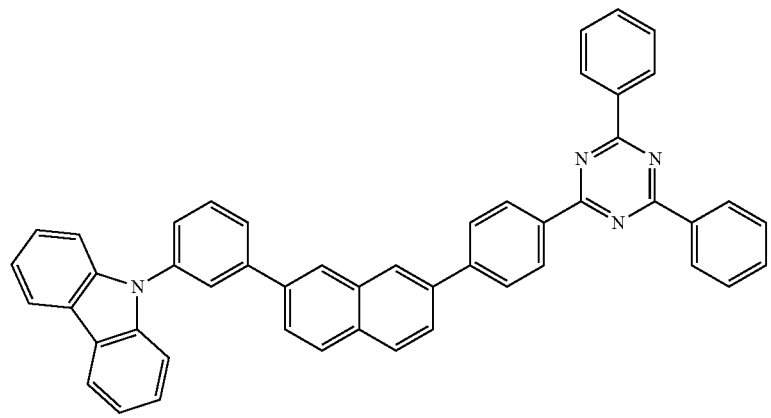
Chemical Formula 1-b-9
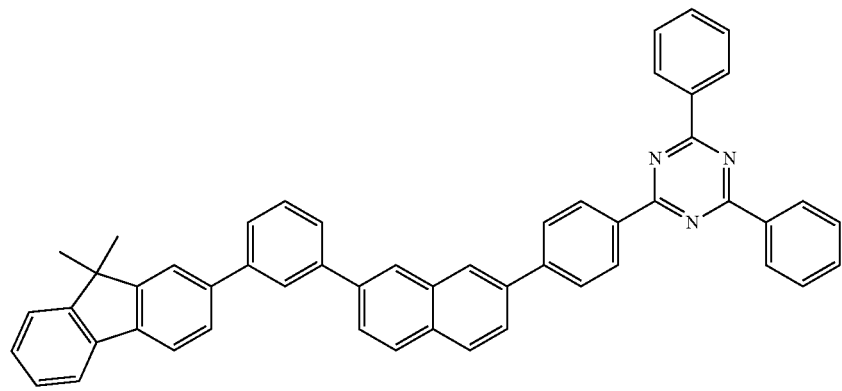
Chemical Formula 1-b-10
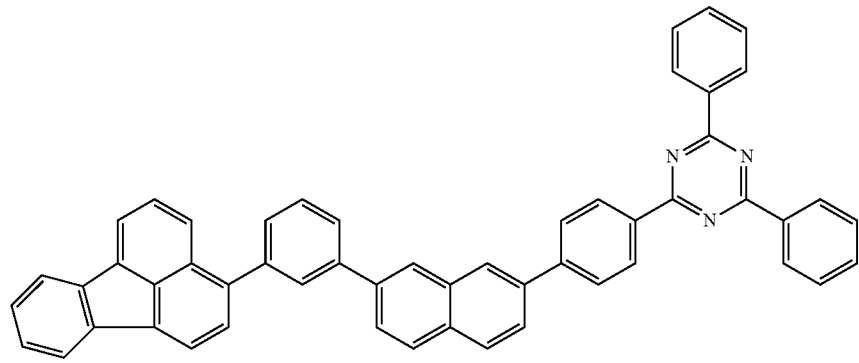
Chemical Formula 1-b-11
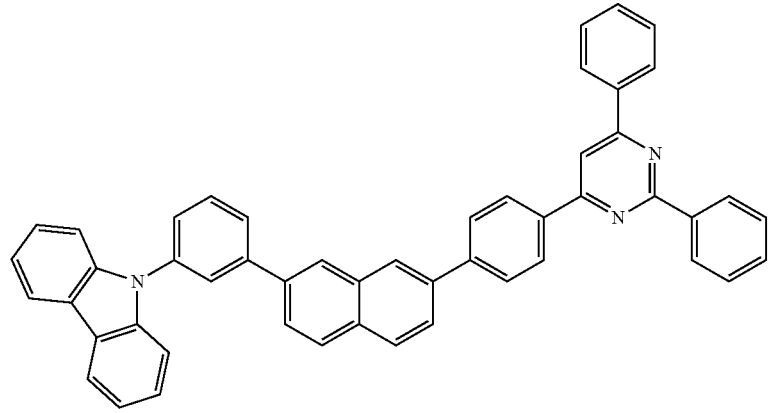

-continued
Chemical Formula 1-b-12
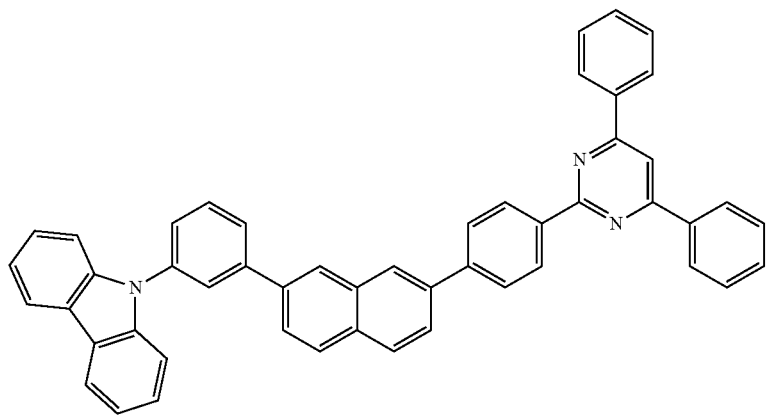
Chemical Formula 1-b-13
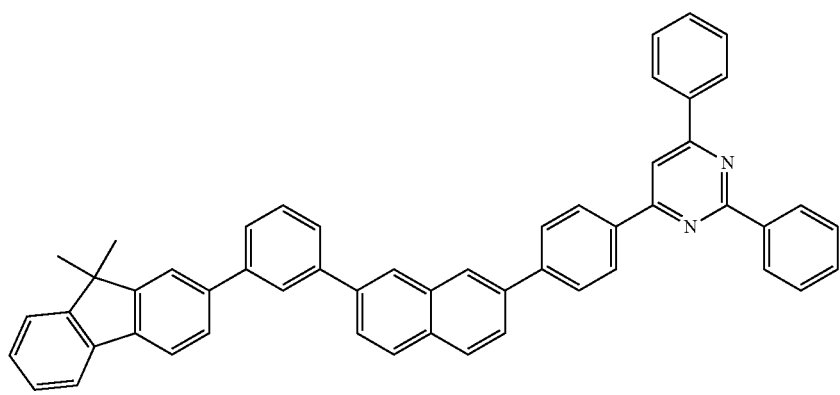
Chemical Formula 1-b-14
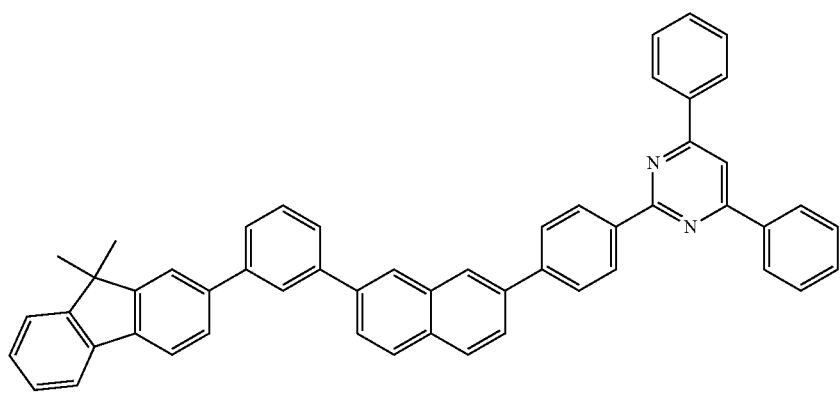
Chemical Formula 1-b-15
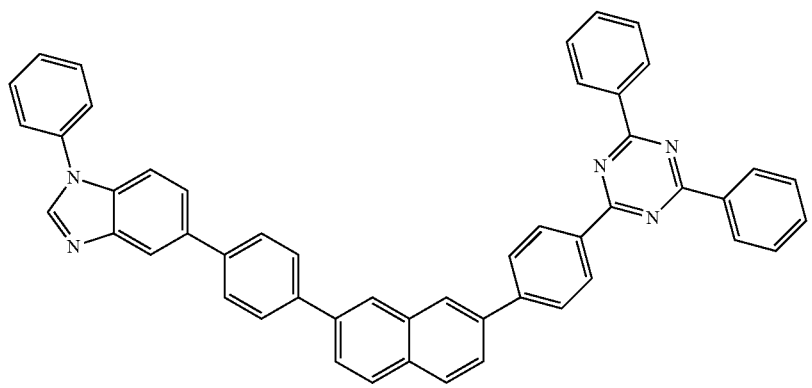

Chemical Formula 1-b-16
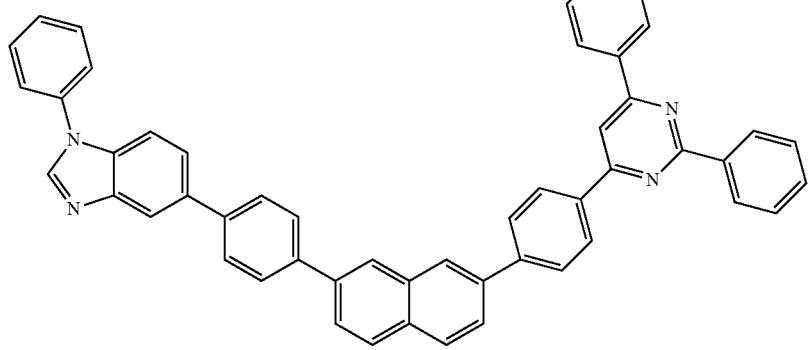
Chemical Formula 1-b-17
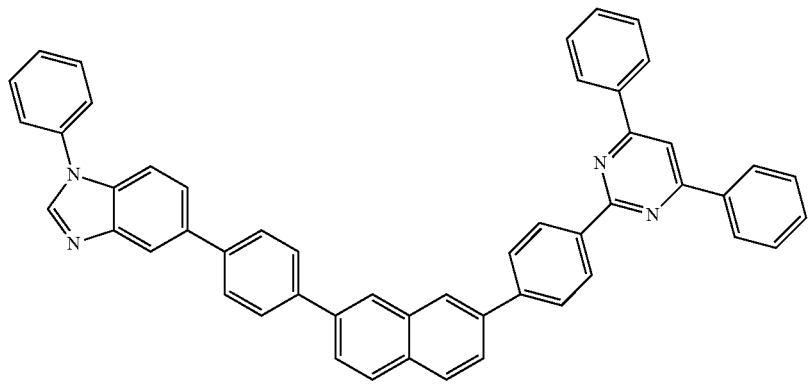
Chemical Formula 1-b-18
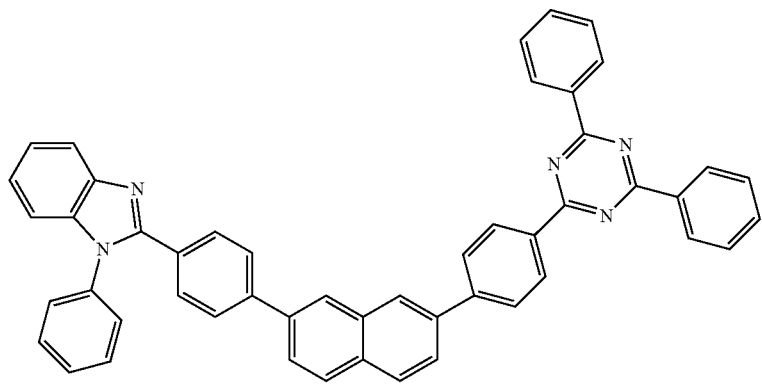
Chemical Formula 1-b-19
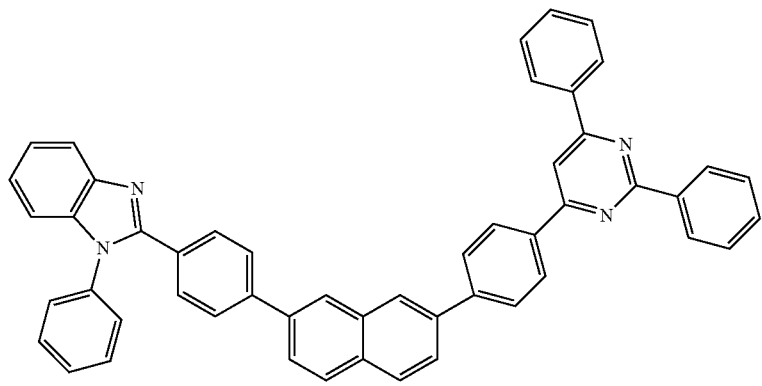

-continued
Chemical Formula 1-b-20
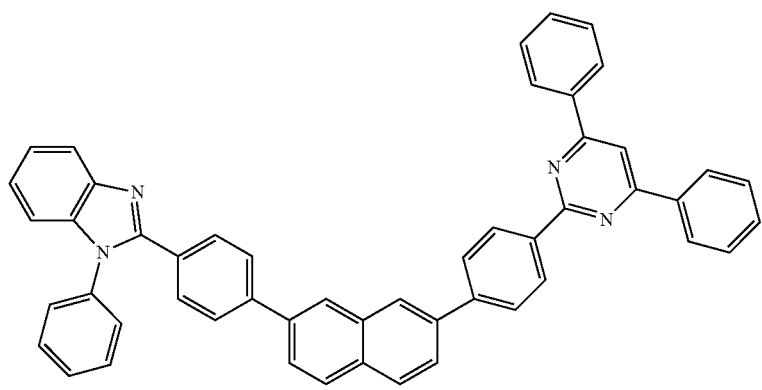
Chemical Formula 1-b-21
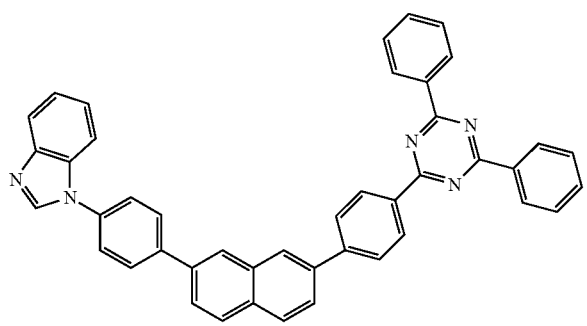
Chemical Formula 1-b-22
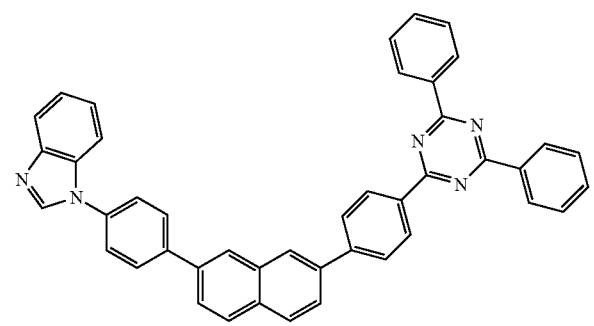
Chemical Formula 1-b-23
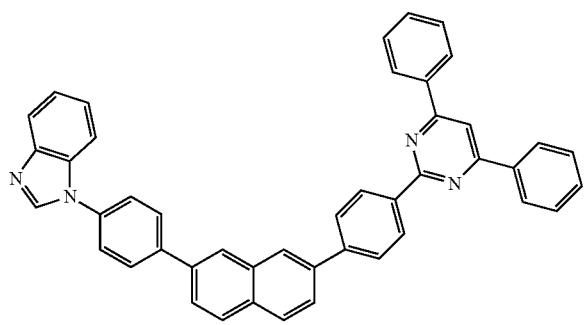
Chemical Formula 1-b-24
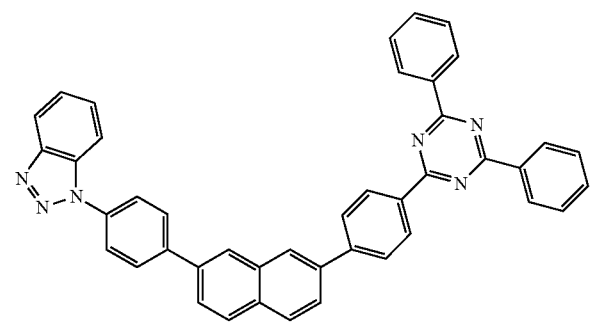
Chemical Formula 1-b-25
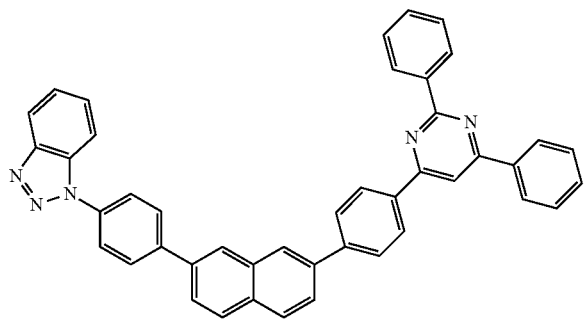
Chemical Formula 1-b-26
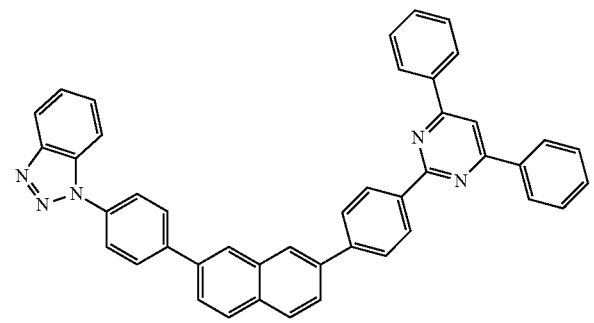

In one embodiment of the present specification, the compound represented by Chemical Formula 1-2 is represented by any one of the following Chemical Formulae 2-a-1 to 2-a-14, and 2-b-1 to 2-b-26.
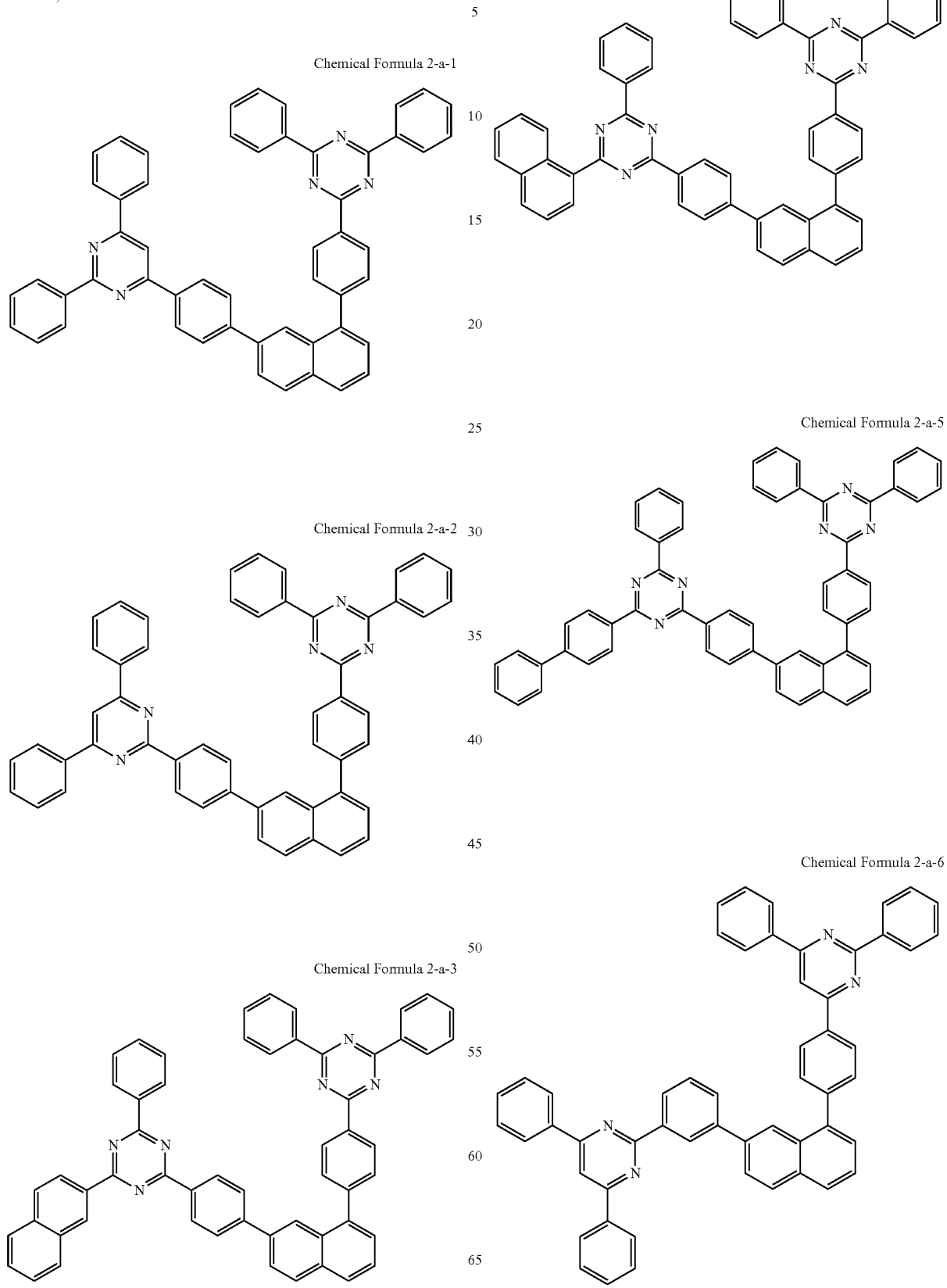
Chemical Formula 2-a-1
Chemical Formula 2-a-2
Chemical Formula 2-a-3
Chemical Formula 2-a-4
Chemical Formula 2-a-5
Chemical Formula 2-a-6

Chemical Formula 2-a-7
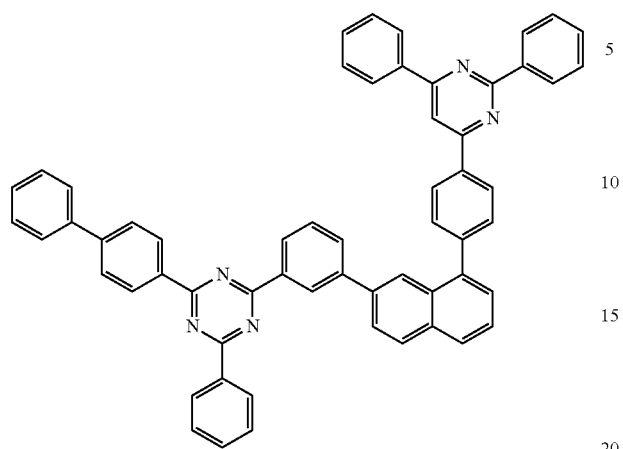
Chemical Formula 2-a-8
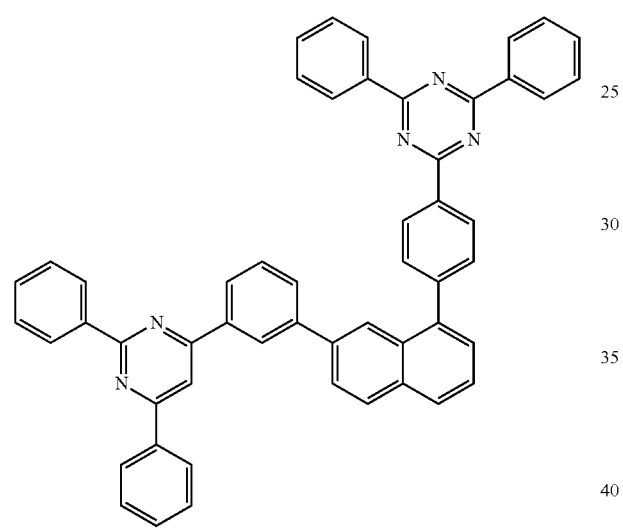
Chemical Formula 2-a-9
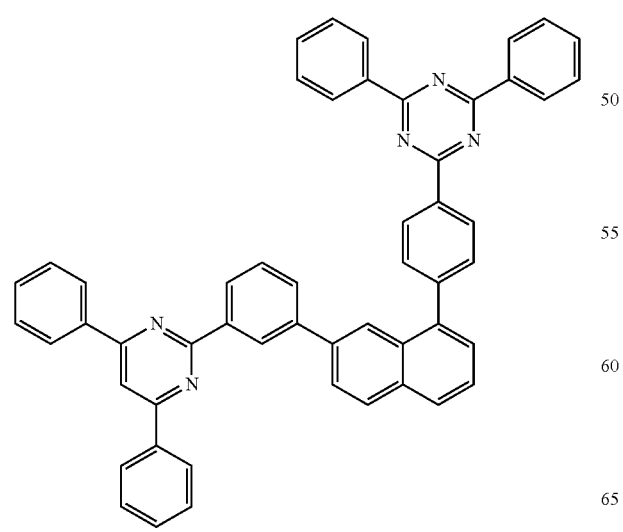
Chemical Formula 2-a-10
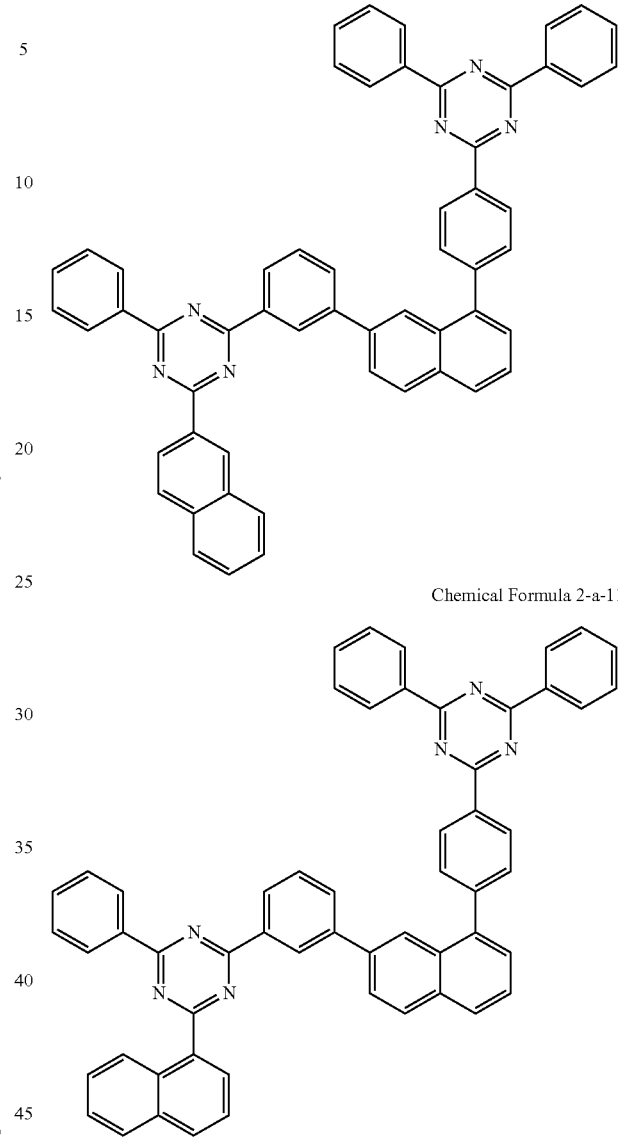
Chemical Formula 2-a-11
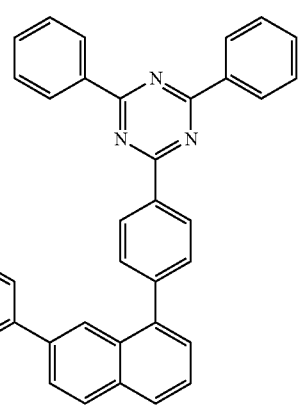
Chemical Formula 2-a-12
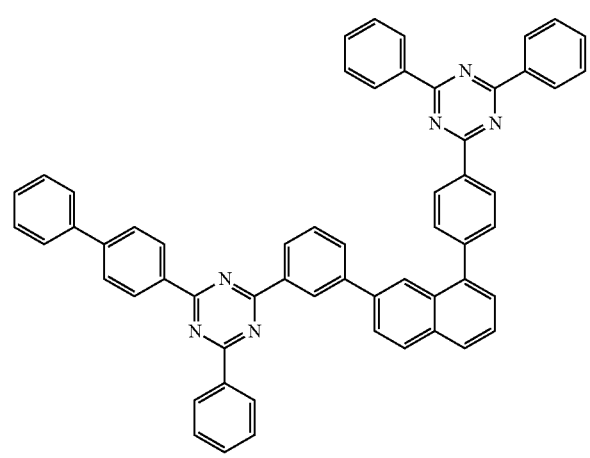

Chemical Formula 2-a-13
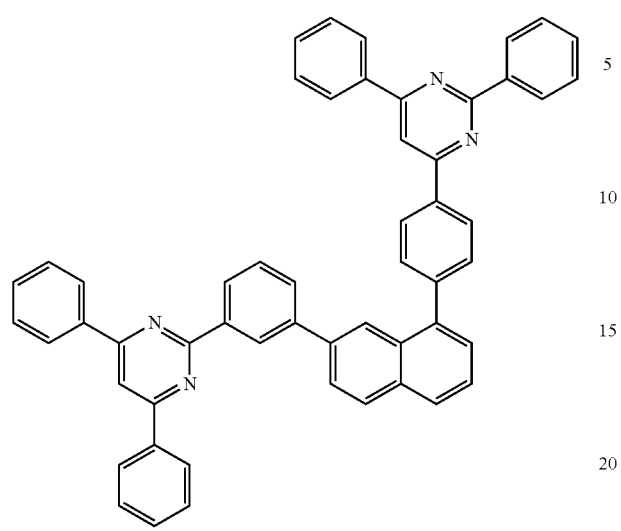
Chemical Formula 2-a-14
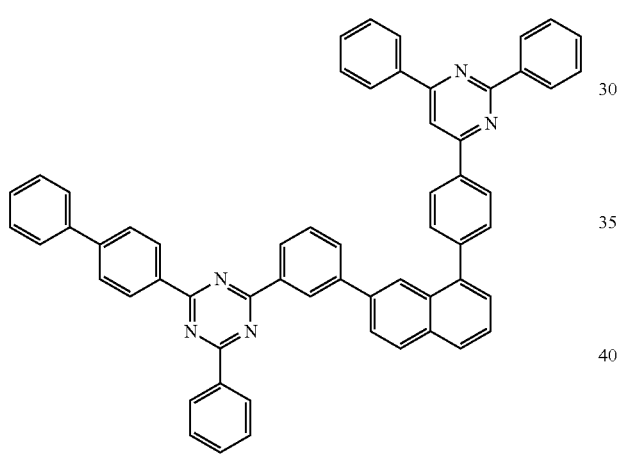
Chemical Formula 2-b-1
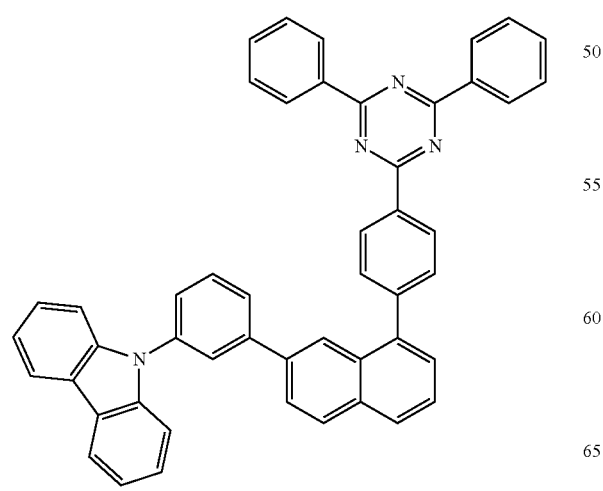
Chemical Formula 2-b-2
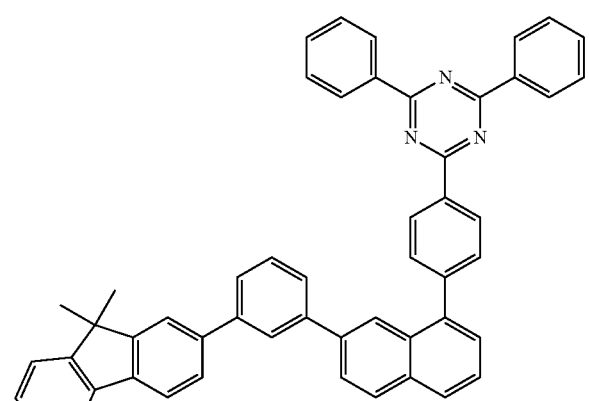
Chemical Formula 2-b-3
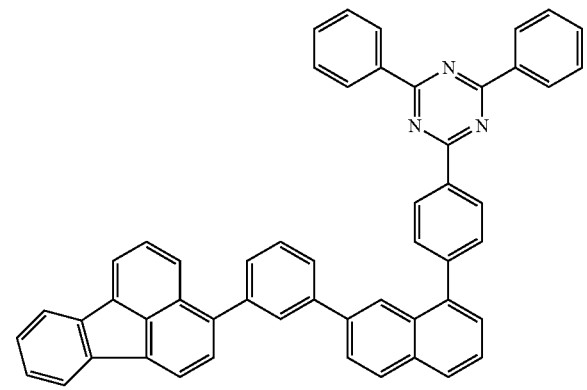
Chemical Formula 2-b-4
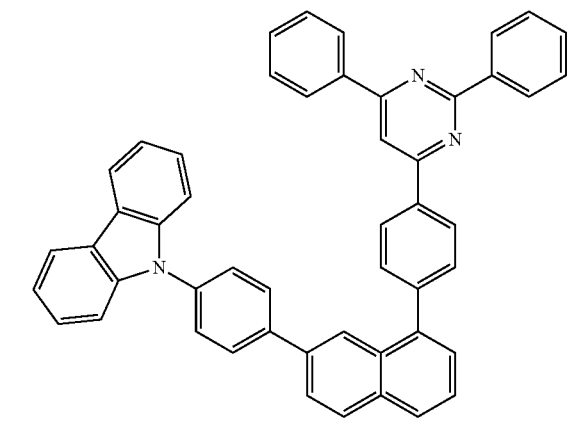

Chemical Formula 2-b-5
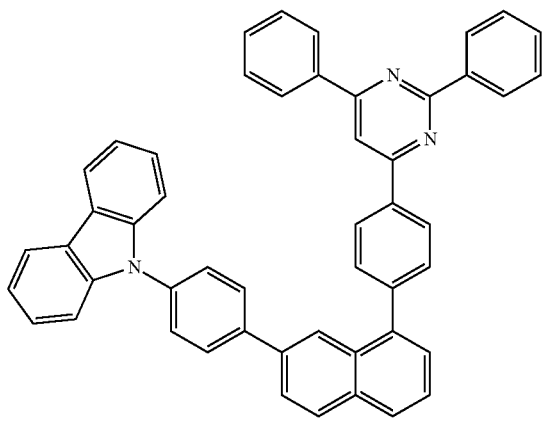
Chemical Formula 2-b-6
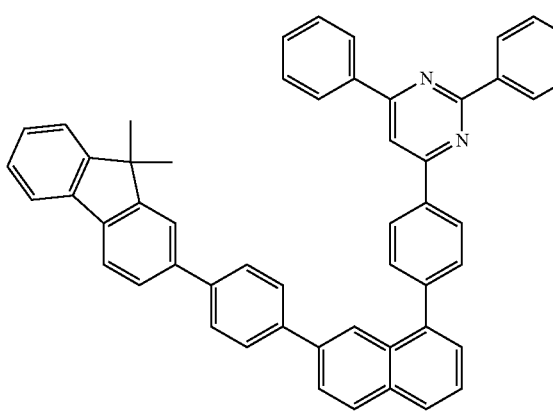
Chemical Formula 2-b-7
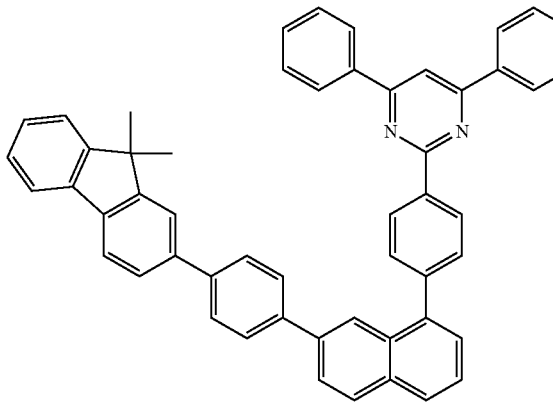
Chemical Formula 2-b-8
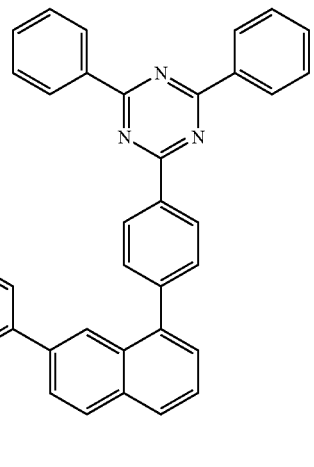
Chemical Formula 2-b-9
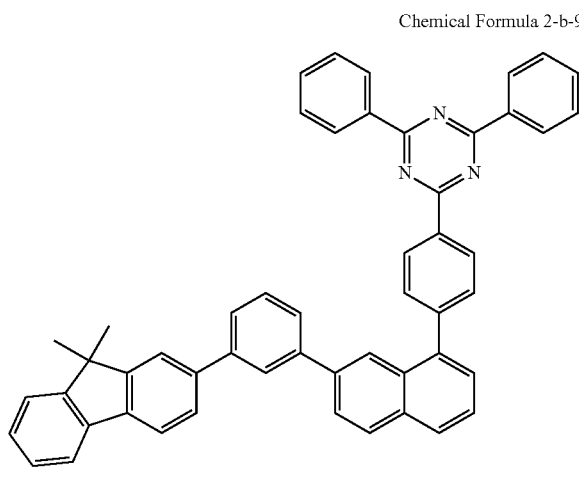
Chemical Formula 2-b-10
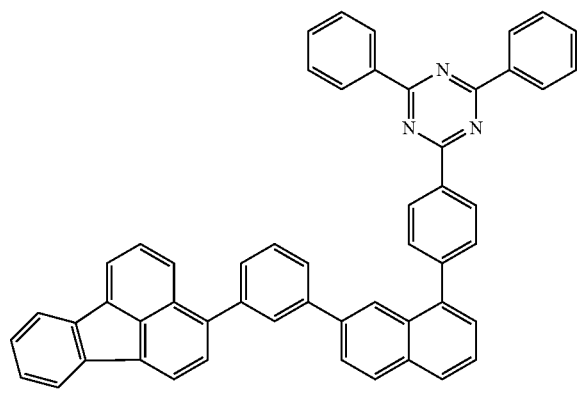

-continued
Chemical Formula 2-b-11
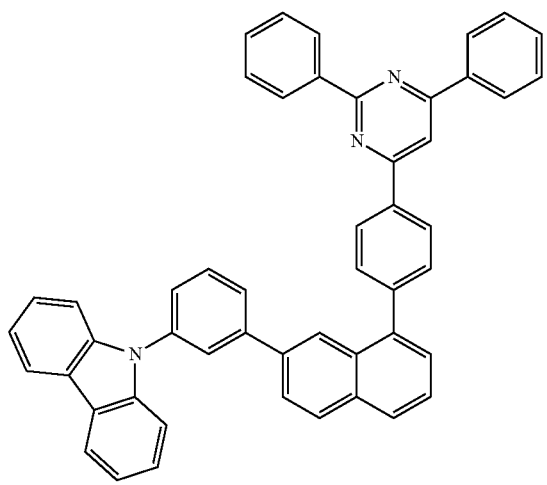
Chemical Formula 2-b-12
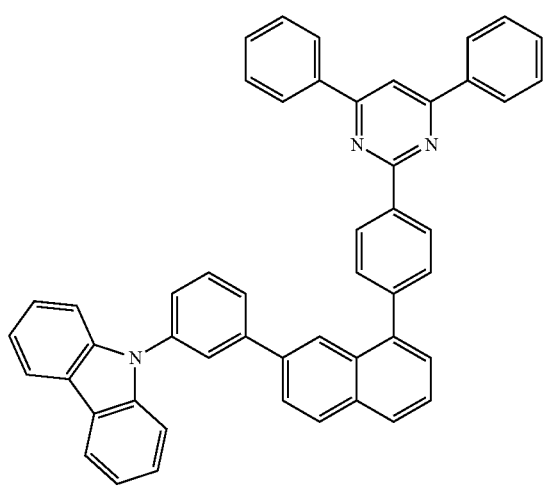
Chemical Formula 2-b-13
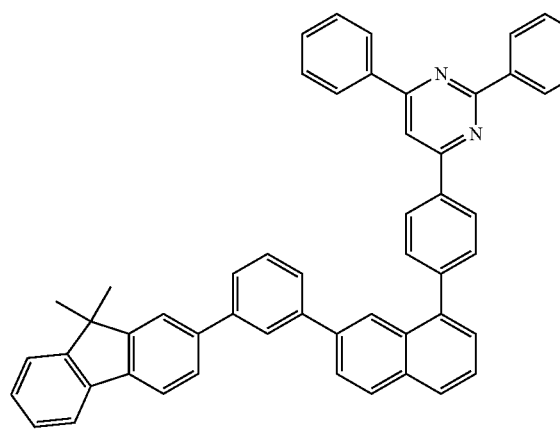
Chemical Formula 2-b-14
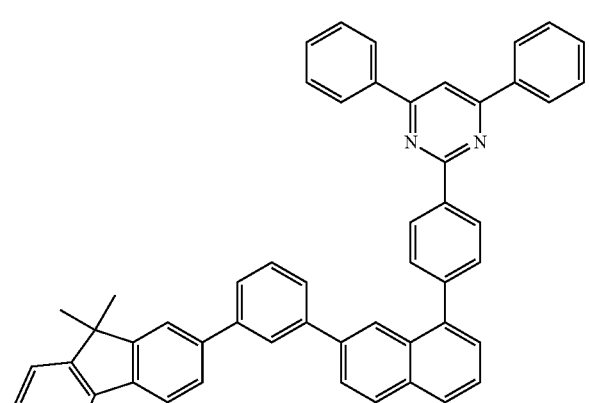
Chemical Formula 2-b-15
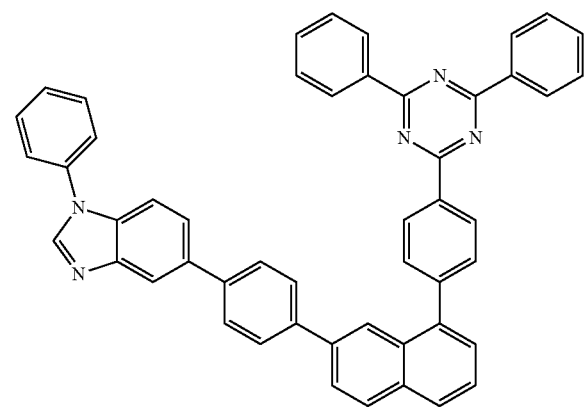
Chemical Formula 2-b-16
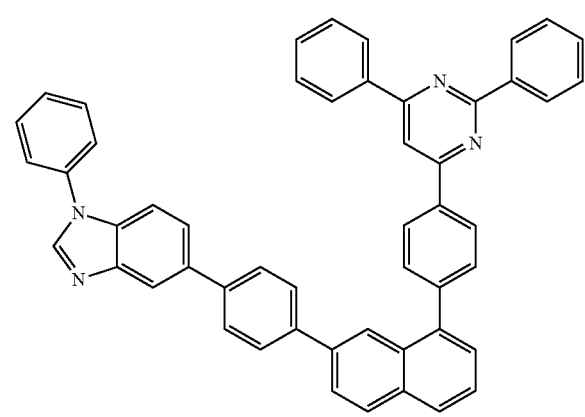

Chemical Formula 2-b-17
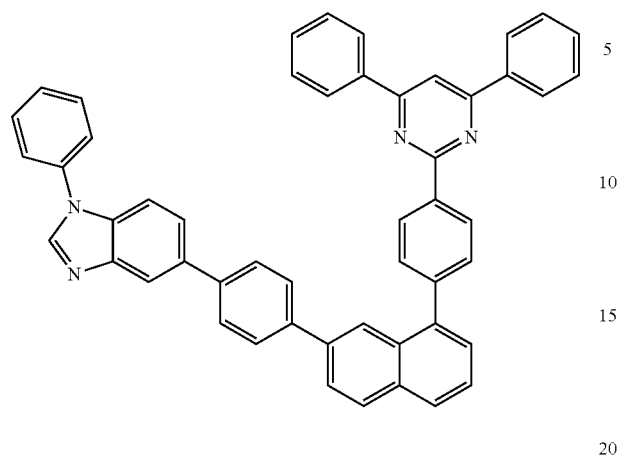
Chemical Formula 2-b-18
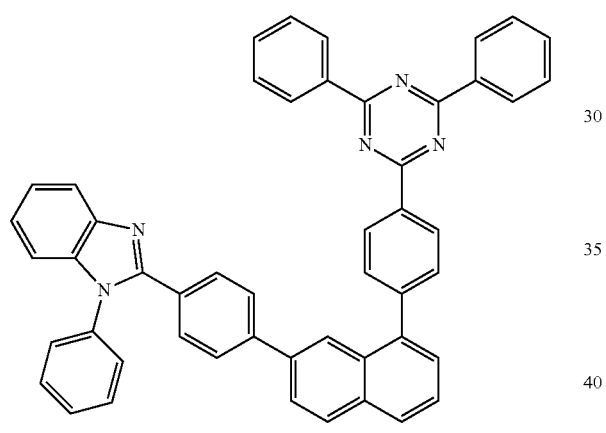
Chemical Formula 2-b-19
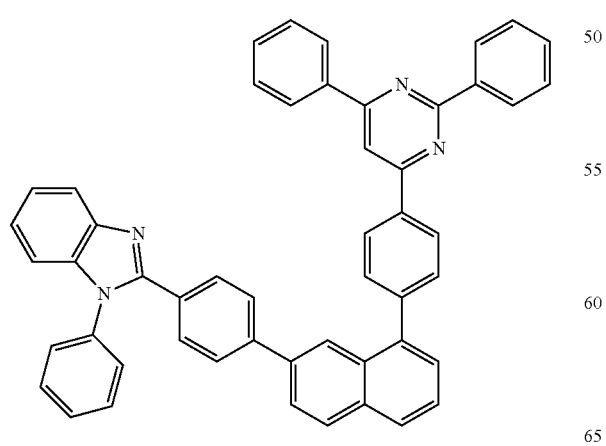
Chemical Formula 2-b-20
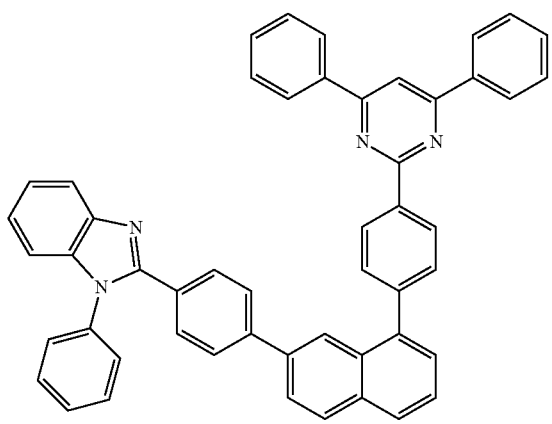
Chemical Formula 2-b-21
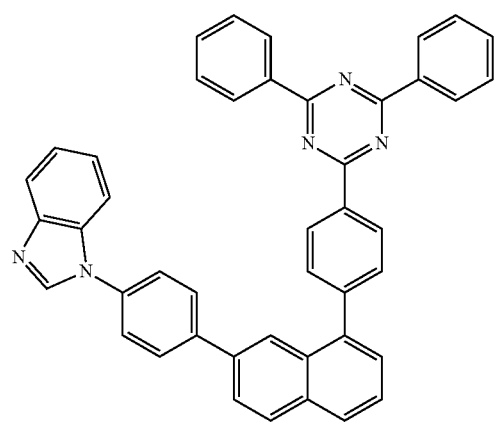
Chemical Formula 2-b-22
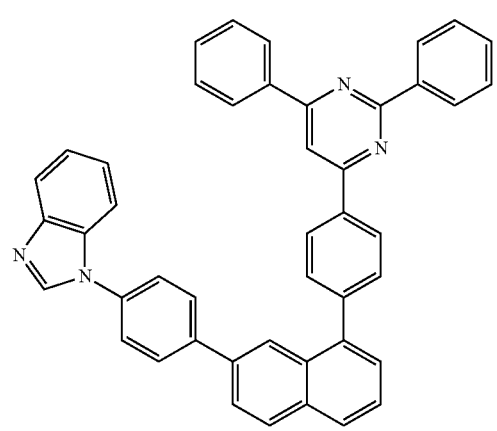

Chemical Formula 2-b-23
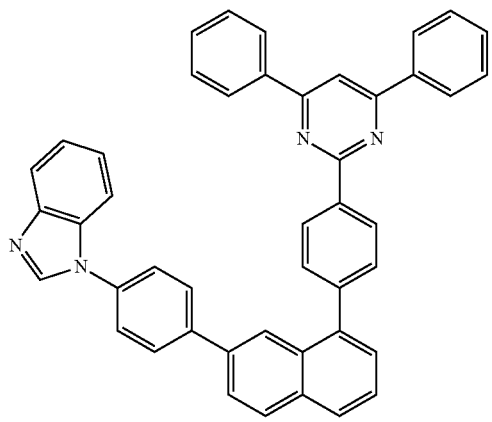
Chemical Formula 2-b-26
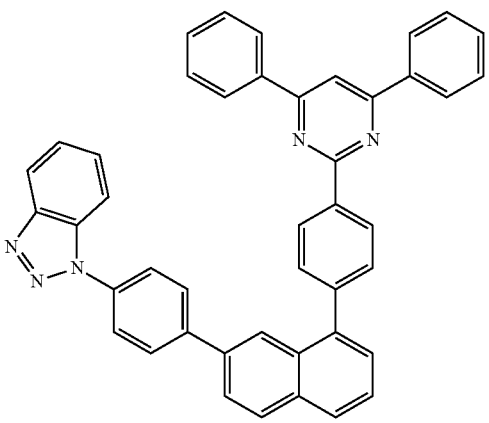
Chemical Formula 2-b-24
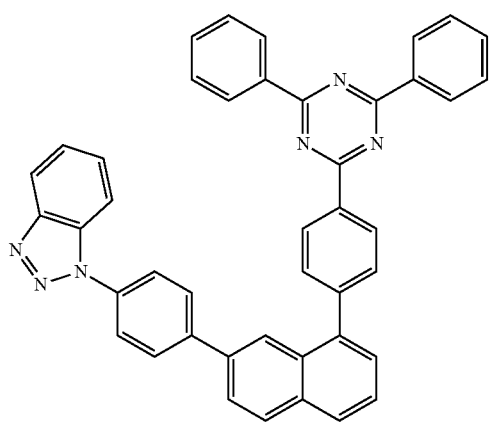
In one embodiment of the present specification, the compound represented by Chemical Formula 1-3 is represented by any one of the following Chemical Formulae 3-a-1 to 3-a-14, and 3-b-1 to 3-b-26.
Chemical Formula 3-a-1
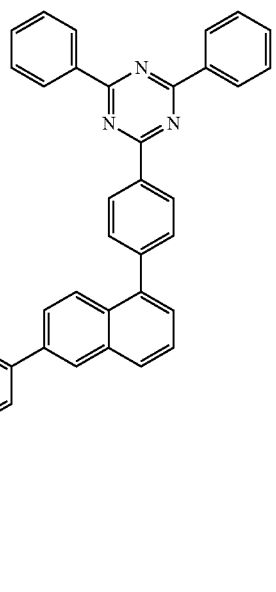
Chemical Formula 2-b-25
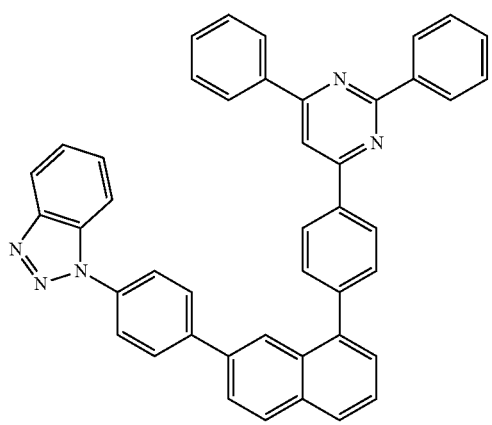

Chemical Formula 3-a-2
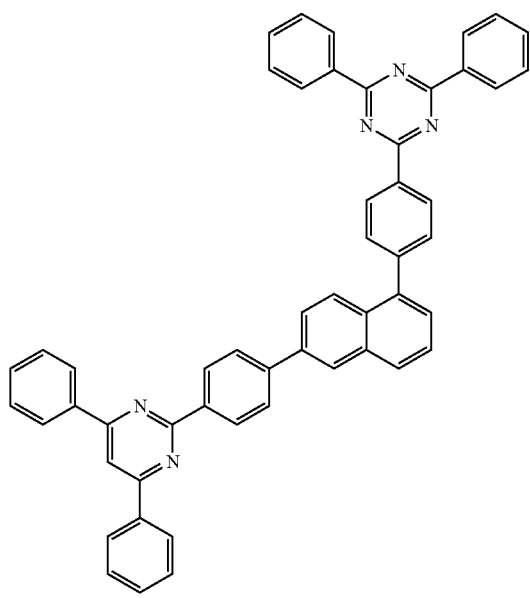
Chemical Formula 3-a-3
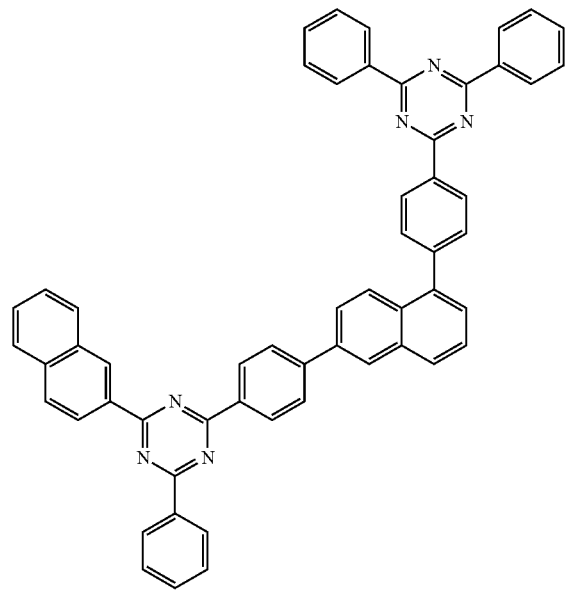
Chemical Formula 3-a-4
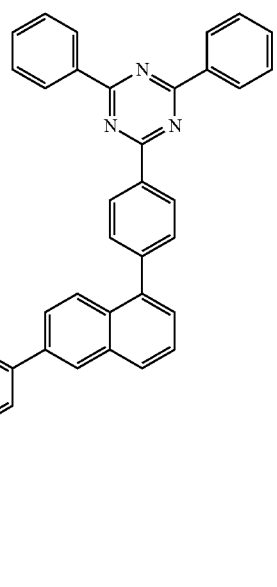
Chemical Formula 3-a-5
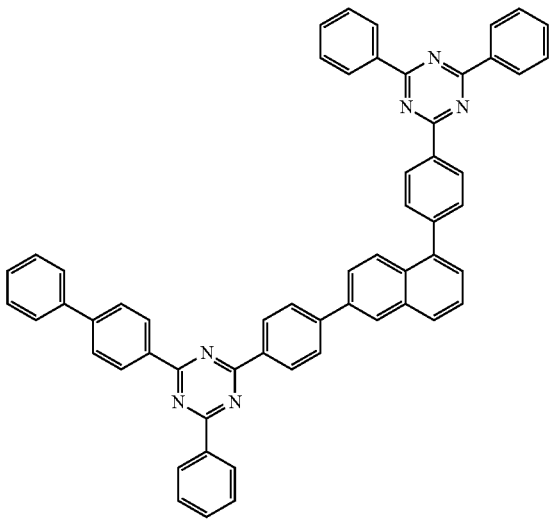

Chemical Formula 3-a-6
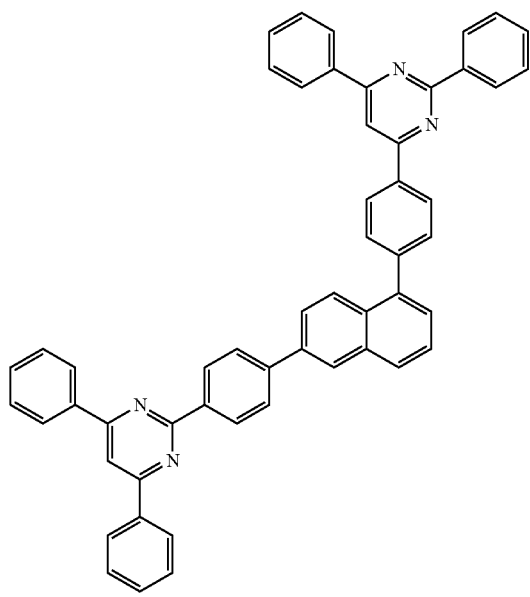
Chemical Formula 3-a-7
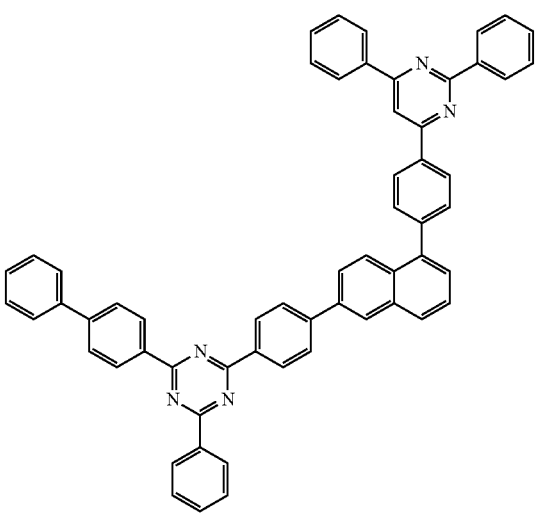
Chemical Formula 3-a-8
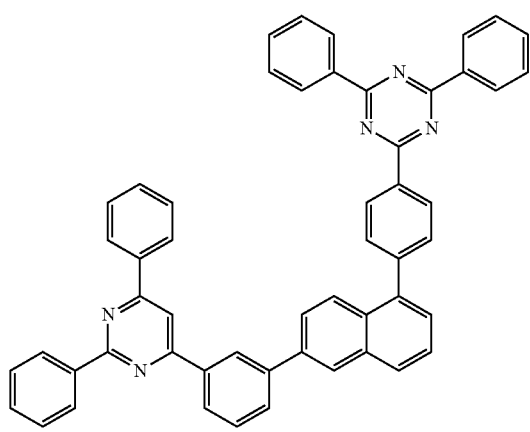
Chemical Formula 3-a-9
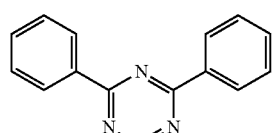
Chemical Formula 3-a-10
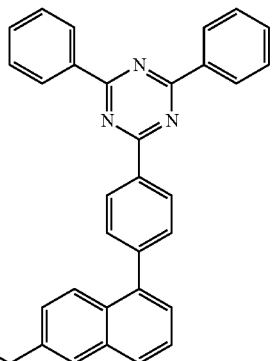
Chemical Formula 3-a-11
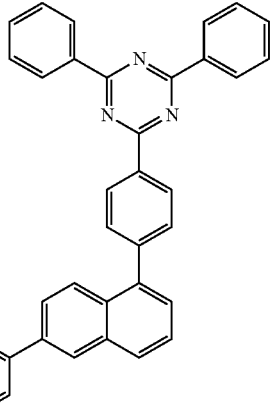

Chemical Formula 3-a-12
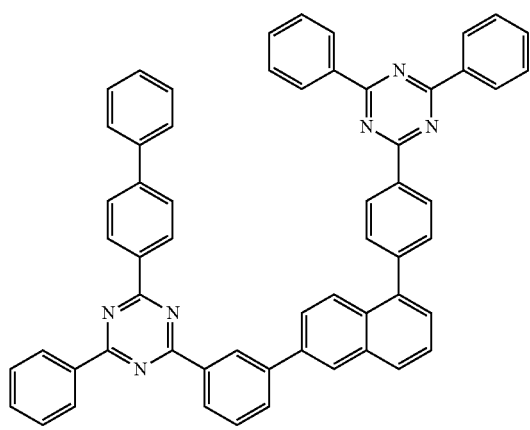
Chemical Formula 3-a-13
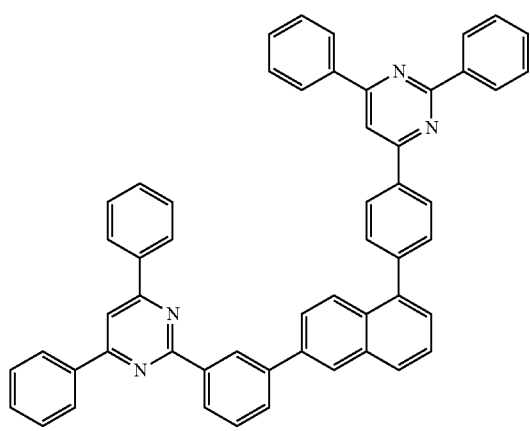
Chemical Formula 3-a-14
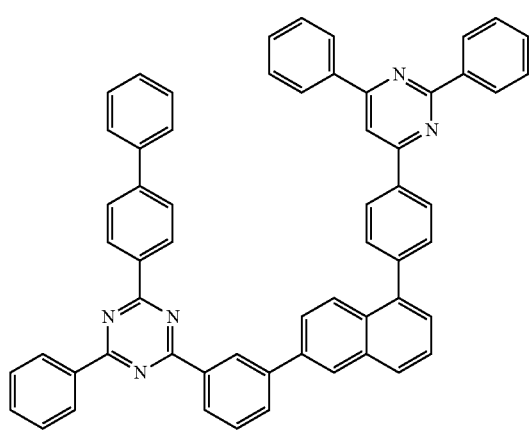
Chemical Formula 3-b-1
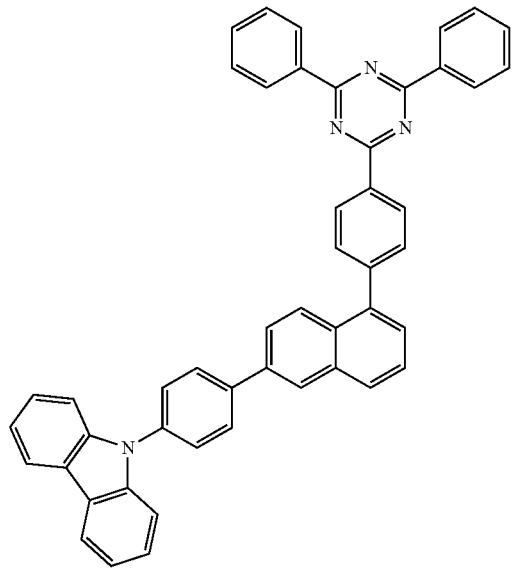
Chemical Formula 3-b-2
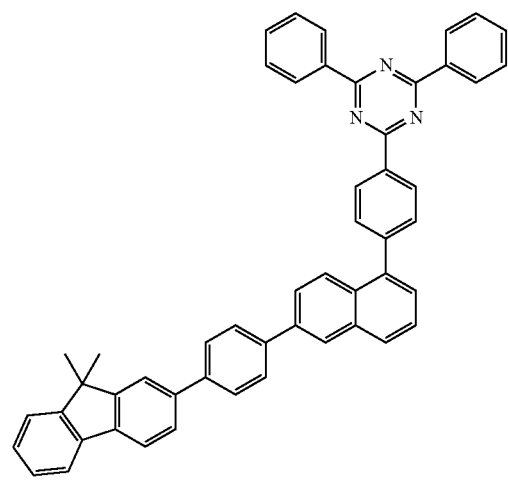
Chemical Formula 3-b-3
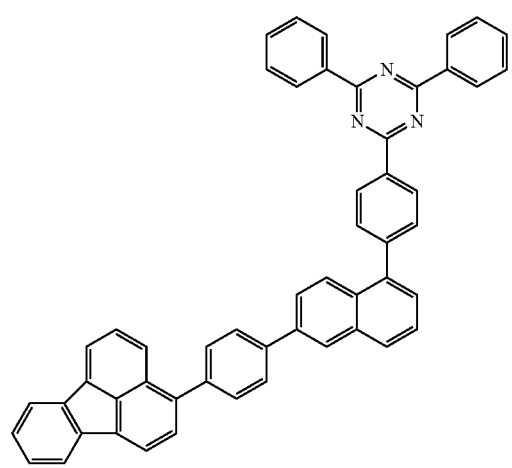

Chemical Formula 3-b-4
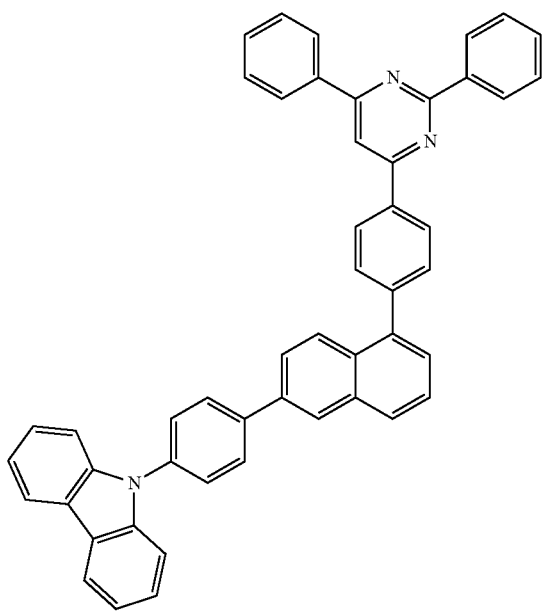
Chemical Formula 3-b-5
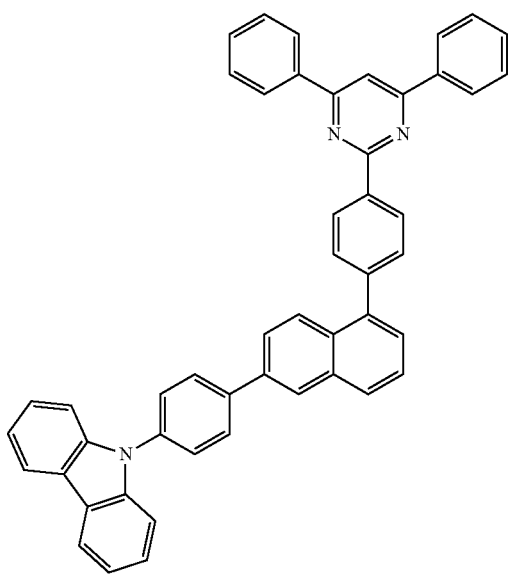
Chemical Formula 3-b-6
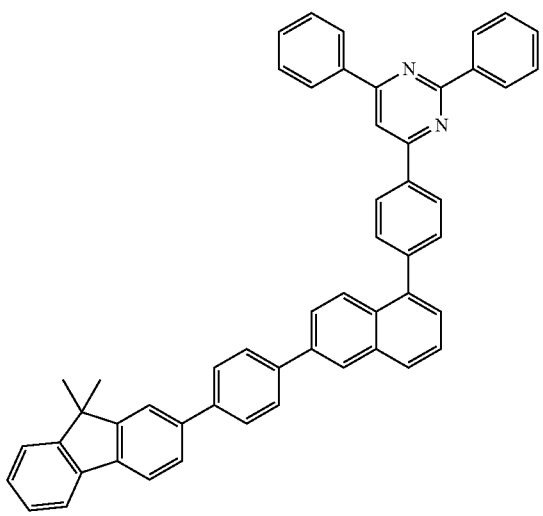
Chemical Formula 3-b-7
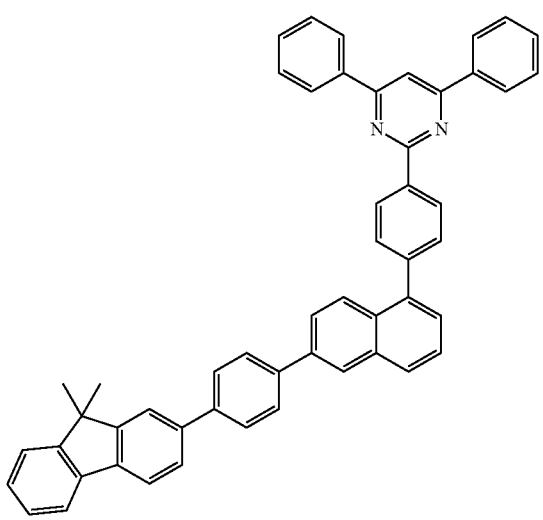
Chemical Formula 3-b-8
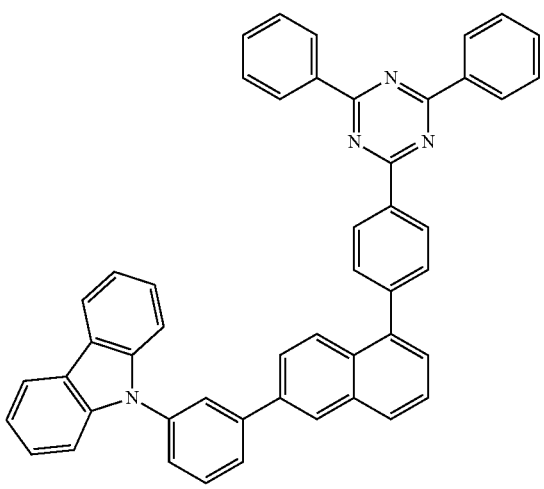

Chemical Formula 3-b-9
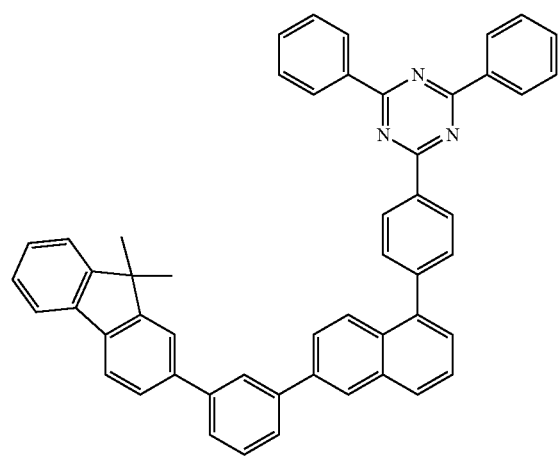
Chemical Formula 3-b-10
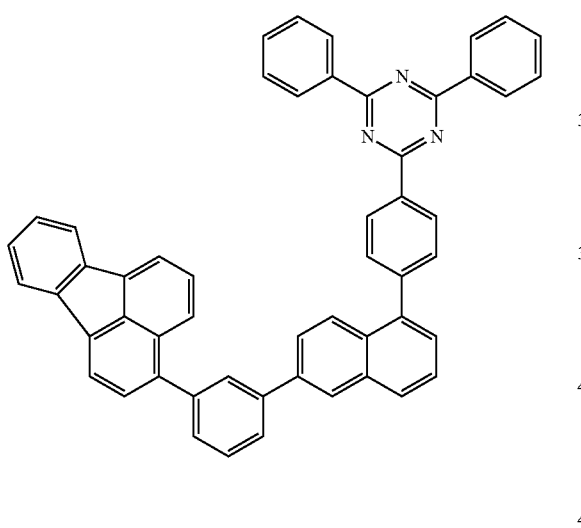
Chemical Formula 3-b-11
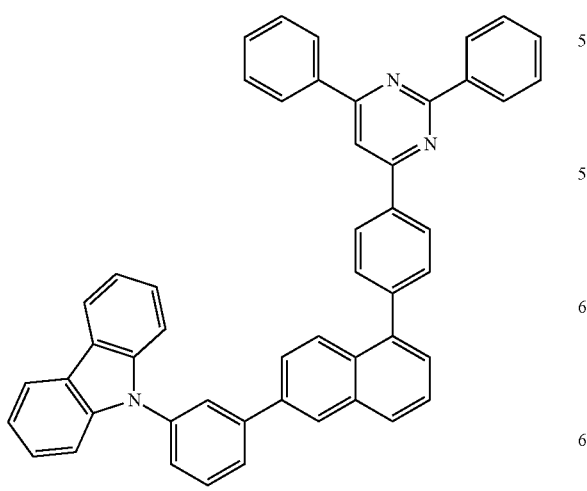
Chemical Formula 3-b-12
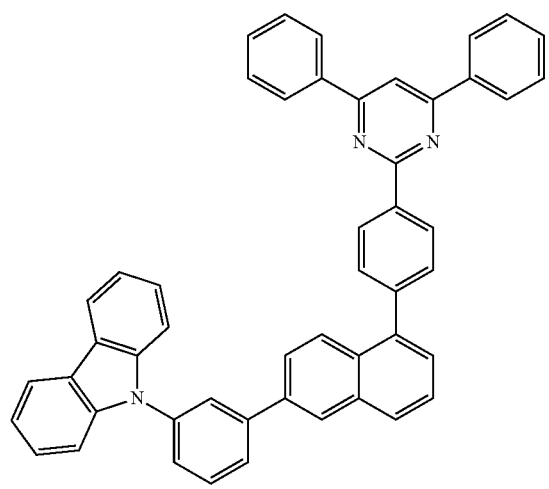
Chemical Formula 3-b-13
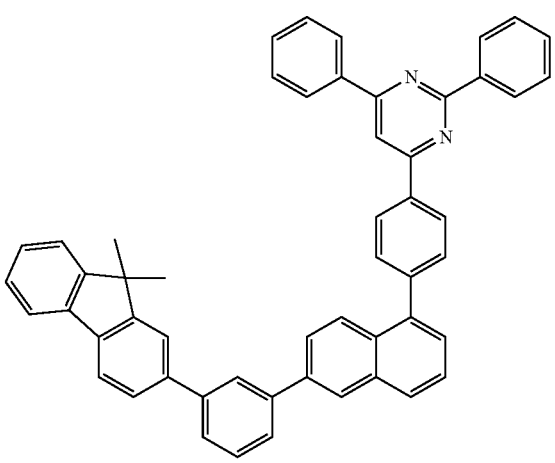
Chemical Formula 3-b-14
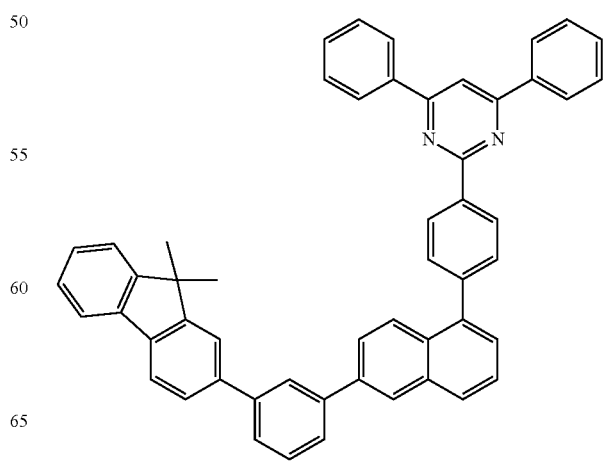

-continued
Chemical Formula 3-b-15
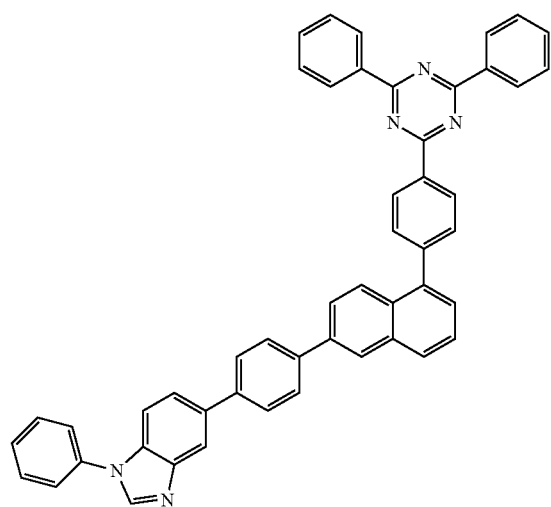
Chemical Formula 3-b-16
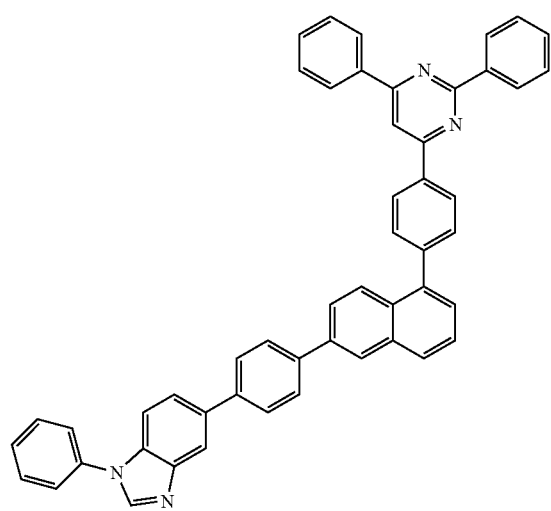
Chemical Formula 3-b-17
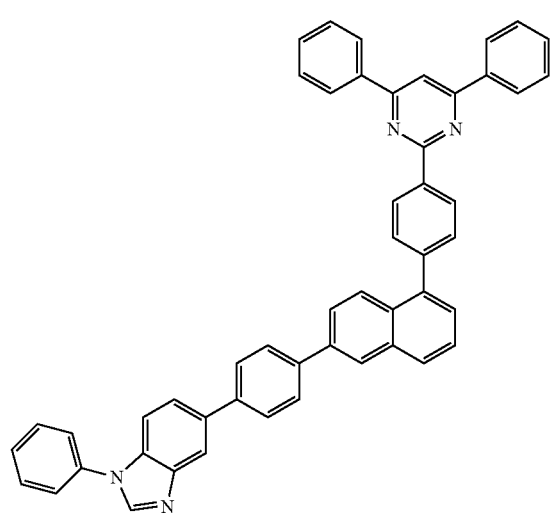
-continued
Chemical Formula 3-b-18
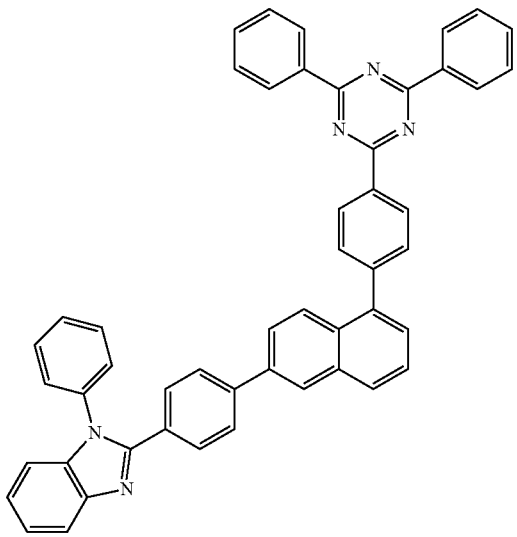
Chemical Formula 3-b-19
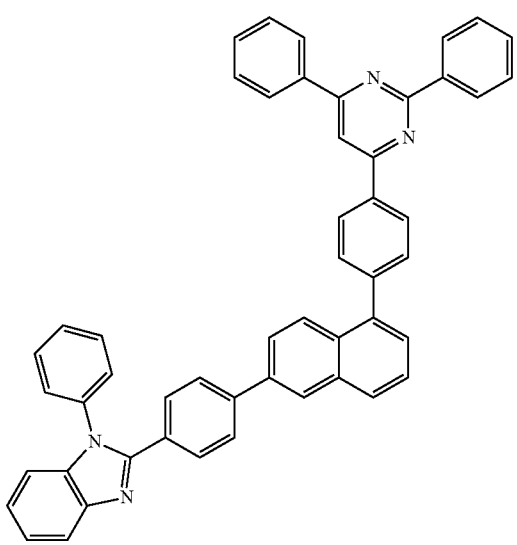
Chemical Formula 3-b-20
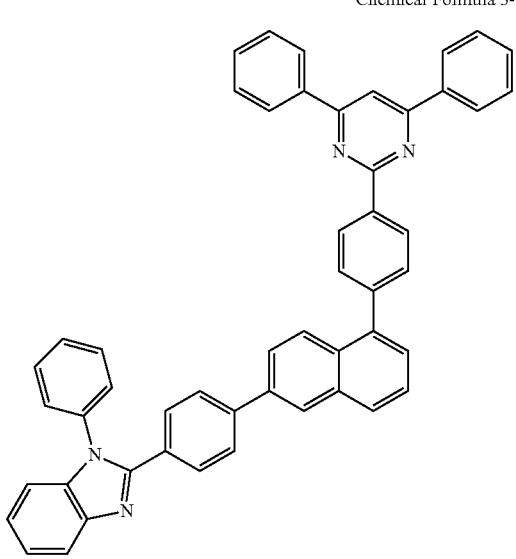

Chemical Formula 3-b-21
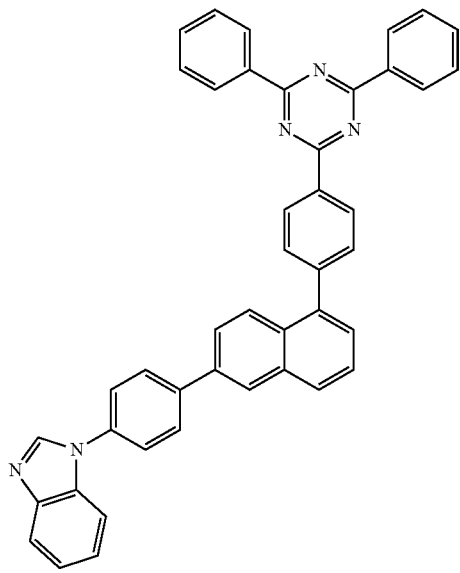
Chemical Formula 3-b-22
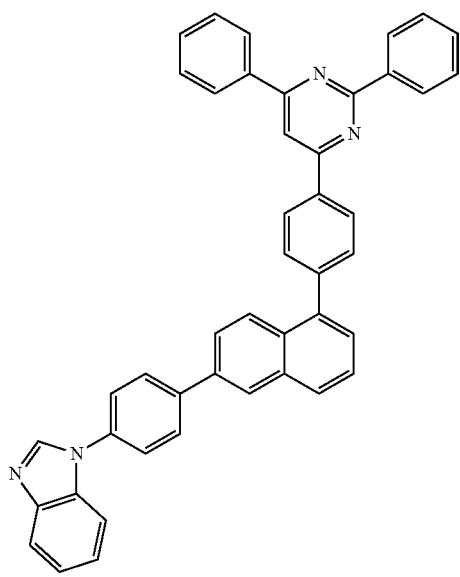
Chemical Formula 3-b-23
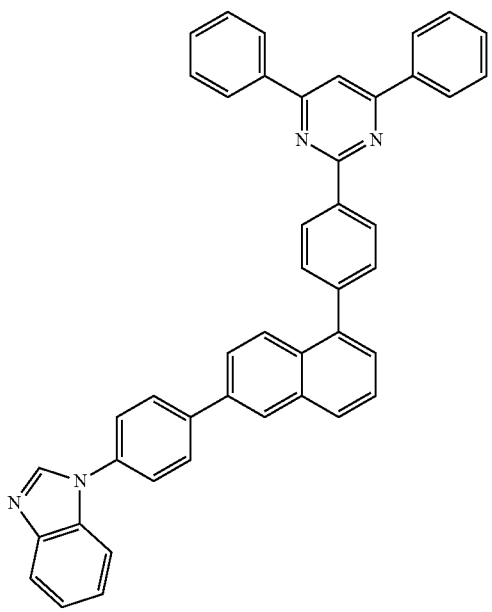
Chemical Formula 3-b-24
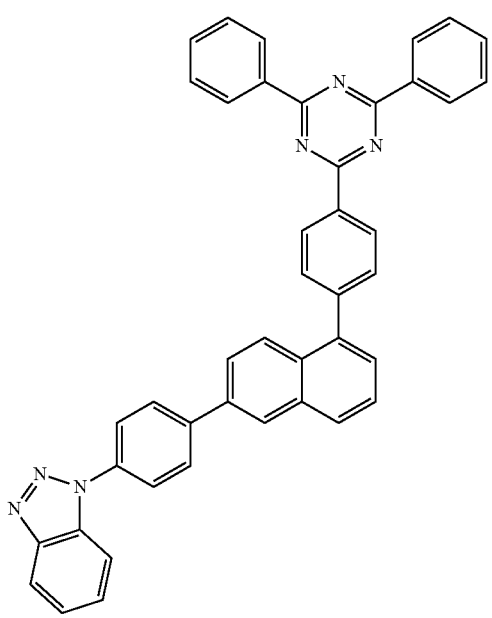

Chemical Formula 3-b-25
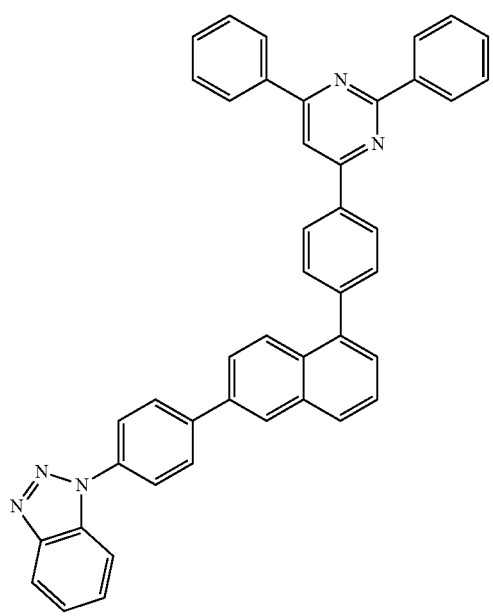
Chemical Formula 3-b-26
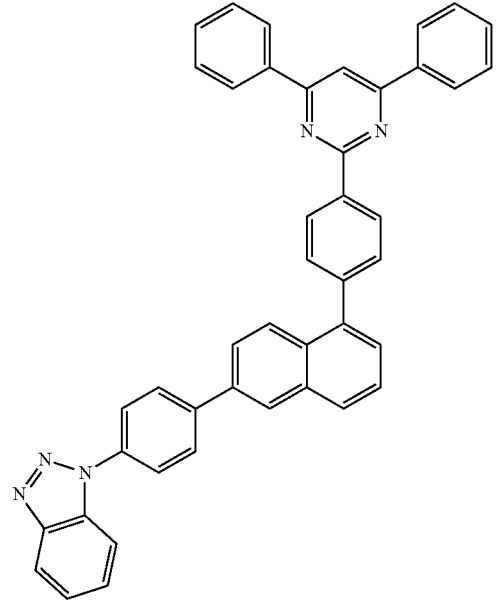
In one embodiment of the present specification, the compound represented by Chemical Formula 1-4 is represented by any one of the following Chemical Formulae 4-a-1 to 4-a-14, and 4-b-1 to 4-b-26.
Chemical Formula 4-a-1
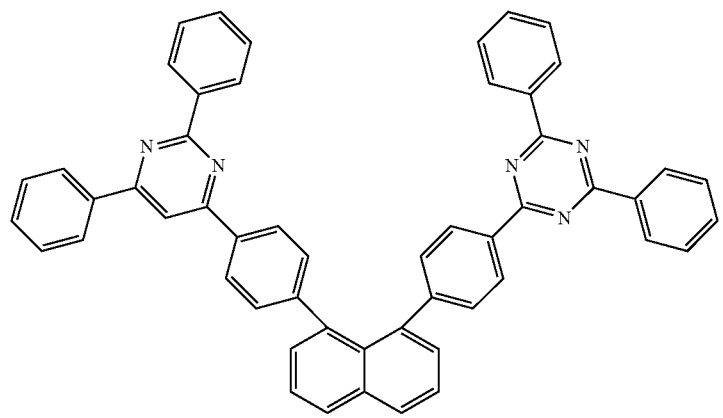
Chemical Formula 4-a-2
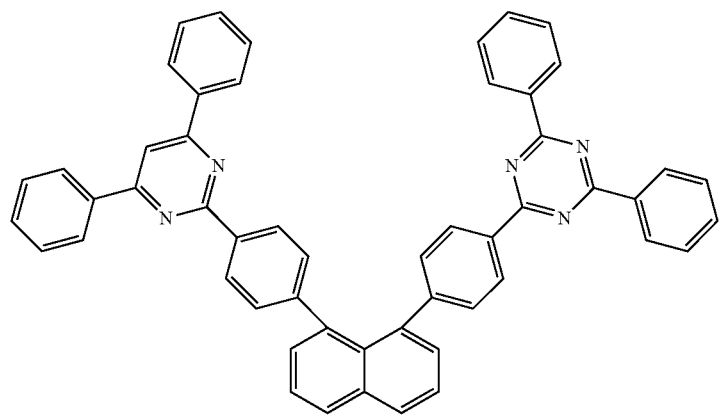

Chemical Formula 4-a-3
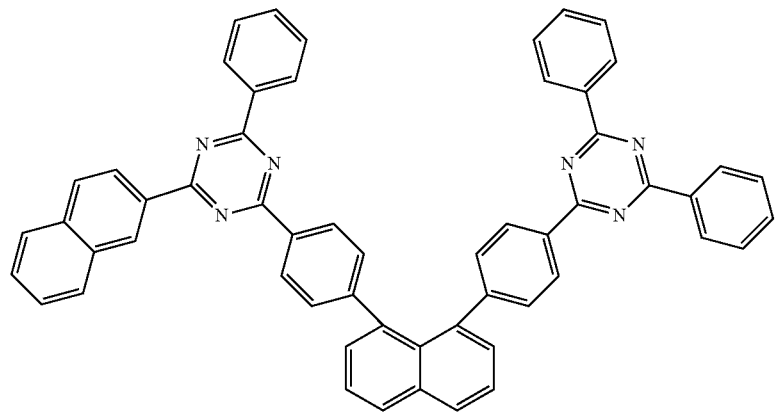
Chemical Formula 4-a-4
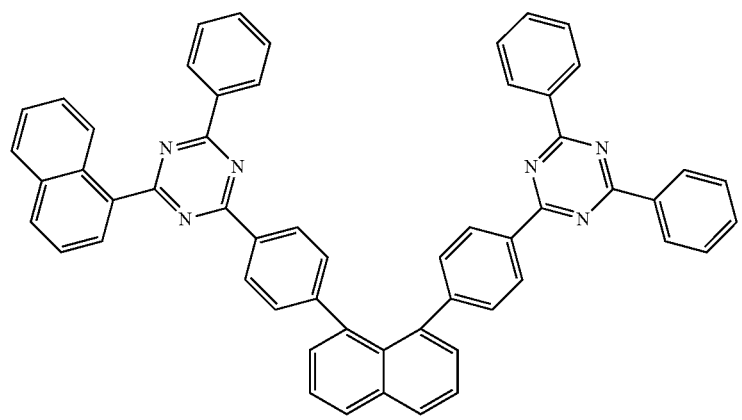
Chemical Formula 4-a-5
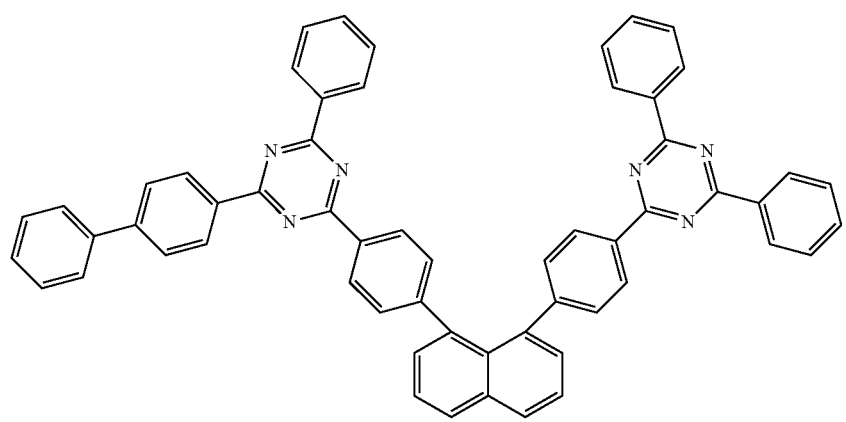

Chemical Formula 4-a-6
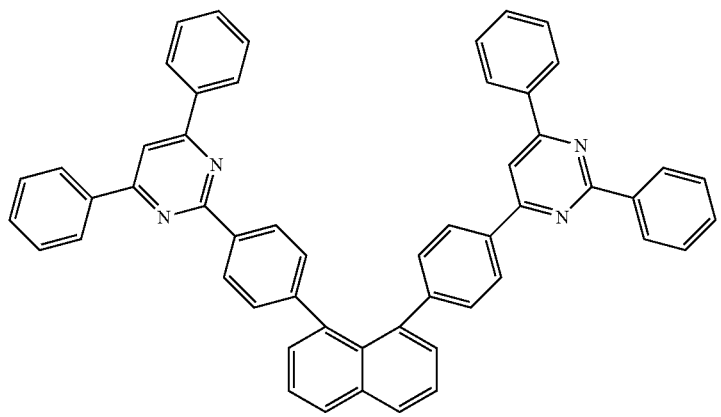
Chemical Formula 4-a-7
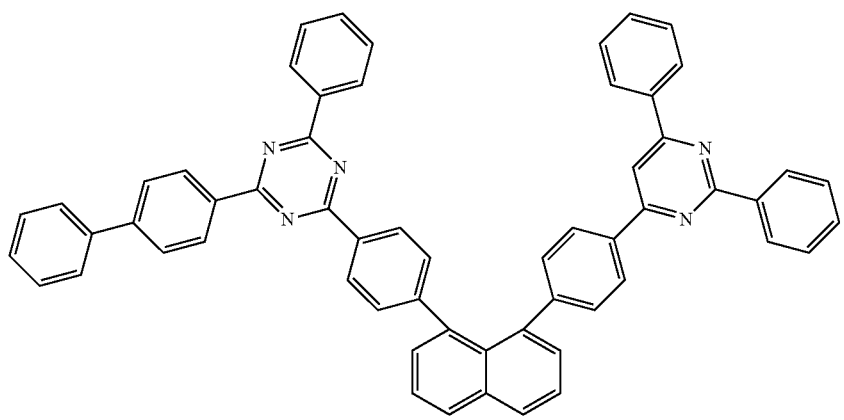
Chemical Formula 4-a-8
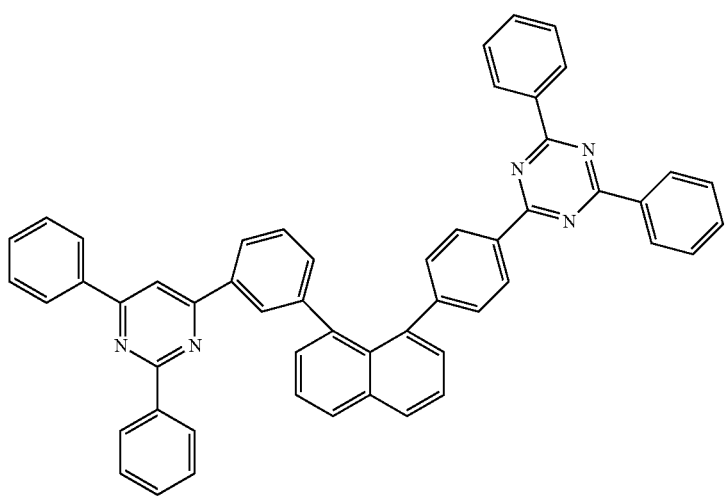

Chemical Formula 4-a-9
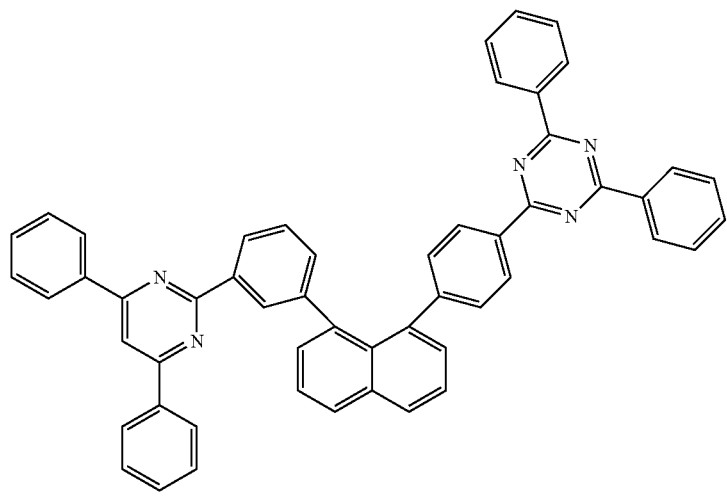
Chemical Formula 4-a-10
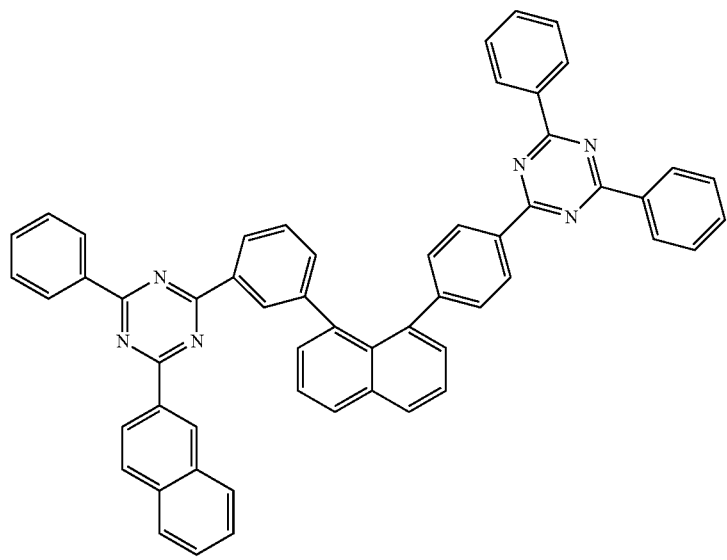
Chemical Formula 4-a-11
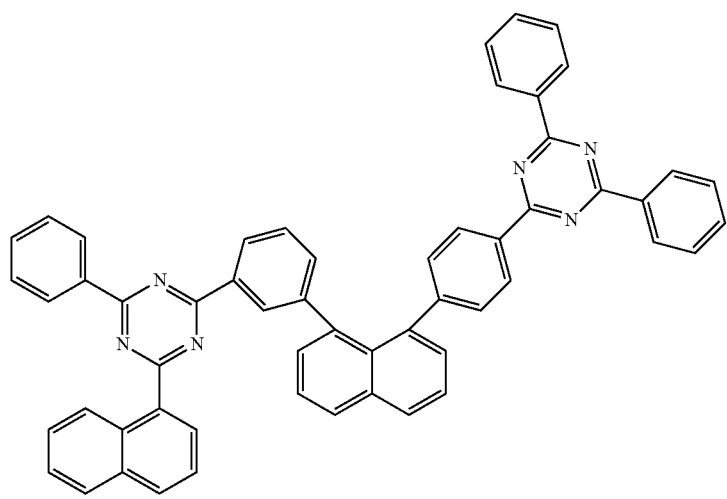

Chemical Formula 4-a-12
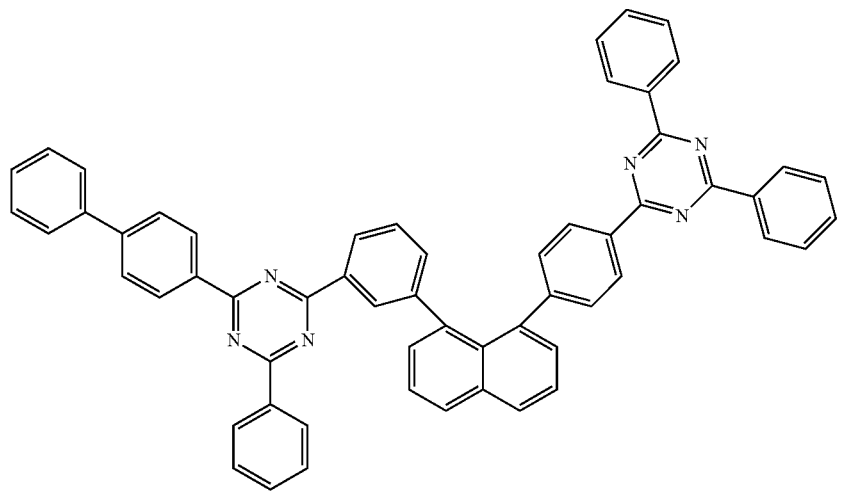
Chemical Formula 4-a-13
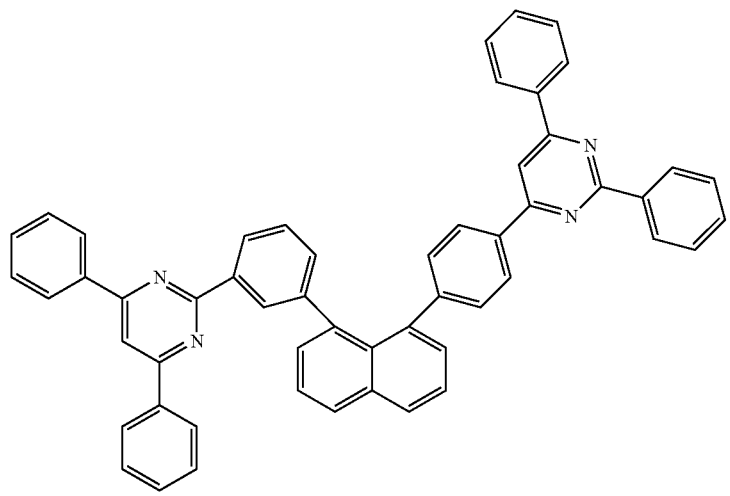
Chemical Formula 4-a-14
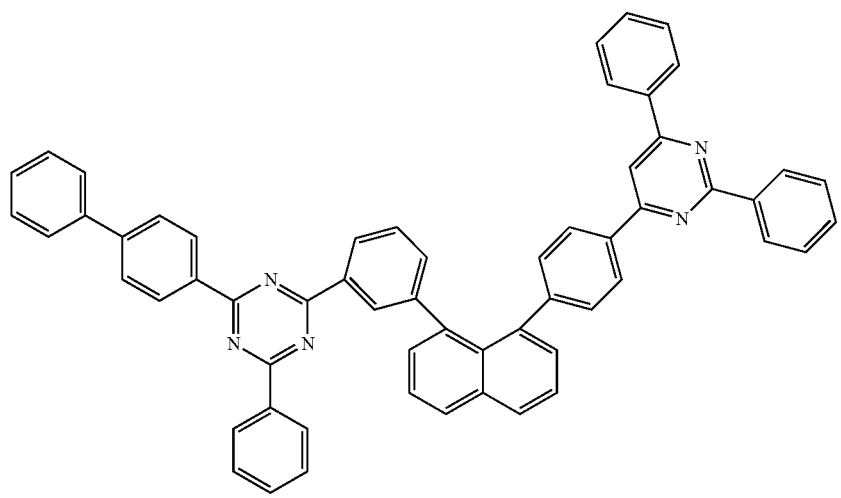

-continued
Chemical Formula 4-b-1
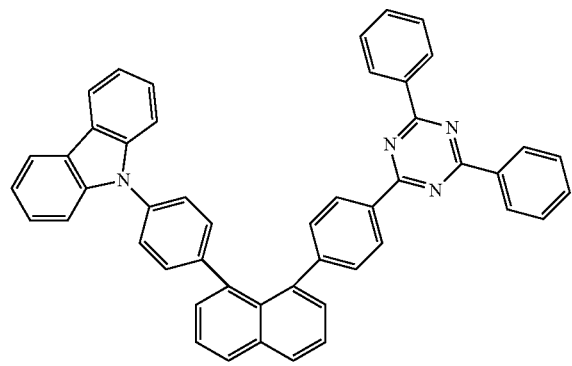
Chemical Formula 4-b-2
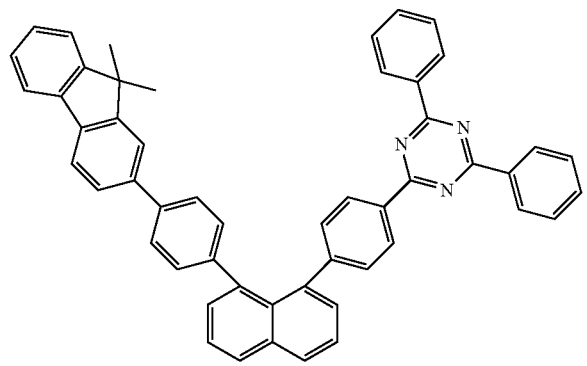
Chemical Formula 4-b-3
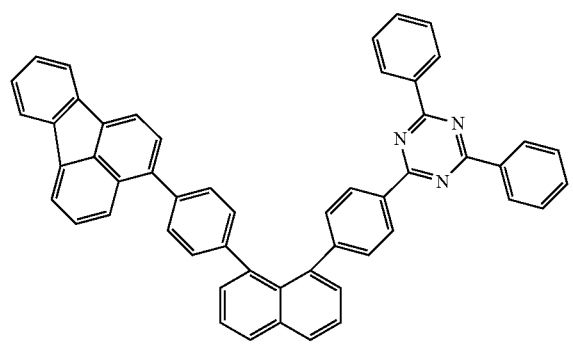
Chemical Formula 4-b-4
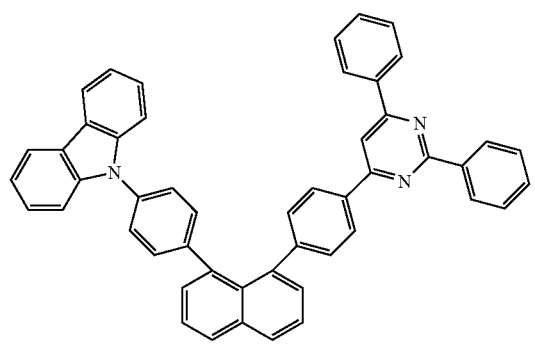
Chemical Formula 4-b-5
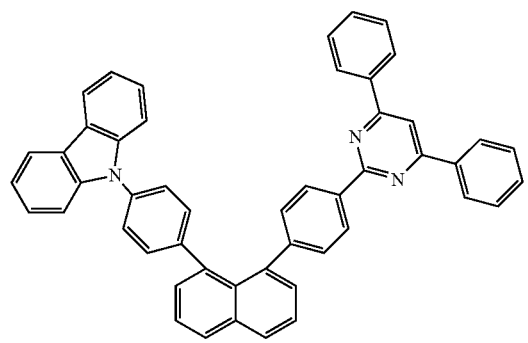
Chemical Formula 4-b-6
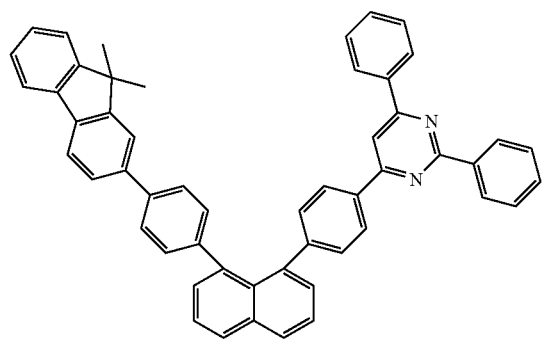
Chemical Formula 4-b-7
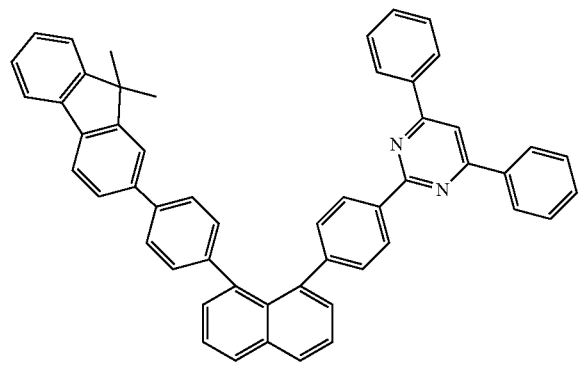
Chemical Formula 4-b-8
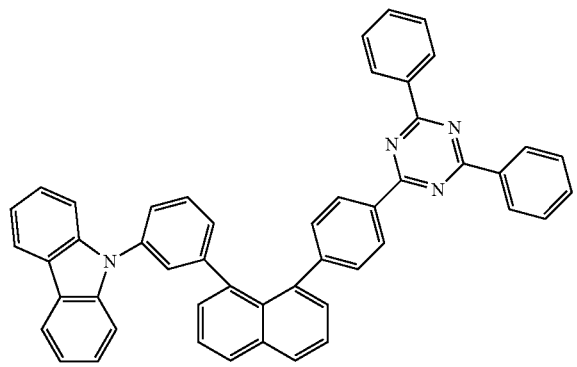

Chemical Formula 4-b-9
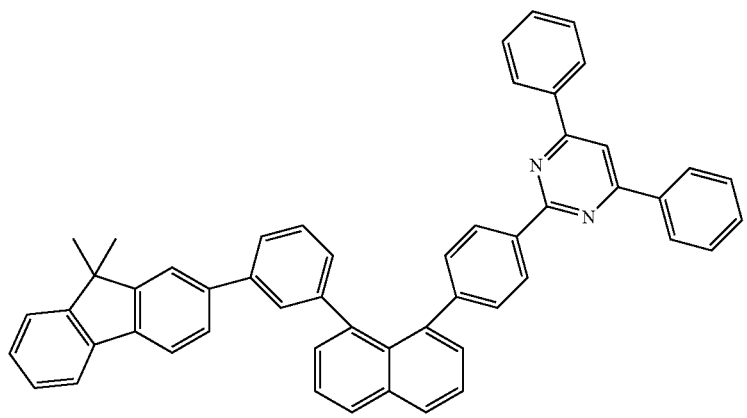
Chemical Formula 4-b-10
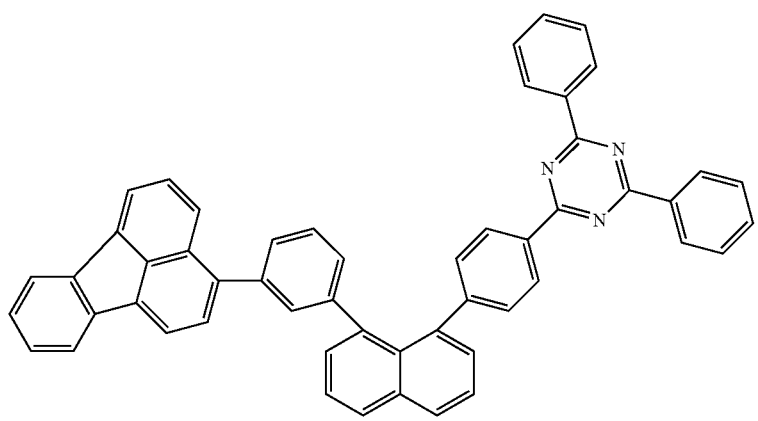
Chemical Formula 4-b-11                                   Chemical Formula 4-b-12
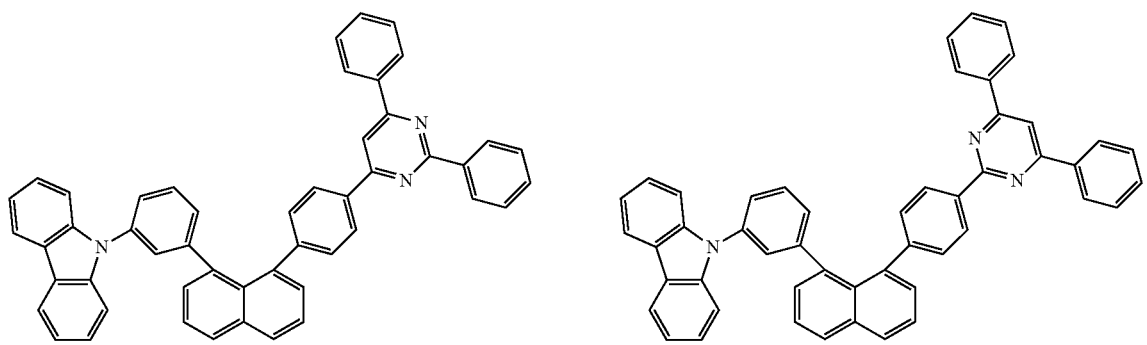
Chemical Formula 4-b-13
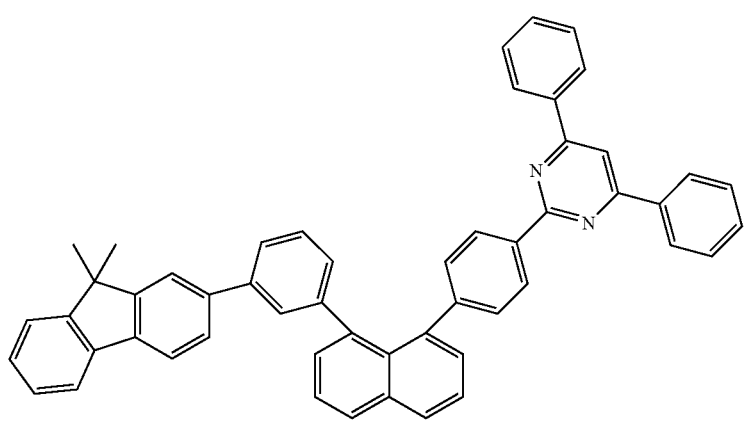

-continued
Chemical Formula 4-b-14
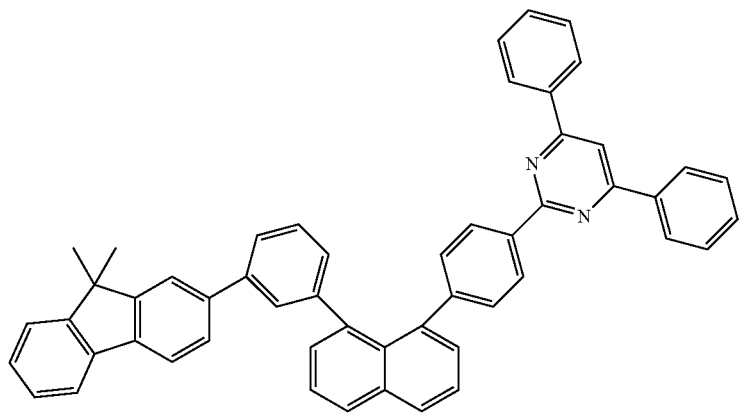
Chemical Formula 4-b-15
Chemical Formula 4-b-16
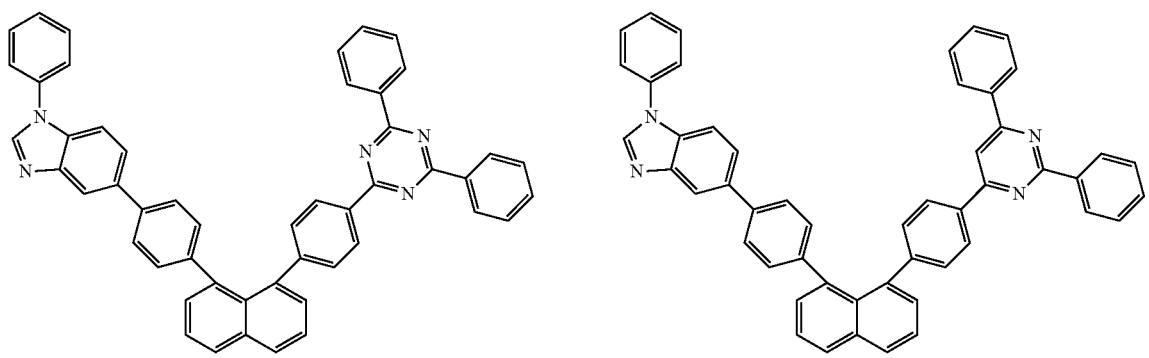
Chemical Formula 4-b-17
Chemical Formula 4-b-18
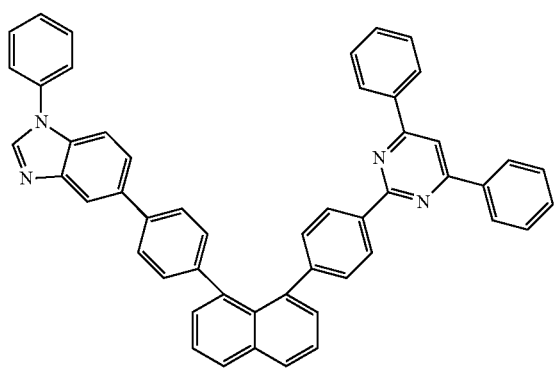
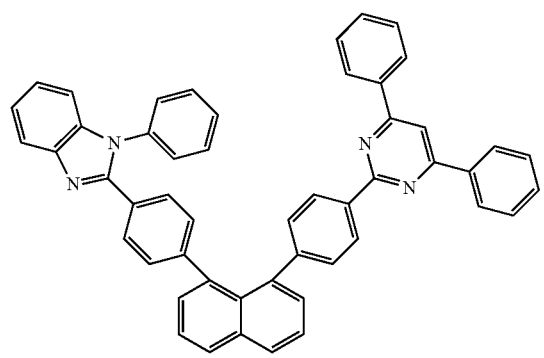
Chemical Formula 4-b-19
Chemical Formula 4-b-20
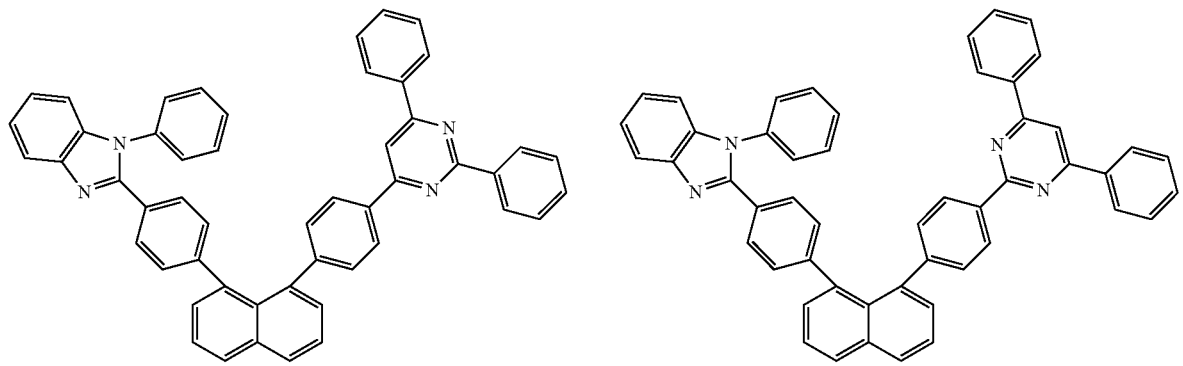

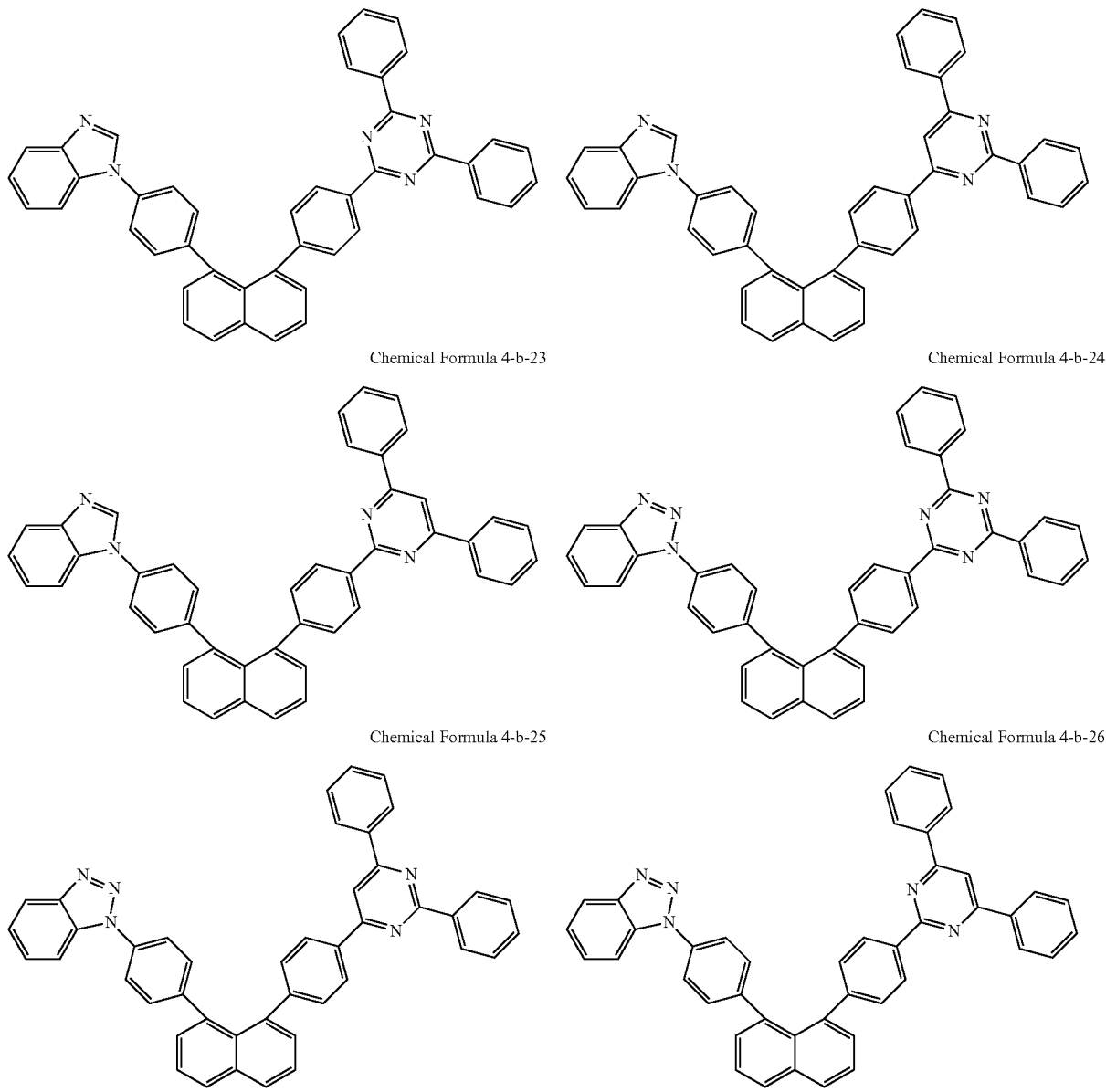

The compound of Chemical Formula 1 can have suitable characteristics for use as an organic material layer used in an organic light emitting device, by introducing substituents having different heterorings on both sides with a naphthalene group as the center, as shown in Chemical Formula 1.

The compound represented by Chemical Formula 1 includes a hetero-cyclic compound including at least one or more of X1 to X3. Therefore, the compound represented by Chemical Formula 1 includes a hetero-cyclic structure thereby has a suitable energy level as an electron injection and/or an electron transfer material in an organic light emitting device. In addition, a device having low driving voltage and high light efficiency can be accomplished by selecting the compounds having a suitable energy level depending on the substituents from among the compounds represented by Chemical Formula 1 in the present specification, and using them in the organic light emitting device.

In addition, by introducing various substituents to the core structure, the energy band gap can be finely adjusted, and meanwhile, characteristics at the surface between organic materials can be improved. Therefore, applications of the material can be diverse.

Meanwhile, the compound of Chemical Formula 1 has a high glass transition temperature (Tg) thereby has excellent thermal stability. Such a thermal stability improvement becomes an important factor that provides a driving stability to a device.

The compound represented by Chemical Formula 1 may be prepared based on the preparation examples described later.

The compound represented by Chemical Formula 1 may be prepared using a method in which a structure, in which a heterocyclic ring including X1 to X3 is substituted with Ar2, Ar3 and L1, is bonded to a structure, in which a naphthyl group is substituted with substituted Chemical Formula 2; a substituted or unsubstituted aryl group; or a substituted or unsubstituted heteroring group including one or more of O, N and S as a heteroatom.

The hetero-cyclic compound represented by Chemical Formula 1 in addition to Chemical Formulae 1-1 to 1-4 may be prepared by modifying the number of heteroatoms in X1 to X3, Ar2, Ar3 and Lx.

In Lx, x is an integer of 1 or 2.

In addition, the present specification provides an organic light emitting device that includes the hetero-cyclic compound represented by Chemical Formula 1.

In one embodiment of the present specification, an organic light emitting device that includes a first electrode; a second electrode provided opposite to the first electrode; and one or more layers of organic material layers provided between the first electrode and the second electrode, wherein one or more layers of the organic material layers include the hetero-cyclic compound.

The organic material layer of the organic light emitting device in the present specification may be formed as a monolayer structure, but may also be formed as a multilayer structure in which two or more layers of the organic material layers are laminated. For example, the organic light emitting device of the present invention may have a structure that includes a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the organic material layer includes a hole injection layer or a hole transfer layer, and the hole injection layer or the hole transfer layer includes the hetero-cyclic compound.

In another embodiment, the organic material layer includes a light emitting layer, and the light emitting layer includes the hetero-cyclic compound as the host of the light emitting layer.

In one embodiment of the present specification, the organic material layer includes an electron transfer layer or an electron injection layer, and the electron transfer layer or the electron injection layer includes the hetero-cyclic compound.

In one embodiment of the present specification, the electron transfer layer, the electron injection layer, or the layer simultaneously performing electron transfer and electron injection includes only the hetero-cyclic compound.

In one embodiment of the present specification, the organic material layer further includes a hole injection layer or a hole transfer layer including a compound that includes an arylamino group, a carbazole group or a benzocarbazole group, in addition to the organic material layer including the hetero-cyclic compound.

In one embodiment of the present specification, the organic material layer including the hetero-cyclic compound includes the hetero-cyclic compound as a host, and other organic compounds, metals or metal compounds as a dopant.

In another embodiment, the organic light emitting device may be an organic light emitting device having a normal type structure in which an anode, one or more layers of organic material layers and a cathode are laminated on a substrate in consecutive order.

In another embodiment, the organic light emitting device may be an organic light emitting device having an inverted type structure in which a cathode, one or more layers of organic material layers and an anode are laminated on a substrate in consecutive order.

For example, the structure of an organic light emitting device according to one embodiment of the present specification is illustrated in FIGS. 1 and 2.

FIG. 1 illustrates the structure of an organic electronic device in which a substrate (1), an anode (2), a light emitting layer (3) and a cathode (4) are laminated in consecutive order. In the structure such as this, the hetero-cyclic compound may be included in the light emitting layer (3).

FIG. 2 illustrates the structure of an organic electronic device in which a substrate (1), an anode (2), a hole injection layer (5), a hole transfer layer (6), a light emitting layer (3), an electron transfer layer (7) and a cathode (4) are laminated in consecutive order. In the structure such as this, the hetero-cyclic compound may be included in one or more layers of the hole injection layer (5), the hole transfer layer (6), the light emitting layer (3) and the electron transfer layer (7).

In the structure such as this, the compound may be included in one or more layers of the hole injection layer, the hole transfer layer, the light emitting layer and the electron transfer layer.

The organic light emitting device of the present specification may be prepared using materials and methods known in the related art, except that one or more layers of organic material layers include the compound of the present specification, that is, the hetero-cyclic compound.

When the organic light emitting device includes multiple numbers of organic material layers, the organic material layer may be formed with identical materials or different materials.

The organic light emitting device of the present specification may be prepared using materials and methods known in the related art, except that one or more layers of organic material layers includes the hetero-cyclic compound, that is, the compound represented by Chemical Formula 1.

For example, the organic light emitting device of the present specification may be prepared by laminating a first electrode, an organic material layer and a second electrode on a substrate in consecutive order. At this time, using a physical vapor deposition (PVD) method such as a sputtering method or an e-beam evaporation method, the anode is formed by depositing a metal, a metal oxide having conductivity, or alloys thereof on the substrate, and after the organic material layer including a hole injection layer, a hole transfer layer, a light emitting layer and an electron transfer layer is formed thereon, a material that can be used as the cathode is deposited thereon, and as a result, the organic light emitting device may be prepared. In addition to this method, the organic light emitting device may be prepared by depositing a cathode material, an organic material layer and an anode material on a substrate in consecutive order.

In addition, when the organic light emitting device is prepared, the compound of Chemical Formula 1 may be formed as an organic material layer using a solution coating method as well as a vacuum deposition method. Herein, the solution coating method means spin coating, dip coating, doctor blading, ink jet printing, screen printing, a spray method, roll coating or the like, but is not limited thereto.

In addition to these methods, the organic light emitting device may also be prepared by depositing a cathode material, an organic material layer and an anode material on a substrate in consecutive order (PCT Publication No. 2003/012890). However, the preparation method is not limited thereto.

In one embodiment of the present specification, the first electrode is an anode, and the second electrode is a cathode.

In another embodiment, the first electrode is a cathode, and the second electrode is an anode.

As the anode material, a material having large work function is normally preferable so that hole injection to the organic material layer is smooth. Specific examples of the anode material that can be used in the present invention include metals such as vanadium, chromium, copper, zinc or gold, and alloys thereof; metal oxides such as zinc oxides, indium oxides, indium tin oxides (ITO) or indium zinc oxide (IZO); and mixtures of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, or the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and load, or alloys thereof; multilayer structure materials such as LiF/Al or $LiO_2$/Al, or the like, but are not limited thereto.

The hole injection layer is a layer that injects holes from an electrode, and a hole injection material is preferably a compound that has an ability to transfer the holes, has a hole injection effect in an anode and has an excellent hole injection effect for a light emitting layer or a light emitting material, prevents the movement of excitons generated in the light emitting layer to an electron injection layer or an electron injection material, and in addition, has excellent thin film forming ability. The highest occupied molecular orbital (HOMO) of the hole injection material is preferably between the work function of an anode and the HOMO of surrounding organic material layers. Specific examples of the hole injection material include a metal porphyrin, oligothiophene, an arylamine-based organic material, a hexanitrile hexaazatriphenylene-based organic material, a quinacridone-based organic material, a perylene-based organic material, anthraquinone, and a polyaniline- and polythiophene-based conductive polymer, or the like, but are not limited thereto.

The hole transfer layer is a layer that receives holes from a hole injection layer and transfers the holes to a light emitting layer, and as the hole transfer material, a material that can receive the holes from an anode or a hole injection layer, move the holes to a light emitting layer, and has high mobility for the holes is suitable. Specific examples thereof include an arylamine-based organic material, a conductive polymer, a block copolymer having conjugated parts and non-conjugated parts together, or the like, but are not limited thereto.

The light emitting material is a material that can emit light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene or the like, but are not limited thereto.

The light emitting layer may include a host material and a dopant material. The host material includes a condensed aromatic ring derivative, a heteroring-containing compound, or the like. Specifically, the condensed aromatic ring derivative includes an anthracene derivative, a pyrene derivative, a naphthalene derivative, a pentacene derivative, a phenanthrene compound, a fluoranthene compound or the like, and the heteroring-containing compound includes a carbazole derivative, a dibenzofuran derivative, a ladder-type furan compound, a pyrimidine derivative or the like, but are not limited thereto.

The dopant material includes an aromatic amine derivative, a styrylamine compound, a boron complex, a fluoranthene compound, a metal complex, or the like. Specifically, the aromatic amine derivative includes arylamino-including pyrene, anthracene, crycene and periflanthene as the condensed aromatic ring derivative having a substituted or unsubstituted arylamino group, and the styrylamine compound includes a compound in which a substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material that can receive the electrons from a cathode, move the electrons to a light emitting layer, and has high mobility for the electrons is suitable. Specific examples thereof include an Al complex of 8-hydroxyquinoline; a complex including Alq3; an organic radical compound; a hydroxyflavone-metal complex or the like, but are not limited thereto. The electron transfer layer can be used together with any desired cathode material as is used according to technologies in the related art. Particularly, examples of the suitable cathode material are common materials that have small work function, and in which an aluminum layer or a silver layer follows. Specifically the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer the electrons, has an electron injection effect in a cathode and has an excellent electron injection effect for a light emitting layer or a light emitting material, prevents the movement of excitons generated in the light emitting layer to the electron injection layer, and in addition, has excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, or the like, but are not limited thereto.

The metal complex compound may include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]

quinolinato)berylium, bis(10-hydroxybenzo[h]quinolinato) zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium or the like, but is not limited thereto.

The organic light emitting device according to the present specification may be a top-emission type, a bottom-emission type or a dual-emission type depending on the materials used.

In one embodiment of the present specification, the hetero-cyclic compound may be included in an organic solar cell or an organic transistor in addition to an organic light emitting device.

Hereinafter, the hetero-cyclic compound represented by Chemical Formula 1 and the manufacture of an organic light emitting device including the same will be described in detail with reference to examples. However, the following examples are for the illustrative purposes only, and the scope of the present specification is not limited thereto.

EXAMPLE

Hereinafter, the present invention will be described in more detail with reference to preparation examples and experimental examples, however, the scope of the present invention is not limited to the following preparation examples and the experimental examples.

Preparation Example

<Preparation Example 1> Preparation of the Following Compound 1-a-1

1) Synthesis of the Following Compound 1-A

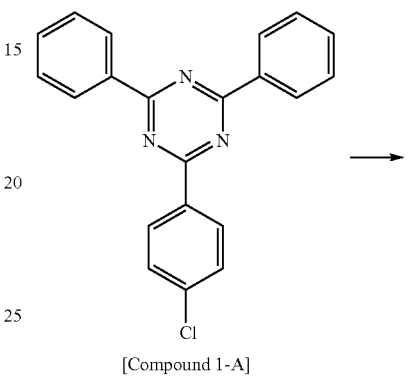

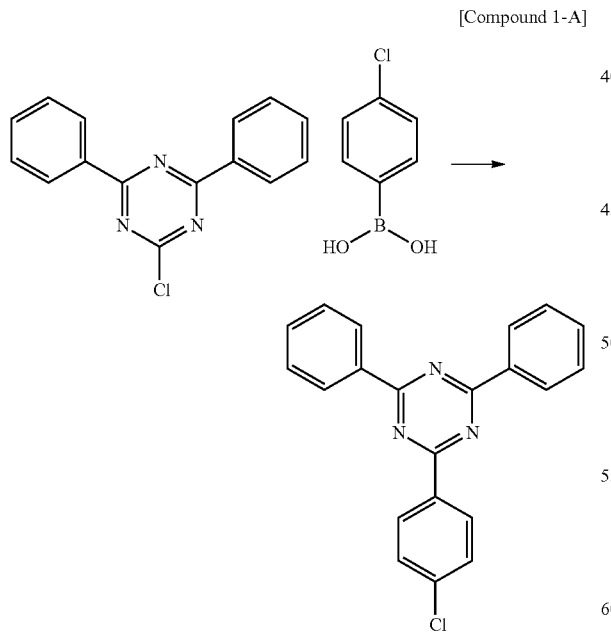

After the 2-chloro-4,6-diphenyl-1,3,5-triazine compound (37.1 g, 0.14 mol) and 4-chlorophenylboronic acid (23.8 g, 0.15 mol) were completely dissolved in 150 ml of tetrahydrofuran under nitrogen atmosphere, a 2M aqueous potassium carbonate solution (80 ml) was added thereto, and after tetrakis-(triphenylphosphine)palladium (3.2 g, 2.7 mmol) was added thereto, the mixture was stirred with heating for 5 hours. The temperature was lowered to room temperature, and the water layer was removed. The result was dried with anhydrous magnesium sulfate, concentrated under vacuum, then passed through a column using tetrahydrofuran:hexane=1:6, and Compound 1-A (34 g, yield: 72%) was prepared.

MS [M+H]$^+$=344

2) Synthesis of the Following Compound 1-B

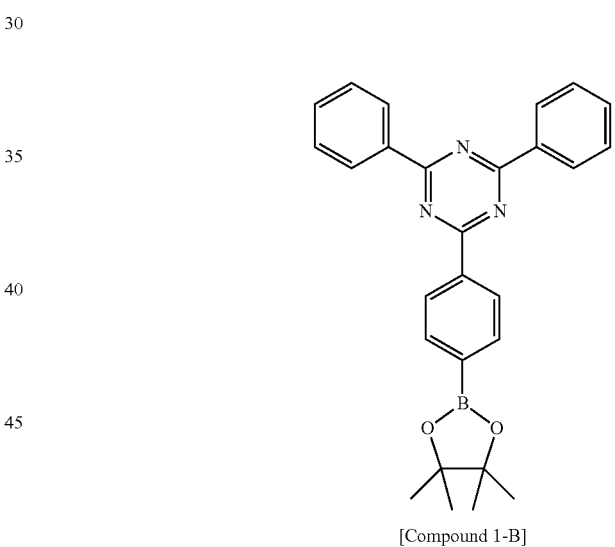

Under nitrogen atmosphere, Compound 1-A (34 g, 98.9 mmol), bis(pinacolato)diboron (27.6 g, 108 mmol) and potassium acetate (29.1 g, 296 mmol) were mixed, added to 100 ml of dioxane, and the mixture was heated while stirring. Under reflux, bis(dibenzylideneacetone)palladium (1.7 g, 2.94 mmol) and tricyciohexylphosphine (1.6 g, 5.9 mmol) were added thereto, and the result was heated and stirred for 10 hours. After the reaction completed, the temperature was lowered to room temperature, and the result was filtered. The filtrate was poured to water, extracted with chloroform, and the organic layer was dried using anhydrous magnesium sulfate. The result was vacuum distilled, recrystallized with ethanol, and Compound 1-B (35 g, yield: 81%) was prepared.

MS [M+H]$^+$=436

3) Synthesis of the Following Compound 1-C

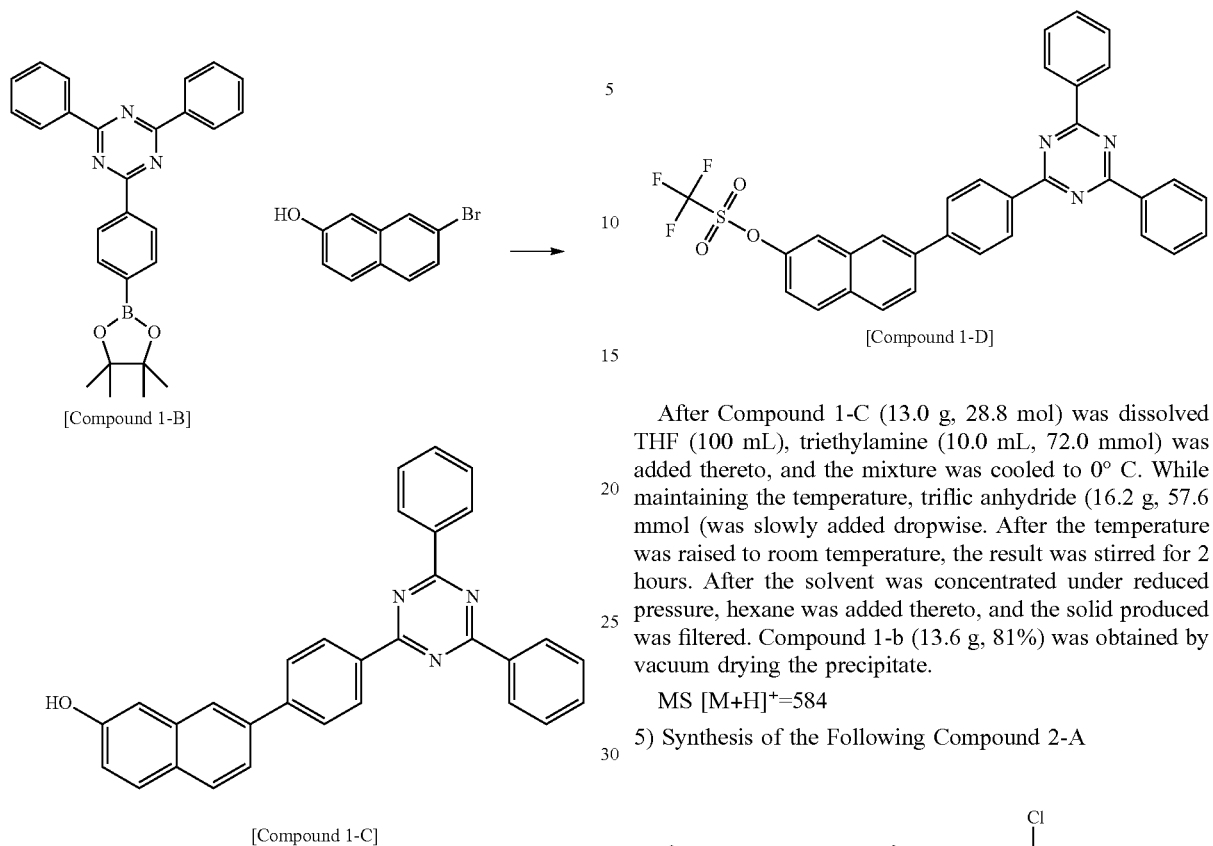

[Compound 1-B]

[Compound 1-C]

After Compound 1-B (14.5 g, 33.3 mmol) and 7-bromonaphthalen-2-ol (7.4 g, 33.3 mmol) were completely dissolved in 100 ml of tetrahydrofuran, 60 ml of a 2M aqueous potassium carbonate solution, and tetrakistriphenyl-phosphinopalladium (769 mg, 0.67 mmol) were added thereto, and then the mixture was stirred with heating for 3 hours. After the temperature was lowered to room temperature and the reaction completed, the potassium carbonate solution was removed and the yellow solid was filtered. The filtered yellow solid was washed once with tetrahydrofuran and once with ethanol, and Compound 1-C (13.2 g, yield: 88%) was prepared.

MS [M+H]$^+$=452

4) Synthesis of the Following Compound 1-D

[Compound 1-C]

[Compound 1-D]

After Compound 1-C (13.0 g, 28.8 mol) was dissolved THF (100 mL), triethylamine (10.0 mL, 72.0 mmol) was added thereto, and the mixture was cooled to 0° C. While maintaining the temperature, triflic anhydride (16.2 g, 57.6 mmol (was slowly added dropwise. After the temperature was raised to room temperature, the result was stirred for 2 hours. After the solvent was concentrated under reduced pressure, hexane was added thereto, and the solid produced was filtered. Compound 1-b (13.6 g, 81%) was obtained by vacuum drying the precipitate.

MS [M+H]$^+$=584

5) Synthesis of the Following Compound 2-A

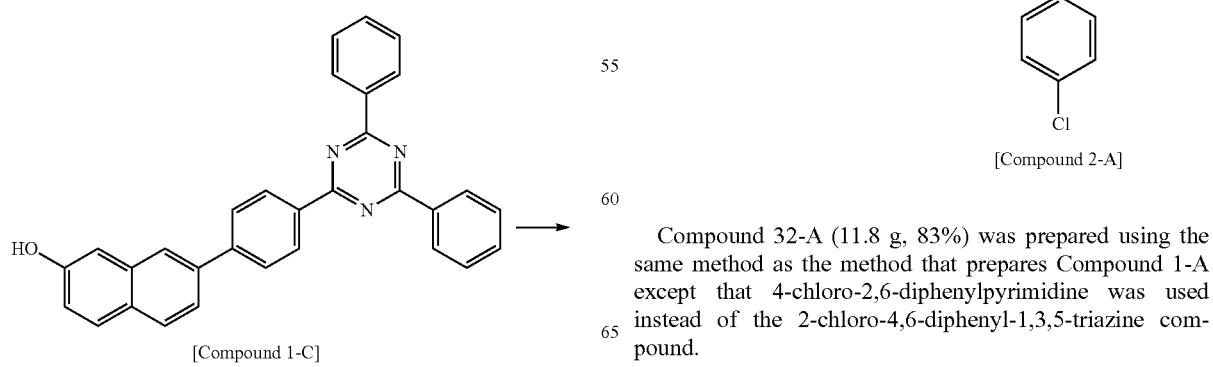

[Compound 2-A]

Compound 32-A (11.8 g, 83%) was prepared using the same method as the method that prepares Compound 1-A except that 4-chloro-2,6-diphenylpyrimidine was used instead of the 2-chloro-4,6-diphenyl-1,3,5-triazine compound.

MS [M+H]$^+$=343

6) Synthesis of the Following Compound 2-B
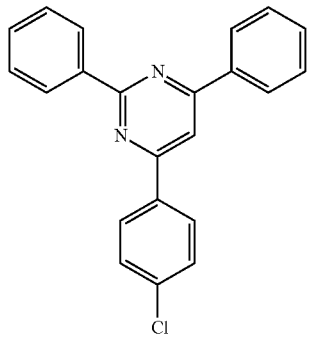
[Compound 2-A]
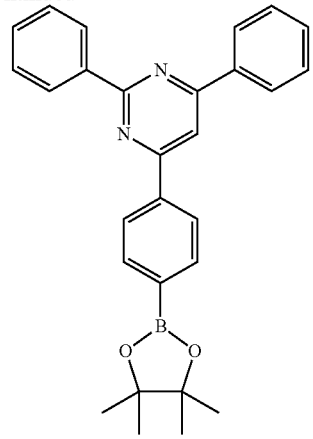
[Compound 2-B]
Compound 2-B (21.7 g, 89%) was prepared using the same method as the method that prepares Compound 1-B except that Compound 2-A was used instead of Compound 1-A.
MS [M+H]$^+$=435
7) Synthesis of the Following Compound 1-a-1
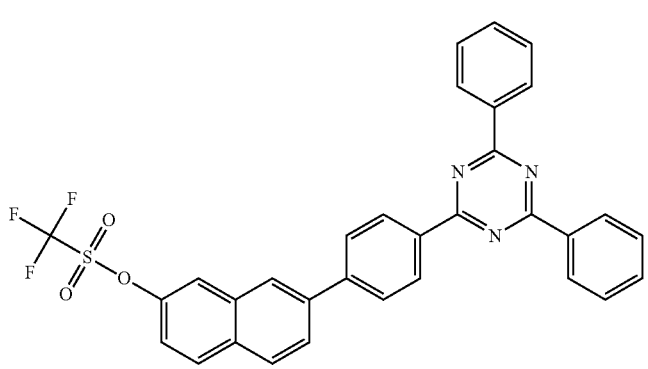
[Compound 1-D]
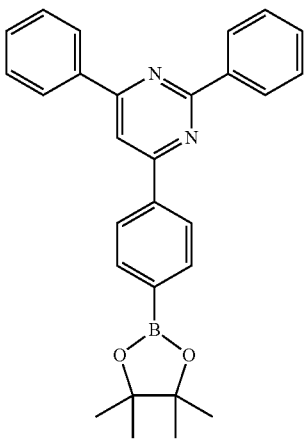
[Compound 2-B]
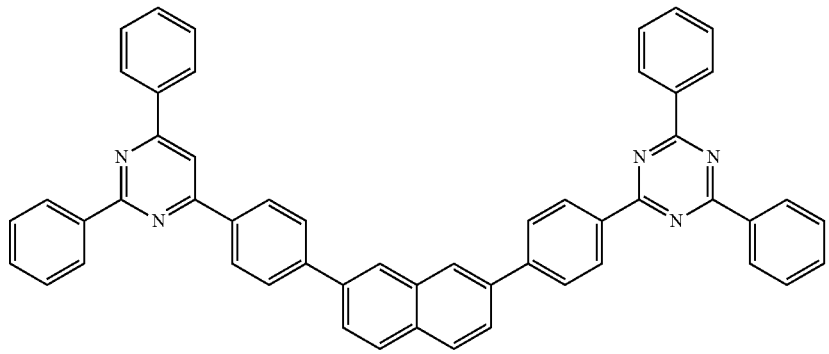
[Compound 1-a-1]

After Compound 1-D (11.2 g, 19.2 mmol) and Compound 2-B (9.2 g, 21.1 mmol) were completely dissolved in 60 ml of tetrahydrofuran, 40 ml of a 2M aqueous potassium carbonate solution, and tetrakistriphenyl-phosphinopalladium (443 mg, 0.38 mmol) were added thereto, and the mixture was stirred with heating for 3 hours. After the temperature was lowered to room temperature and the reaction completed, the potassium carbonate solution was removed and the white solid was filtered. The filtered white solid was washed once with tetrahydrofuran and once with ethanol, and Compound 1-a-1 (11.3 g, yield: 80%) was prepared.

MS [M+H]$^+$=742

<Preparation Example 2> Preparation of the Following Compound 1-a-2

1) Synthesis of the Following Compound 3-A

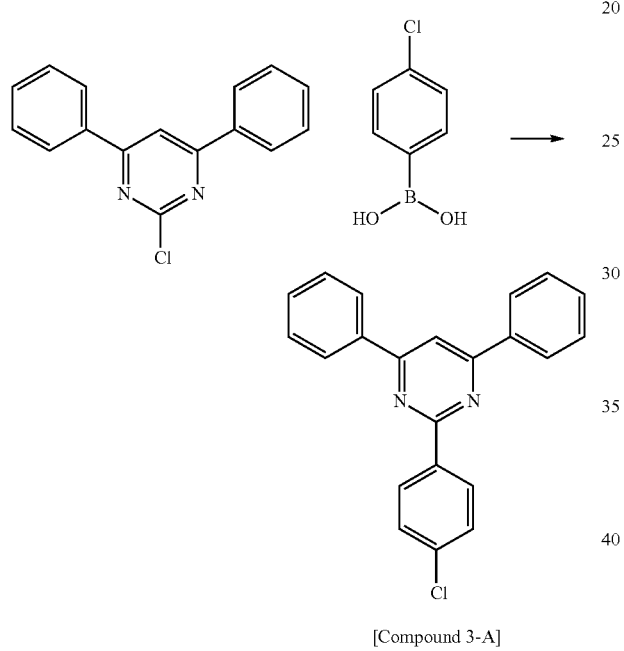

[Compound 3-A]

Compound 3-A (17.3 g, 83%) was prepared using the same method as the method that prepares Compound 1-A except that 2-chloro-4,6-diphenylpyrimidine was used instead of the 2-chloro-4,6-diphenyl-1,3,5-triazine compound.

MS [M+H]$^+$=343

2) Synthesis of the Following Compound 3-B

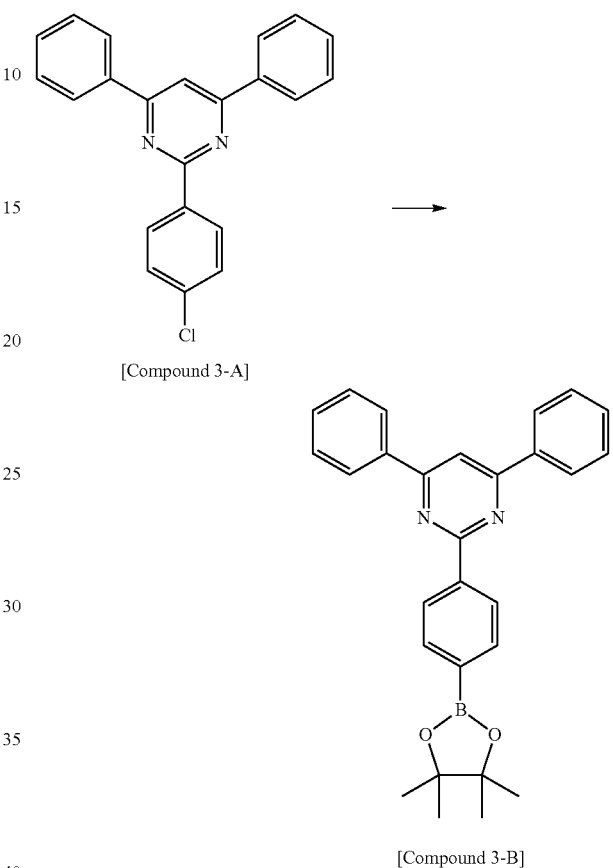

[Compound 3-A]

[Compound 3-B]

Compound 3-B (12.9 g, 82%) was prepared using the same method as the method that prepares Compound 1-B except that Compound 3-A was used instead of Compound 1-A.

MS [M+H]$^+$=435

3) Synthesis of the Following Compound 1-a-2

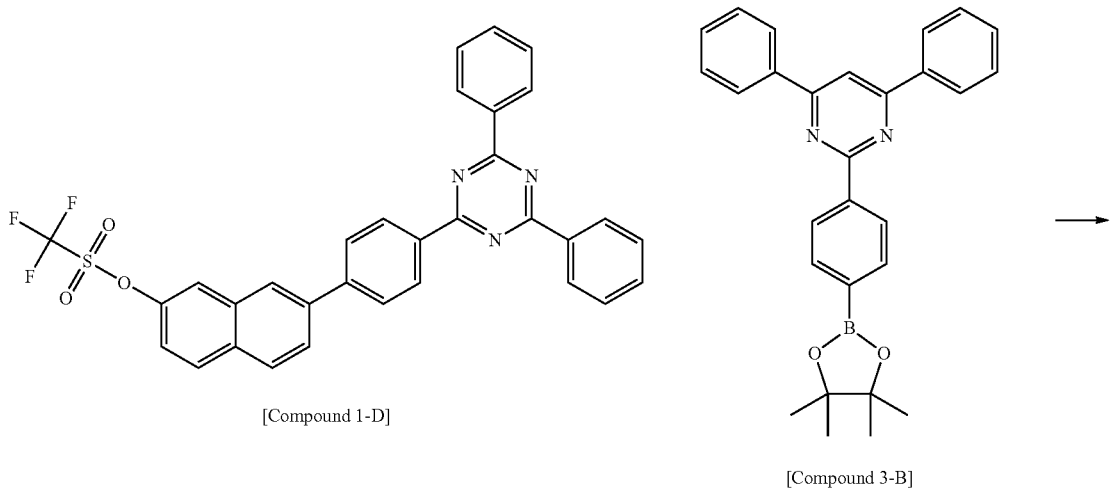

[Compound 1-D]

[Compound 3-B]

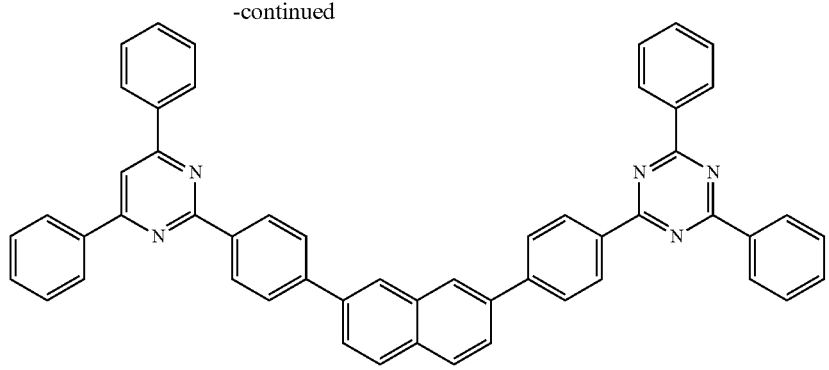

[Compound 1-a-2]

Compound 1-a-2 (11.4 g, 85%) was prepared using the same method as the method that prepares Compound 1-a-1 except that Compound 3-B was used instead of Compound 2-B.

MS [M+H]$^+$=742

<Preparation Example 3> Preparation of the Following Compound 1-a-5

1) Synthesis of the Following Compound 4-A

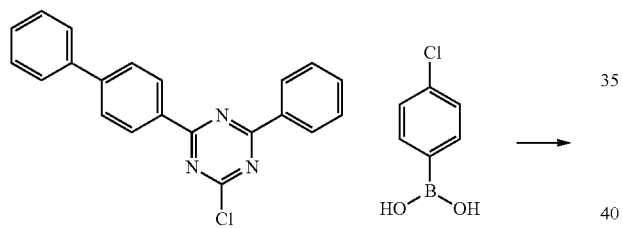

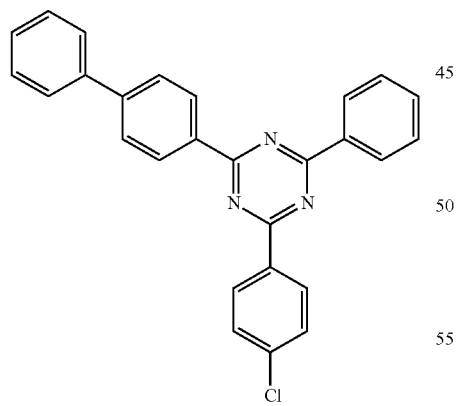

[Compound 4-A]

Compound 4-A (18.8 g, 88%) was prepared using the same method as the method that prepares Compound 1-A except that 2-([1,1'-biphenyl]-4-yl)-4-chloro-6-phenyl-1,3,5-triazine was used instead of the 2-chloro-4,6-diphenyl-1,3,5-triazine compound.

MS [M+H]$^+$=420

2) Synthesis of the Following Compound 4-B

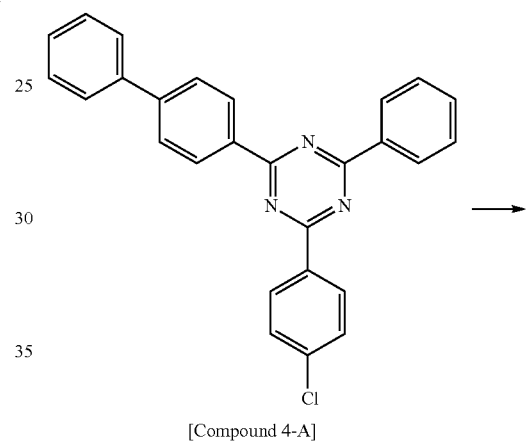

[Compound 4-A]

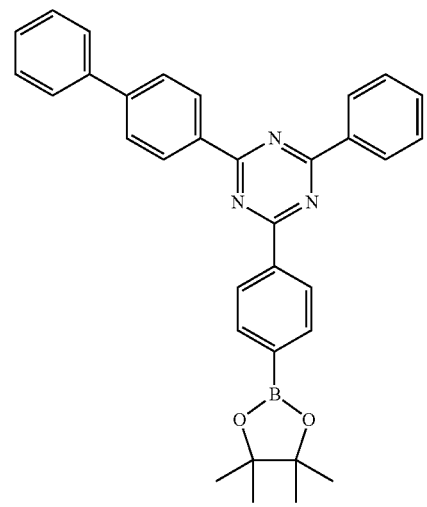

[Compound 4-B]

Compound 4-B (16.5 g, 84%) was prepared using the same method as the method that prepares Compound 1-B except that Compound 4-A was used instead of Compound 1-A.

MS [M+H]$^+$=512

3) Synthesis of the Following Compound 1-a-5
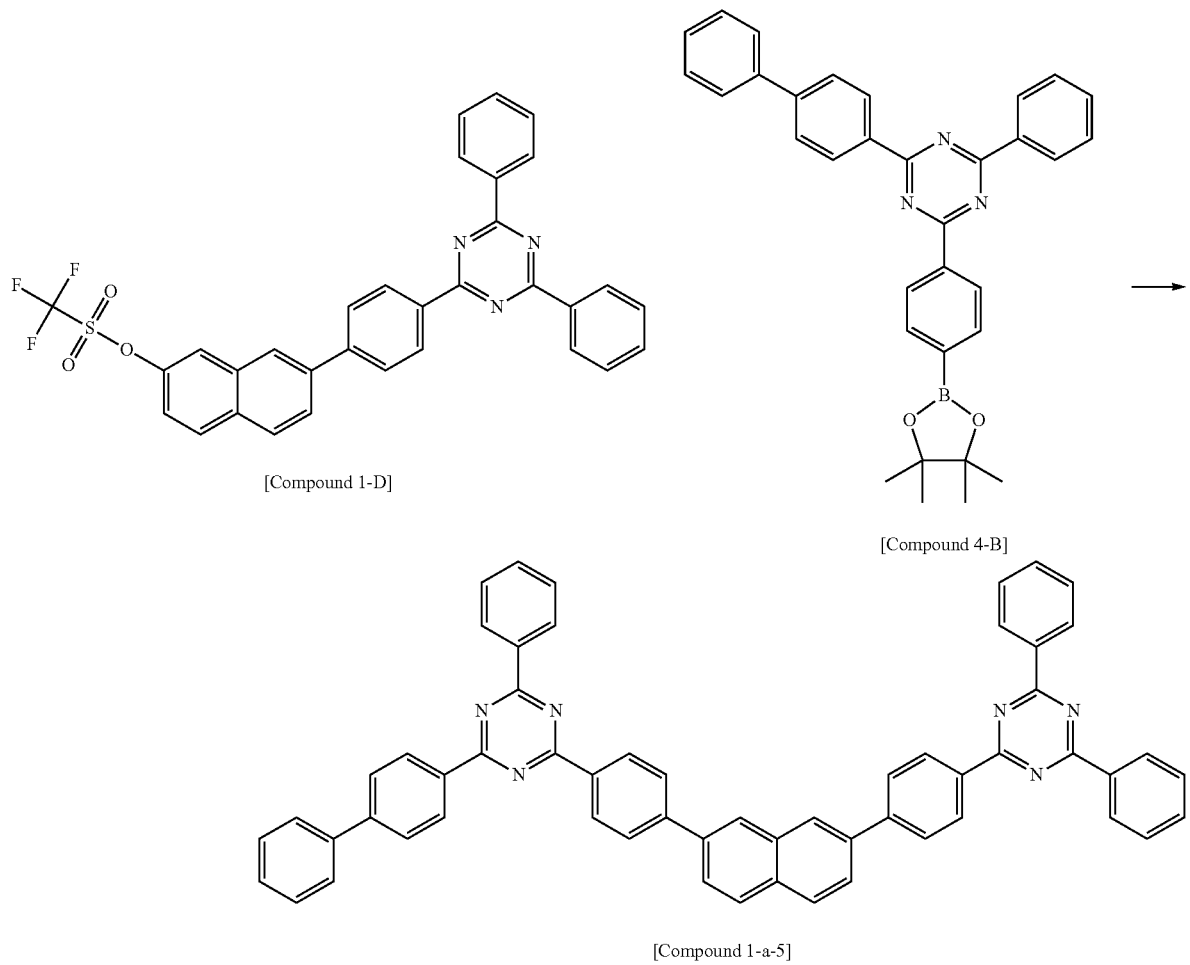
Compound 1-a-5 (12.7 g, 88%) was prepared using the same method as the method that prepares Compound 1-a-1 except that Compound 4-B was used instead of Compound 2-B.
MS [M+H]$^+$=819
<Preparation Example 4> Preparation of the Following Compound 1-b-1
1) Synthesis of the Following Compound 1-b-1
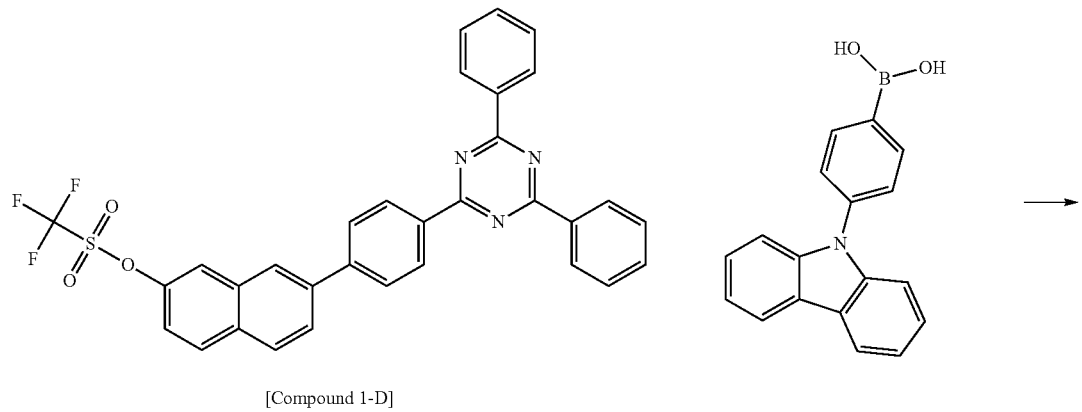

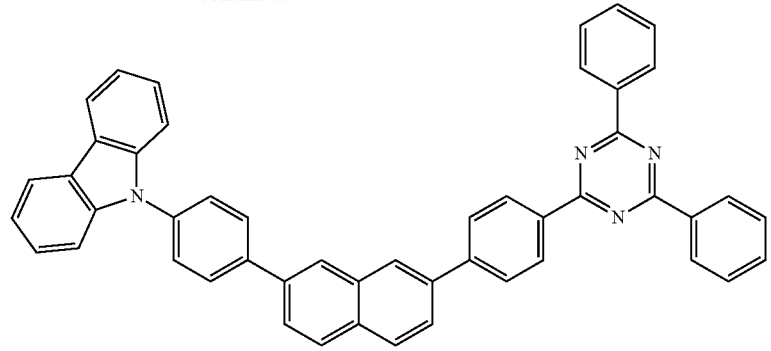
[Compound 1-b-1]
Compound 1-b-1 (13.4 g, 87%) was prepared using the same method as the method that prepares Compound 1-a-1 except that (4-(9H-carbazol-9-yl)phenyl)boronic acid was used instead of Compound 2-B.
MS [M+H]$^+$=677
<Preparation Example 5> Preparation of the Following Compound 1-b-2
1) Synthesis of the Following Compound 1-b-2
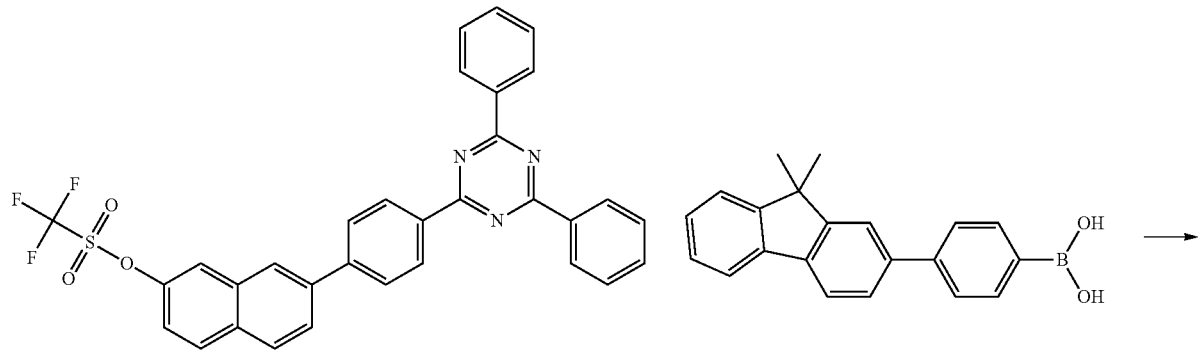
[Compound 1-D]
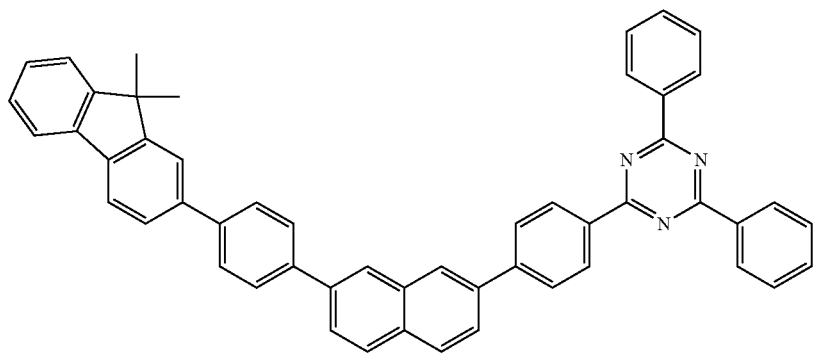
[Compound 1-b-2]

Compound 1-b-2 (9.2 g, 89%) was prepared using the same method as the method that prepares Compound 1-a-1 except that (4-(9,9-dimethyl-9H-fluoren-2-yl)phenyl)boronic acid was used instead of Compound 2-B.

MS [M+H]⁺=704

<Preparation Example 6> Preparation of the Following Compound 2-a-1

1) Synthesis of the Following Compound 5-A

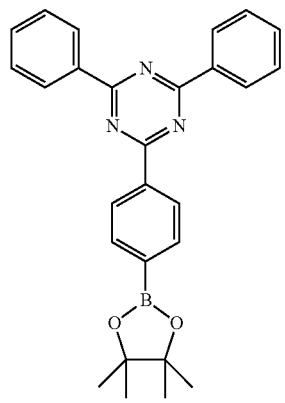

Compound 5-A (22.6 g, 85%) was prepared using the same method as the method that prepares Compound 1-C except that 8-bromonaphthalen-2-ol was used instead of the 7-bromonaphthalen-2-ol compound.

MS [M+H]⁺=452

2) Synthesis of the Following Compound 5-B

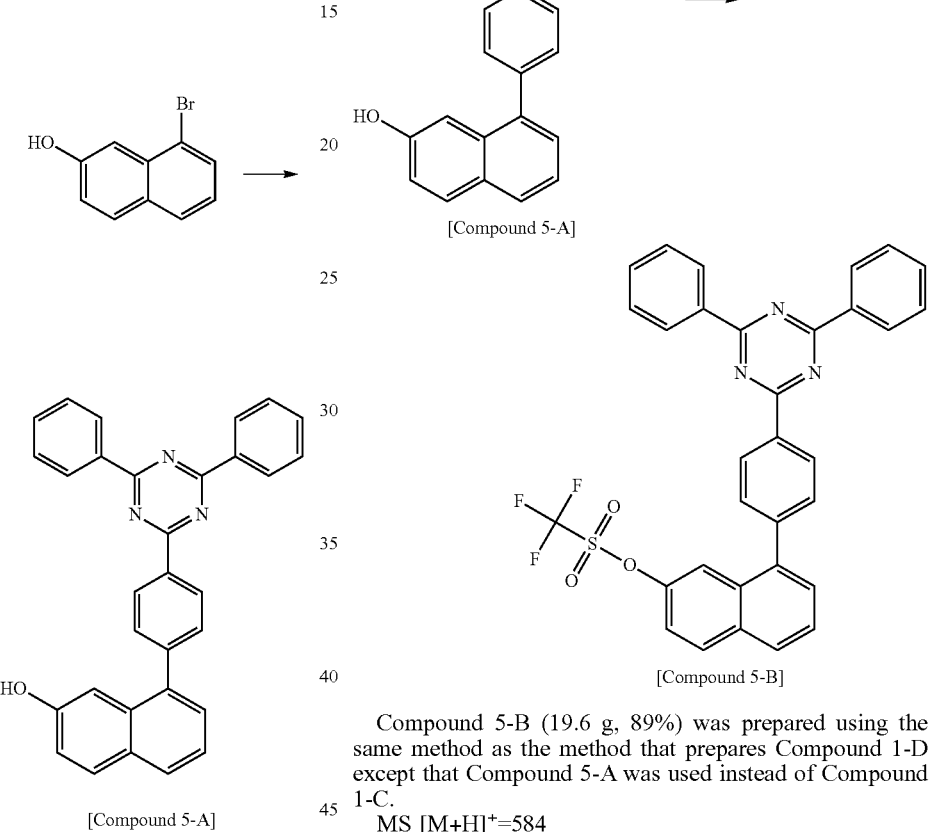

Compound 5-B (19.6 g, 89%) was prepared using the same method as the method that prepares Compound 1-D except that Compound 5-A was used instead of Compound 1-C.

MS [M+H]⁺=584

3) Synthesis of the Following Compound 2-a-1

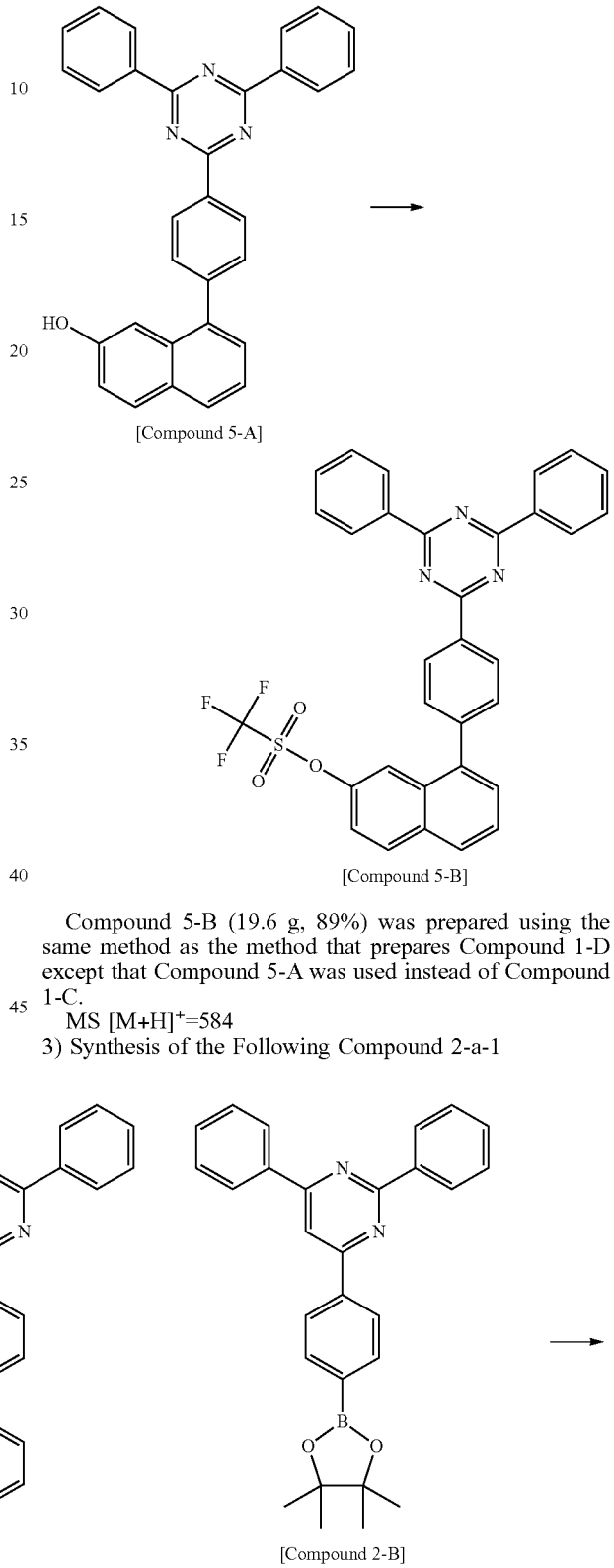

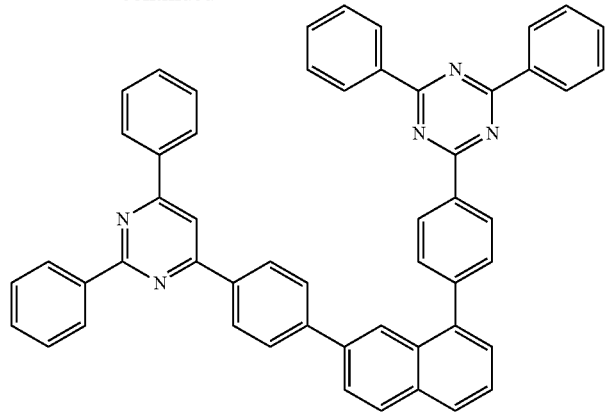

[Compound 2-a-1]

Compound 2-a-1 (11.3 g, 84%) was prepared using the same method as the method that prepares Compound 1-a-1 except that Compound 5-B was used instead of Compound 1-D.

MS [M+H]$^+$=742

<Preparation Example 7> Preparation of the Following Compound 3-a-1

1) Synthesis of the Following Compound 6-A

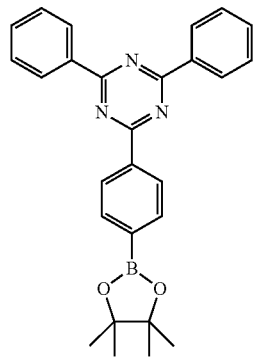

[Compound 1-B]

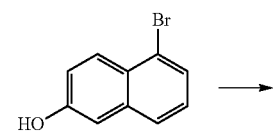

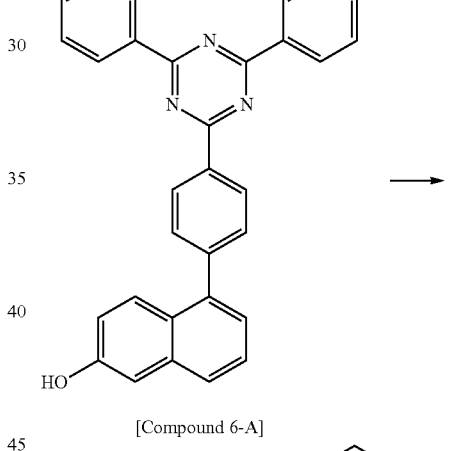

[Compound 6-A]

Compound 6-A (23.1 q, 82%) was prepared using the same method as the method that prepares Compound 1-C except that 5-bromonaphthalen-2-ol was used instead of the 7-bromonaphthalen-2-ol compound.

MS [M+H]$^+$=452

2) Synthesis of the Following Compound 6-B

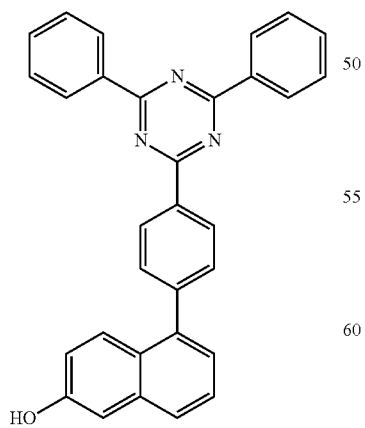

[Compound 6-A]

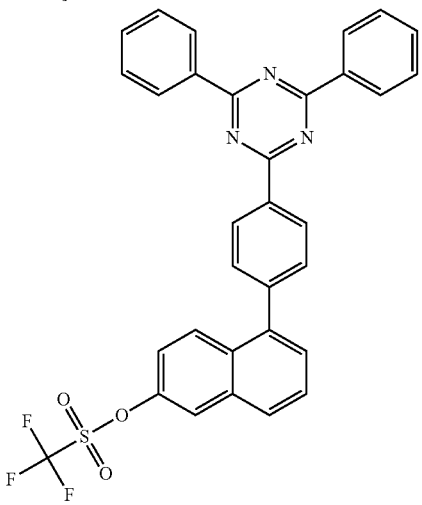

[Compound 6-B]

Compound 6-B (20.1 g, 88%) was prepared using the same method as the method that prepares Compound 1-D except that Compound 6-A was used instead of Compound 1-C.
MS [M+H]$^+$=584
3) Synthesis of the Following Compound 3-a-1
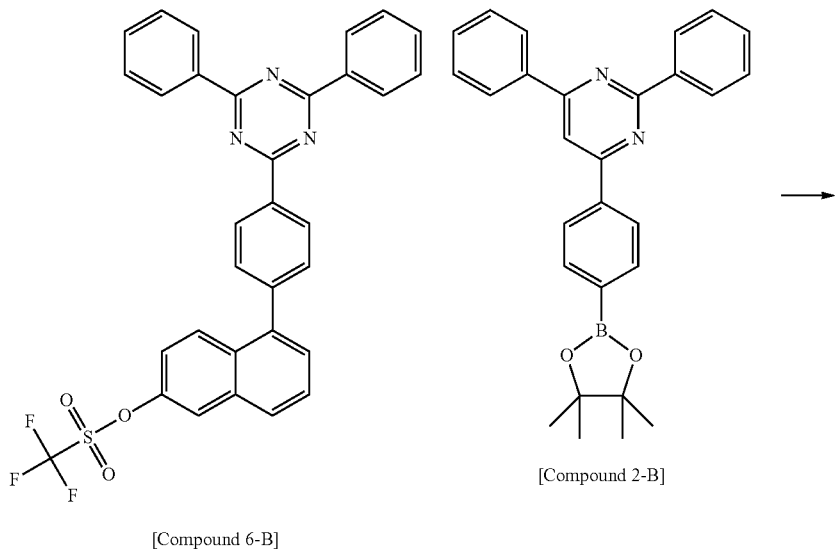
[Compound 6-B]
[Compound 2-B]
[Compound 3-a-1]

Compound 3-a-1 (12.9 g, 85%) was prepared using the same method as the method that prepares Compound 1-a-1 except that Compound 6-B was used instead of Compound 1-D.

MS [M+H]$^+$=742

<Preparation Example 8> Preparation of the Following Compound 4-a-1

1) Synthesis of the Following Compound 7-A

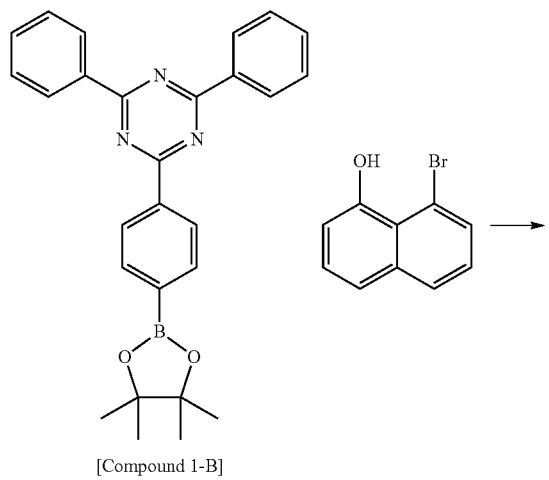

[Compound 1-B]

2) Synthesis of the Following Compound 7-B

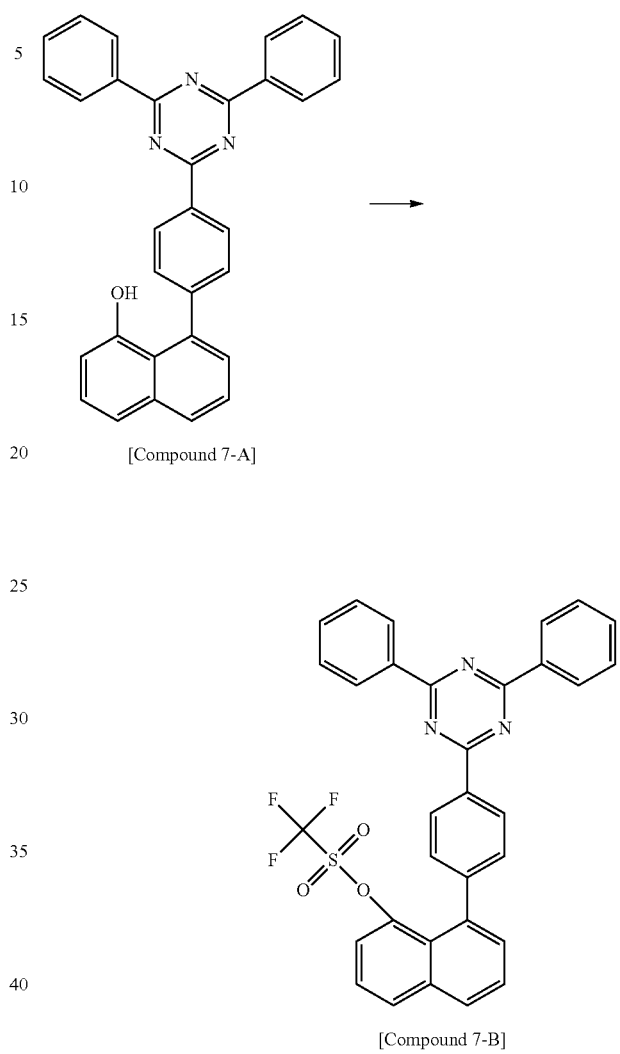

[Compound 7-A]

[Compound 7-B]

Compound 7-B (22.5 g, 86%) was prepared using the same method as the method that prepares Compound 1-D except that Compound 7-A was used instead of Compound 1-C.

MS [M+H]$^+$=584

3) Synthesis of the Following Compound 4-a-1

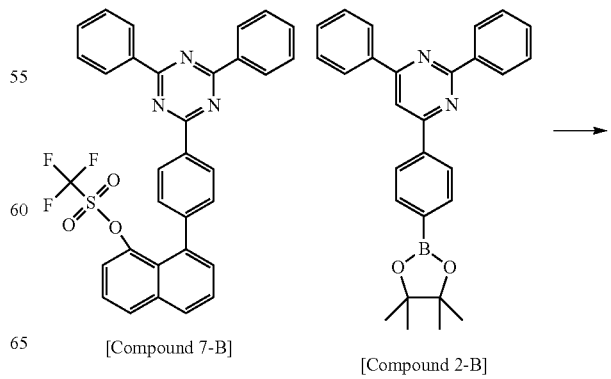

[Compound 7-B]

[Compound 2-B]

[Compound 7-A]

Compound 7-A (25.8 g, 89%) was prepared using the same method as the method that prepares Compound 1-C except that 8-bromonaphthalen-1-ol was used instead of the 7-bromonaphthalen-2-ol compound.

MS [M+H]$^+$=452

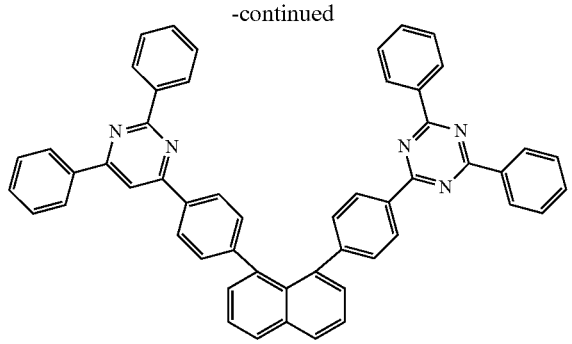
[Compound 4-a-1]
Compound 4-a-1 (18.1 g, 88%) was prepared using the same method as the method that prepares Compound 1-a-1 except that Compound 7-B was used instead of Compound 1-D.
MS [M+H]$^+$=742
<Preparation Example 9> Preparation of the Following Compound 3-b-18
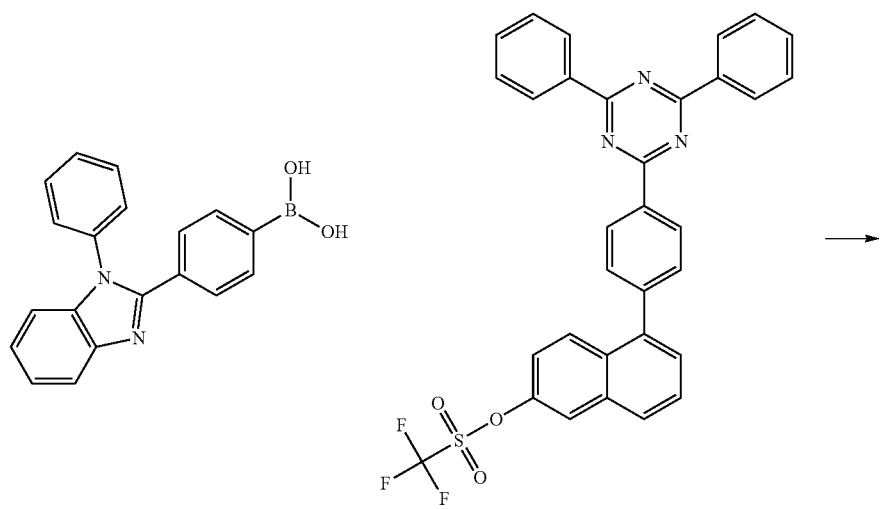
[Compound 6-B]
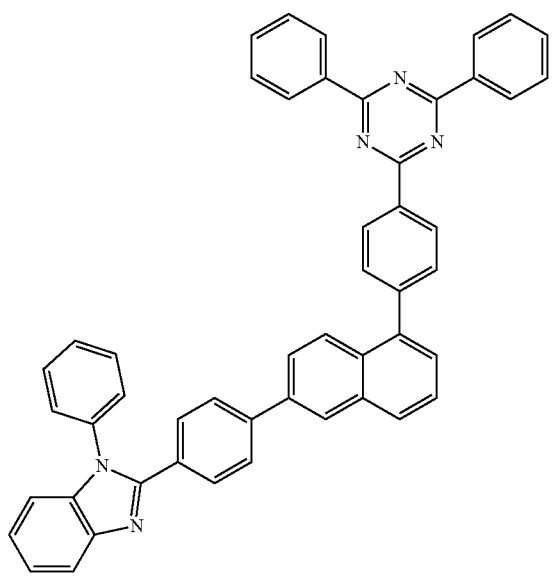
[Compound 3-b-18]

Compound 3-b-18 (19.2 g, 83%) was prepared using the same method as the method that prepares Compound 1-a-1 except that Compound 6-B was used instead of Compound 1-D.

MS [M+H]$^+$=704

<Preparation Example 10> Preparation of the Following Compound 4-b-18

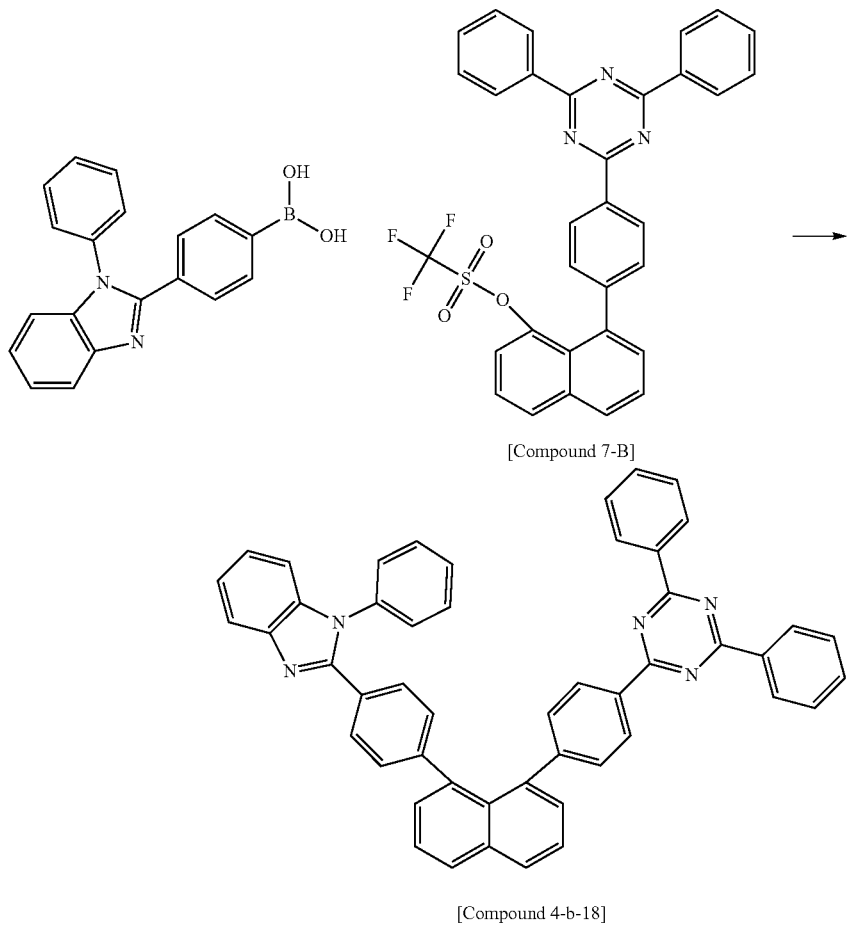

[Compound 7-B]

[Compound 4-b-18]

Compound 4-b-18 (11.6 g, 86%) was prepared using the same method as the method that prepares Compound 1-a-1 except that Compound 7-B was used instead of Compound 1-D.

MS [M+H]$^+$=704

Experimental Example

A glass substrate on which indium tin oxide (ITO) was coated as a thin film to a thickness of 1,000 Å was placed in distilled water, in which a detergent is dissolved, and ultrasonic cleaned. At this time, a product of Fischer Corporation was used as the detergent, and as the distilled water, distilled water filtered twice with a filter manufactured by Millipore Corporation was used. After the ITO was cleaned for 30 minutes, ultrasonic cleaning was repeated twice for 10 minutes using distilled water. After the cleaning with distilled water was finished, ultrasonic cleaning was performed using an isopropyl alcohol, acetone and methanol solvent, and the substrate was dried and then transferred to a plasma washer. In addition, the substrate was washed for 5 minutes using oxygen plasma, and was transferred to a vacuum deposition apparatus.

On the transparent ITO electrode prepared as above, a hole injection layer was formed to a thickness of 500 Å by thermal vacuum depositing hexanitrile hexaazatriphenylene (HAT) of the following chemical formula.

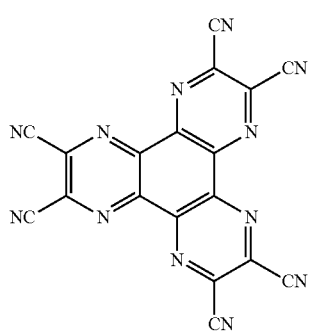

[HAT]

On the hole injection layer, a hole transfer layer was formed by vacuum depositing the following compound, 4-4'-bis[N-(1-naphthyl)-N-phenylamino]biphenyl (NPB) (400 Å), which is a material that transfers the holes.

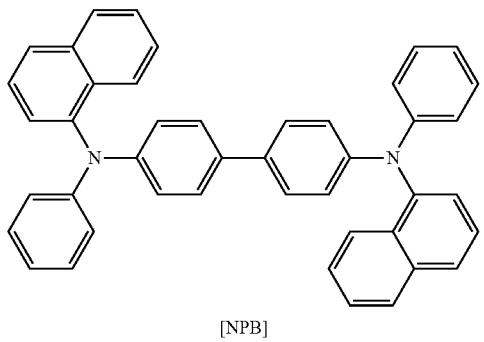

[NPB]

Subsequently, a light emitting layer was formed on the hole transfer layer to a film thickness of 300 Å by vacuum depositing the following BH and BD in the weight ratio of 25:1.

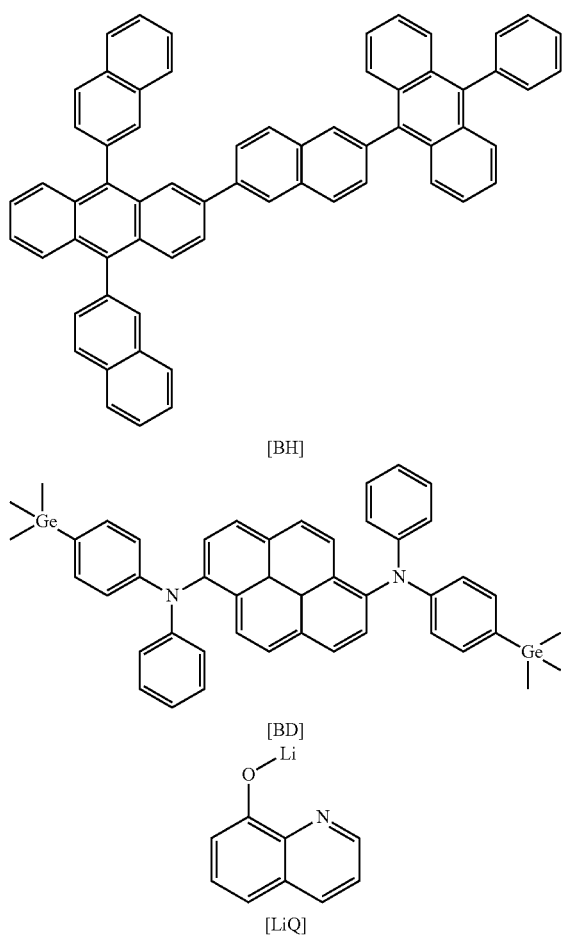

[BH]

[BD]

[LiQ]

On the light emitting layer, an electron injection and transfer layer were formed to a thickness of 350 Å by vacuum depositing Compound 1-a-1 prepared in Preparation Example 1 and the lithium quinolate (LiQ) compound in the weight ratio of 1:1. A cathode was formed an the electron injection and transfer layer by depositing lithium fluoride (LiF) to a thickness of 12 Å and aluminum to a thickness of 2,000 Å in consecutive order.

In the above process, the deposition rate of the organic material was maintained to be 0.4 to 0.7 Å/sec, the deposition rate of lithium fluoride of the cathode to be 0.3 Å/sec, and the deposition rate of aluminum to be 2 Å/sec, and the degree of vacuum when being deposited was maintained to be $2\times10^{-7}$ to $5\times10^{-6}$ torr, and as a result, the organic light emitting device was manufactured.

Experimental Example 2

The organic light emitting device was manufactured using the same method as in Experimental Example 1 except that Compound 1-a-2 was used instead of Compound 1-a-1 in Experimental Example 1.

Experimental Example 3

The organic light emitting device was manufactured using the same method as in Experimental Example 1 except that Compound 1-a-5 was used instead of Compound 1-a-1 in Experimental Example 1.

Experimental Example 4

The organic light emitting device was manufactured using the same method as in Experimental Example 1 except that Compound 1-b-1 was used instead of Compound 1-a-1 in Experimental Example 1.

Experimental Example 5

The organic light emitting device was manufactured using the same method as in Experimental Example 1 except that Compound 1-b-2 was used instead of Compound 1-a-1 in Experimental Example 1.

Experimental Example 6

The organic light emitting device was manufactured using the same method as in Experimental Example 1 except that Compound 2-a-1 was used instead of Compound 1-a-1 in Experimental Example 1.

Experimental Example 7

The organic light emitting device was manufactured using the same method as in Experimental Example 1 except that Compound 3-a-1 was used instead of Compound 1-a-1 in Experimental Example 1.

Experimental Example 8

The organic light emitting device was manufactured using the same method as in Experimental Example 1 except that Compound 4-a-1 was used instead of Compound 1-a-1 in Experimental Example 1.

Experimental Example 9

The organic light emitting device was manufactured using the same method as in Experimental Example 1 except that Compound 3-b-18 was used instead of Compound 1-a-1 in Experimental Example 1.

Experimental Example 10

The organic light emitting device was manufactured using the same method as in Experimental Example 1 except that Compound 4-b-18 was used instead of Compound 1-a-1 in Experimental Example 1.

Comparative Example 1

The organic light emitting device was manufactured using the same method as in Experimental Example 1 except that the compound of the following ET1 was used instead of Compound 1-a-1 in Experimental Example 1.

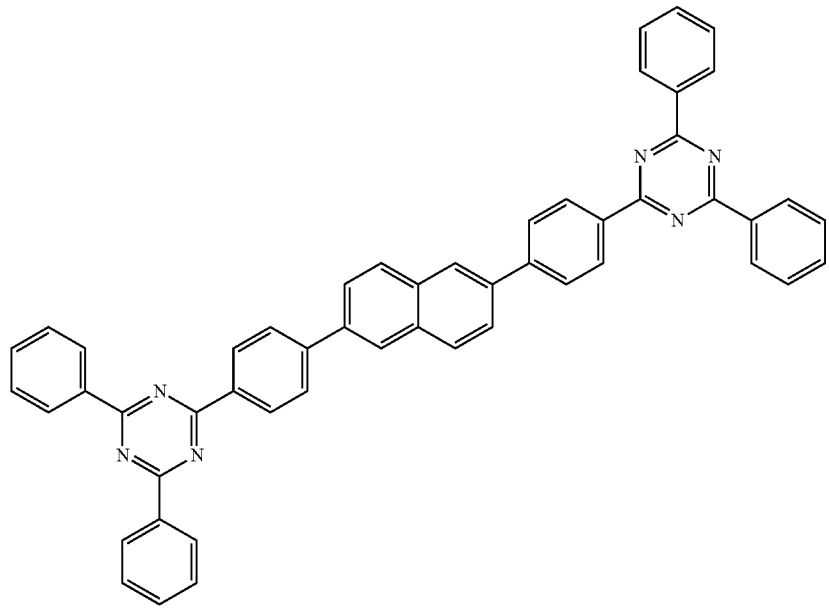

[ET1]

Comparative Example 2

The organic light emitting device was manufactured using the same method as in Experimental Example 1 except that the compound of the following ET2 was used instead of Compound 1-a-1 in Experimental Example 1.

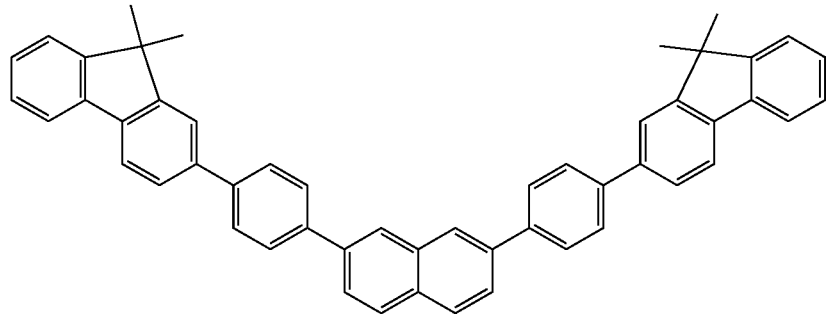

[ET2]

Comparative Example 3

The organic light emitting device was manufactured using the same method as in Experimental Example 1 except that the compound of the following ET3 was used instead of Compound 1-a-1 in Experimental Example 1.

[ET3]

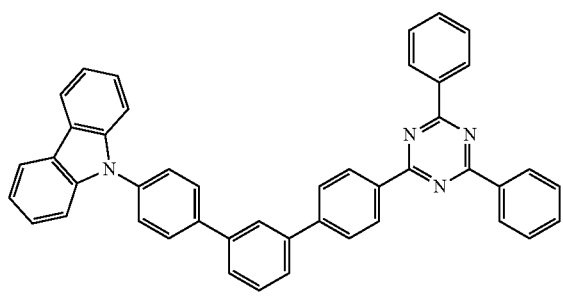

Comparative Example 4

The organic light emitting device was manufactured using the same method as in Experimental Example 1 except that the compound of the following ET4 was used instead of Compound 1-a-1 in Experimental Example 1.

[ET4]

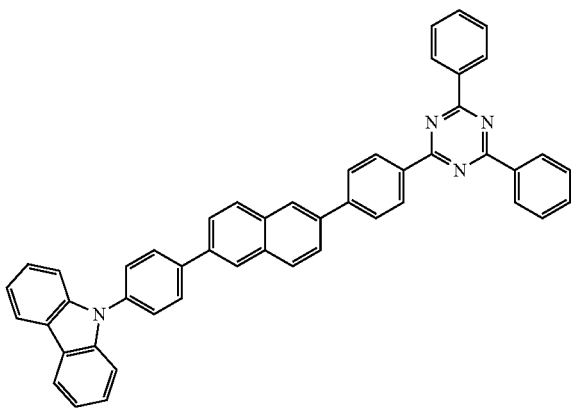

When current was applied to the organic light emitting device manufactured by Experimental Examples 1 to 8 and Comparative Examples 1 to 4, the results of Table 1 were obtained.

TABLE 1

| | Compound | Voltage (V@10 mA/cm$^2$) | Efficiency (cd/A@10 mA/cm$^2$) | Color Coordinates (x, y) |
|---|---|---|---|---|
| Experimental Example 1 | Compound 1-a-1 | 3.81 | 5.13 | (0.136, 0.127) |
| Experimental Example 2 | Compound 1-a-2 | 3.75 | 4.99 | (0.139, 0.128) |
| Experimental Example 3 | Compound 1-a-5 | 3.89 | 5.24 | (0.138, 0.124) |
| Experimental Example 4 | Compound 1-b-1 | 3.88 | 5.31 | (0.136, 0.127) |
| Experimental Example 5 | Compound 1-b-2 | 3.76 | 5.29 | (0.133, 0.121) |
| Experimental Example 6 | Compound 2-a-1 | 3.83 | 5.17 | (0.139, 0.126) |
| Experimental Example 7 | Compound 3-a-1 | 3.76 | 5.28 | (0.139, 0.127) |
| Experimental Example 8 | Compound 4-a-1 | 3.59 | 5.31 | (0.137, 0.129) |
| Experimental Example 9 | Compound 3-b-18 | 3.78 | 5.12 | (0.136, 0.125) |
| Experimental Example 10 | Compound 4-b-18 | 3.82 | 5.16 | (0.136, 0.129) |
| Comparative Example 1 | ET1 | 4.11 | 3.98 | (0.137, 0.126) |
| Comparative Example 2 | ET2 | 4.21 | 4.02 | (0.136, 0.123) |
| Comparative Example 3 | ET3 | 4.25 | 4.21 | (0.139, 0.119) |
| Comparative Example 4 | ET4 | 4.32 | 4.04 | (0.138, 0.120) |

From the results of Table 1, in which Experimental Examples 1 to 8 and Comparative Examples 1 and 2 are compared, it can be verified that an organic light emitting device having excellent electron transfer and injection abilities thereby having low voltage and/or high efficiency can be provided when, with a naphthyl group as the standard, L1 and L2 are different from each other or Ar1 and Ar2 are different from each other, compared to when L1 and L2 are the same as each other and Ar1 and Ar2 are the same as each other.

In addition, as shown in Table 1, it can be verified that, when a naphthyl group is the standard, an organic light emitting device having excellent electron transfer and injection abilities thereby having low voltage and/or high efficiency can be provided compared to when other structures are the standard.

From the results of Table 1, in which Experimental Examples 1 to 8 and Comparative Example 4 are compared, it can be verified that electron transfer and injection abilities are excellent for the naphthyl group at a specific position according to one embodiment of the present specification.

REFERENCES

1: Substrate
2: Anode
3: Light Emitting Layer
4: Cathode
5: Hole Injection Layer
6: Hole Transfer Layer
7: Electron Transfer Layer

The invention claimed is:

1. A hetero-cyclic compound represented by the Following Chemical Formula 1:

[Chemical Formula 1]

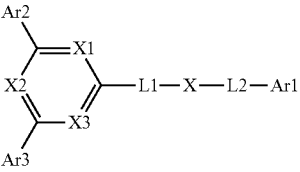

wherein, in Chemical Formula 1,

X is any one of the following structural formulae;

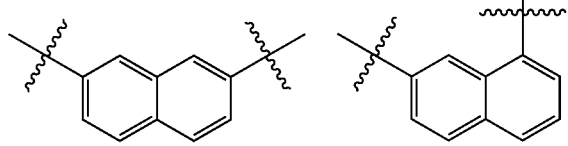

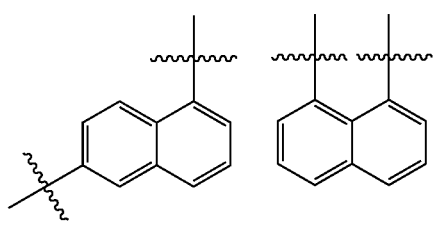

L1 and L2 are the same as or different from each other, each independently a substituted or unsubstituted arylene group or a substituted or unsubstituted alkenylene group;

Ar1 is a fluorenyl group or a fluoranthenyl group unsubstituted or substituted with substituent groups selected from the group consisting of deuterium, an alkyl group, an alkenyl group, a cycloalkyl group, an aryl group, an arylalkyl group, an arylalkenyl group and heteroring group; or a heteroring group including one or more of O, N and S as a heteroatom unsubstituted or substituted with substituent groups selected from the group consisting of deuterium, an alkyl group, an alkenyl group, a cycloalkyl group, an aryl group, an arylalkyl group, an arylalkenyl group and heteroring group;

L1 and L2 are different from each other, or

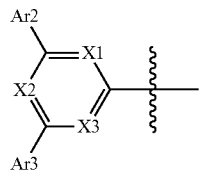

and Ar1 are different from each other;

X1 to X3 are the same as or different from each other, each independently N or CH, and at least one of X1 to X3 is N; and Ar2 and Ar3 are the same as or different from each other, each independently an unsubstituted aryl group or a heteroring group including one or more of O, N and S as a heteroatom unsubstituted or substituted with substituent groups selected from the group consisting of deuterium, an alkyl group, an alkenyl group, a cycloalkyl group, an aryl group, an arylalkyl group, an arylalkenyl group and heteroring group.

2. The hetero-cyclic compound of claim 1, wherein Ar1 is represented by the following Chemical Formula 2:

[Chemical Formula 2]

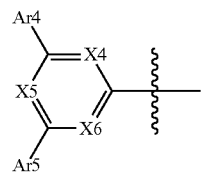

wherein, in Chemical Formula 2,

X4 to X6 are the same as or different from each other, each independently N or CH, and at least one of X4 to X6 is N; and Ar4 and Ar5 are the same as or different from each other, each independently an aryl group unsubstituted or substituted with substituent groups selected from the group consisting of deuterium, an alkyl group, an alkenyl group, a cycloalkyl group, an aryl group, an arylalkyl group, an arylalkenyl group and heteroring group; or a heteroring group including one or more of O, N and S as a heteroatom unsubstituted or substituted with substituent groups selected from the group consisting of deuterium, an alkyl group, an alkenyl group, a cycloalkyl group, an aryl group, an arylalkyl group, an arylalkenyl group and heteroring group.

3. The hetero-cyclic compound of claim 1, wherein L1 and L2 are different from each other, each independently a substituted or unsubstituted phenylene group.

4. The hetero-cyclic compound of claim 1, wherein Ar1 is represented by any one of the following Chemical Formula 3 to Chemical Formula 10:

[Chemical Formula 3]

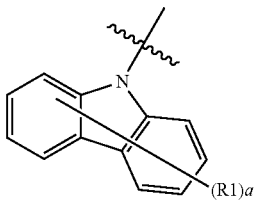

[Chemical Formula 4]

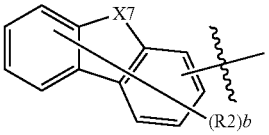

[Chemical Formula 5]

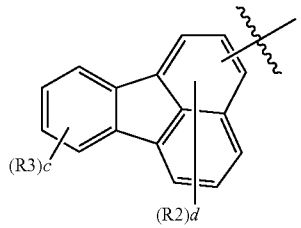

[Chemical Formula 6]

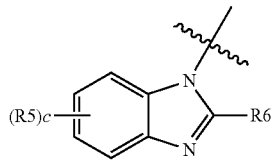

[Chemical Formula 7]

[Chemical Formula 8]

[Chemical Formula 9]

[Chemical Formula 10]

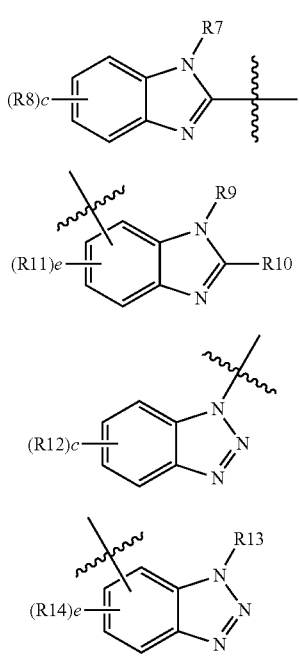

wherein, in Chemical Formulae 3 to 10, a is an integer of 0 to 8;
b is an integer of 0 to 7;
c is an integer of 0 to 4;
d is an integer of 0 to 5;
e is an integer of 0 to 3;

X7 is S, O, NR or CRR'; and

R, R', and R1 to R14 are the same as or different from each other, each independently hydrogen; deuterium; a substituted or unsubstituted alkyl group; a substituted or unsubstituted cycloalkyl group; a substituted or unsubstituted alkenyl group; a substituted or unsubstituted aryl group; or a substituted or unsubstituted heteroring group including one or more of O, N and S as a heteroatom.

5. The hetero-cyclic compound of claim 1, wherein Ar2 and Ar3 are the same as or different from each other, and each independently an unsubstituted phenyl group; an unsubstituted biphenyl group; or an unsubstituted naphthyl group.

6. The hetero-cyclic compound of claim 2, wherein Ar4 and Ar5 are the same as or different from each other, and each independently a phenyl group unsubstituted or substituted with substituent groups selected from the group consisting of deuterium, an alkyl group, and alkenyl group, a cycloalkyl group, an aryl group, an arylalkyl group, an arylalkenyl group and heteroring group; a biphenyl group unsubstituted or substituted with substituent groups selected from the group consisting of deuterium, an alkyl group, an alkenyl group, a cycloalkyl group, an aryl group, an arylalkyl group, an arylalkenyl group and heteroring group; or a naphthyl group unsubstituted or substituted with substituent groups selected from the group consisting of deuterium, an alkyl group, an alkenyl group, a cycloalkyl group, an aryl group, an arylalkyl group, an arylalkenyl group and heteroring group.

7. The hetero-cyclic compound of claim 1, wherein the compound represented by Chemical Formula 1 is represented by any one of the following Chemical Formulae 1-a-1 to 1-a-14, 2-a-1 to 2-a-14, 3-a-1 to 3-a-14, and 4-a-1 to 4-a-14:

Chemical Formula 1-a-1

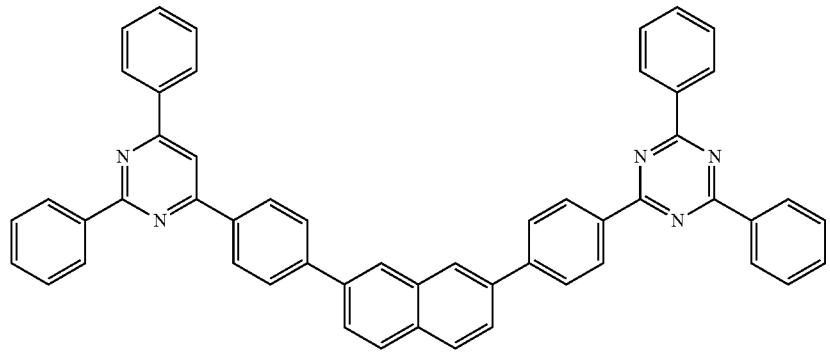

Chemical Formula 1-a-2

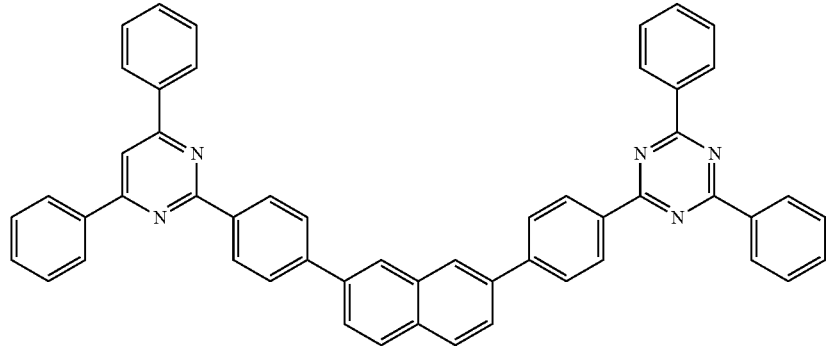

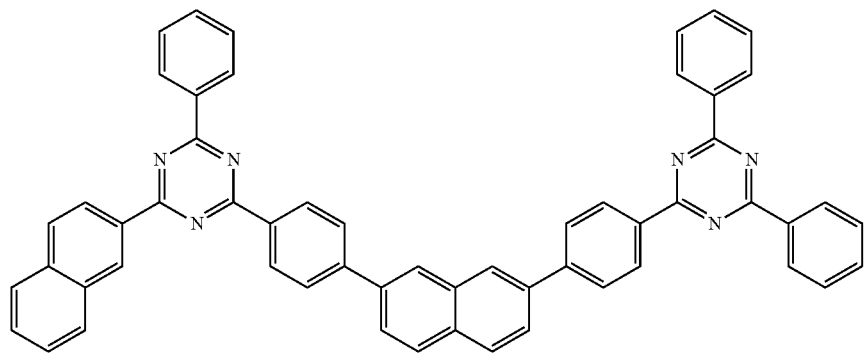
Chemical Formula 1-a-3
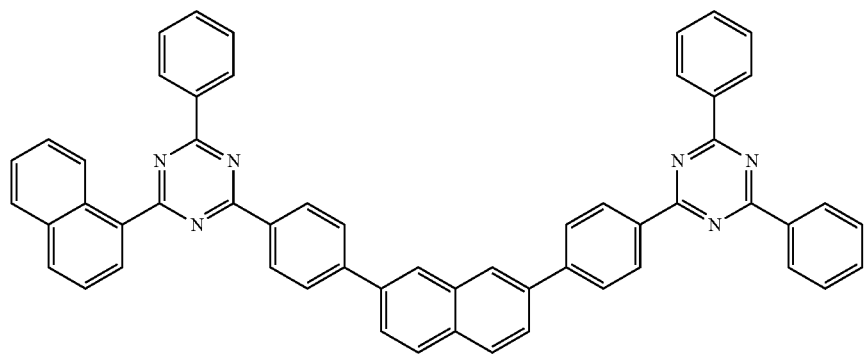
Chemical Formula 1-a-4
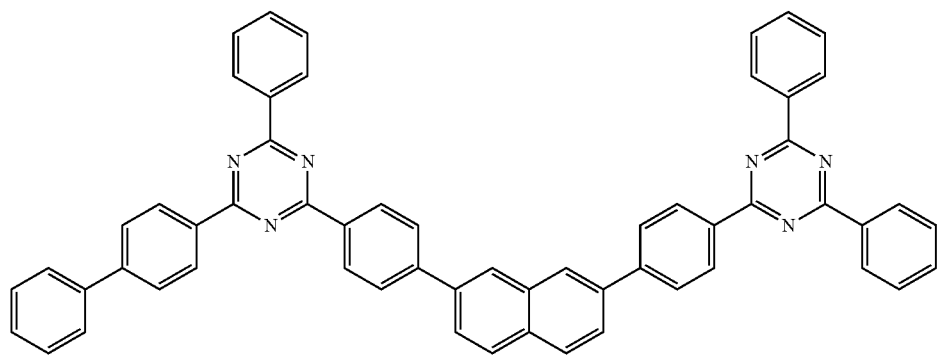
Chemical Formula 1-a-5
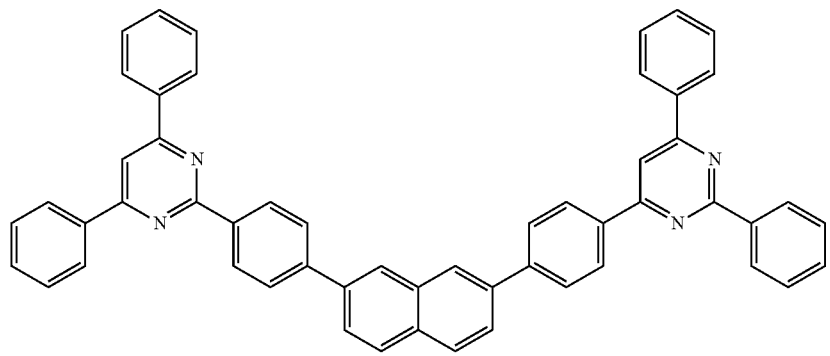
Chemical Formula 1-a-6

-continued
Chemical Formula 1-a-7
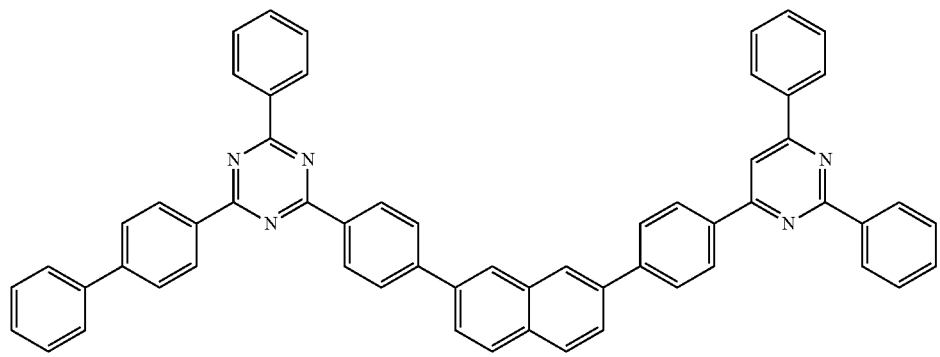
Chemical Formula 1-a-8
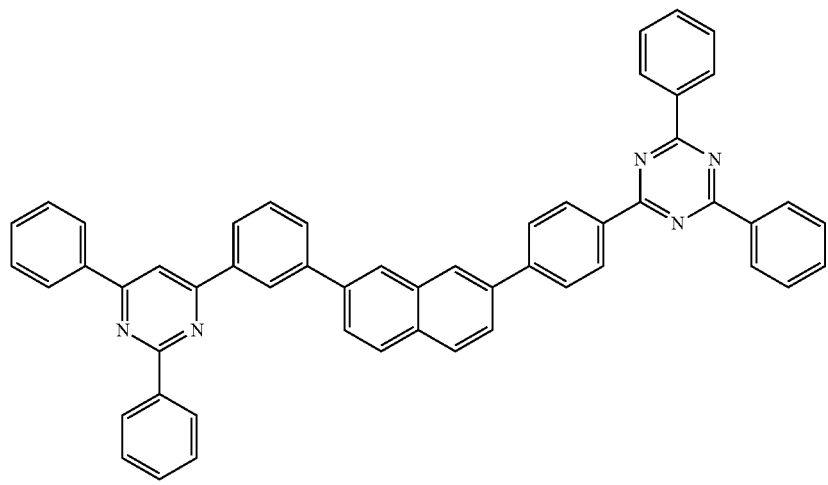
Chemical Formula 1-a-9
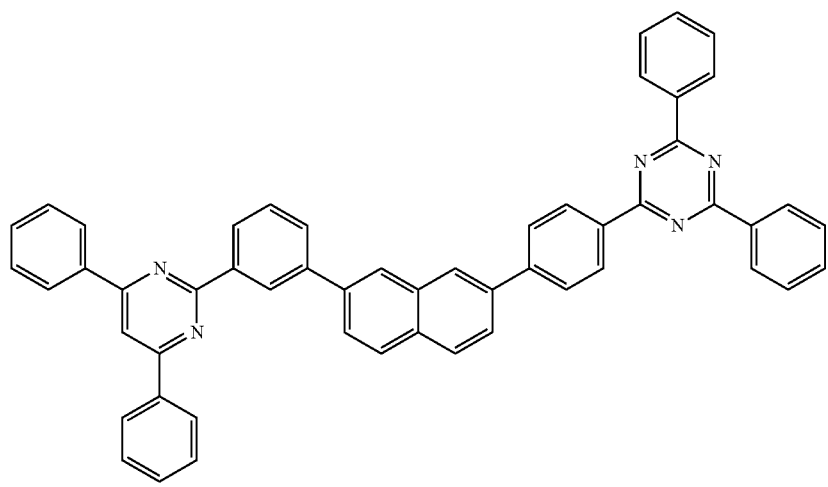

-continued
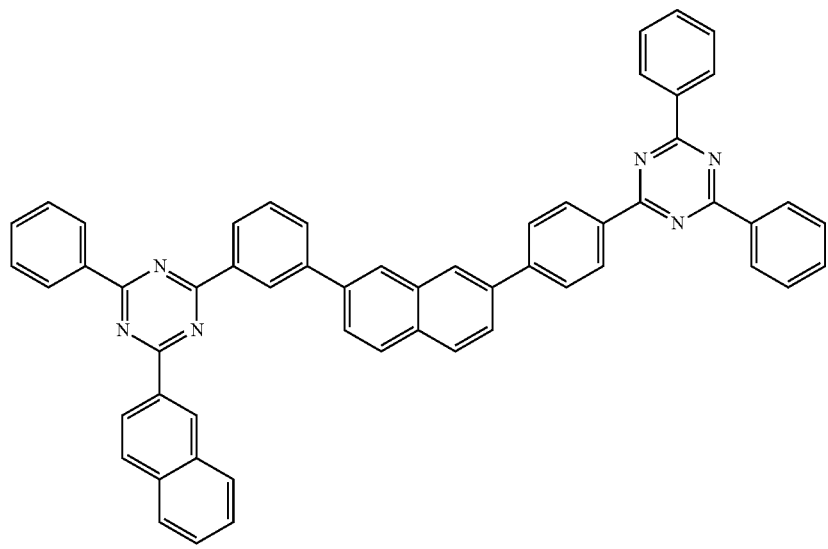
Chemical Formula 1-a-10
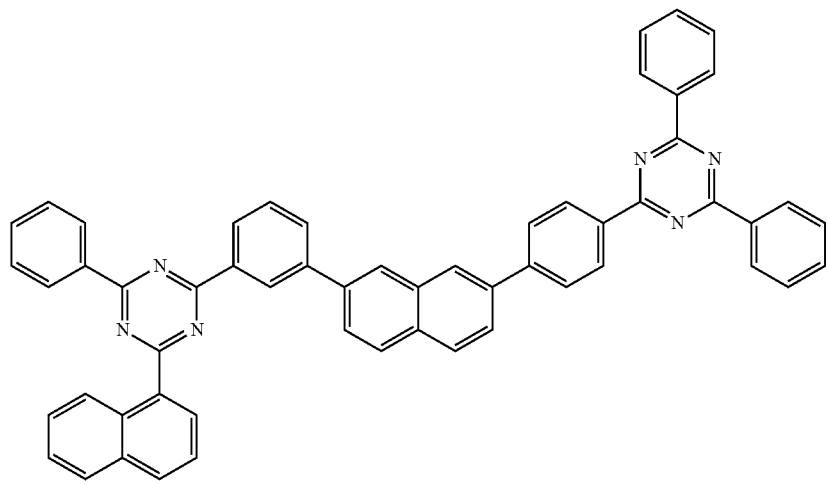
Chemical Formula 1-a-11
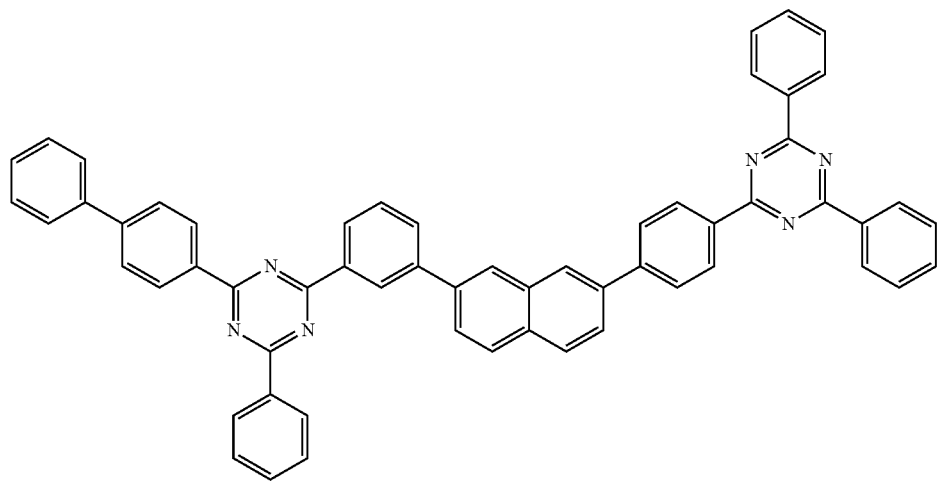
Chemical Formula 1-a-12

Chemical Formula 1-a-13
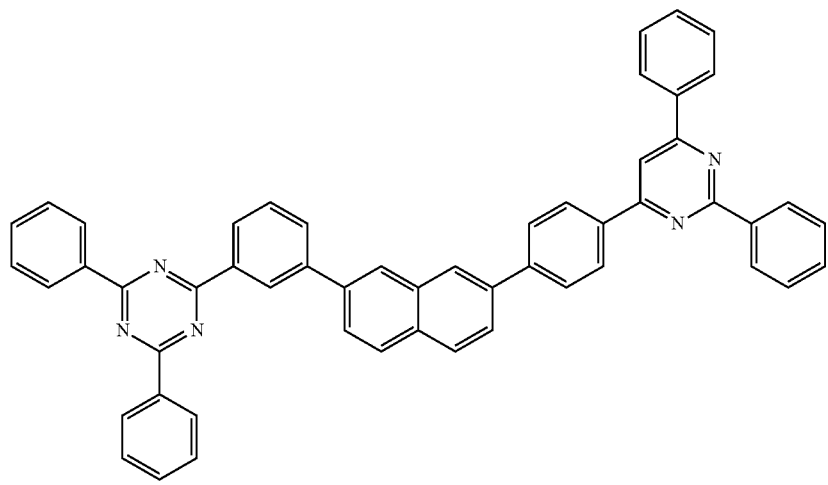
Chemical Formula 1-a-14
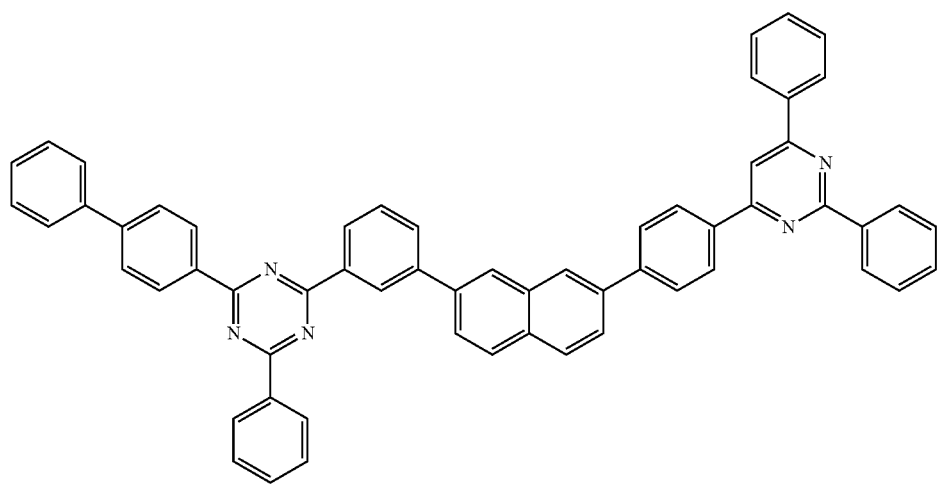
Chemical Formula 2-a-1
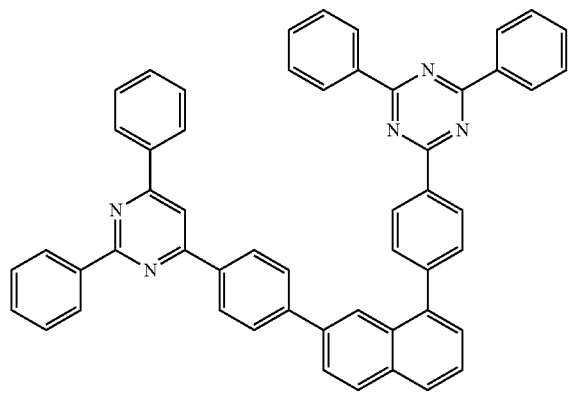
Chemical Formula 2-a-2
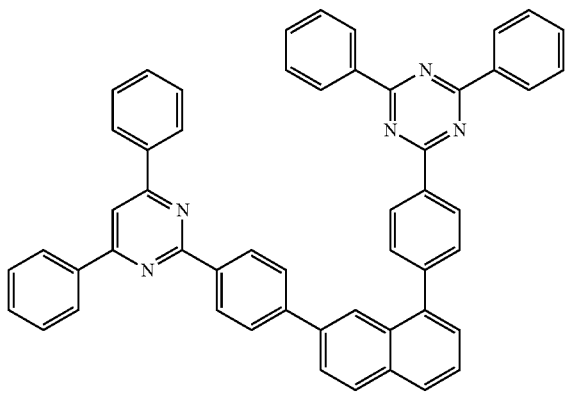

-continued
Chemical Formula 2-a-3
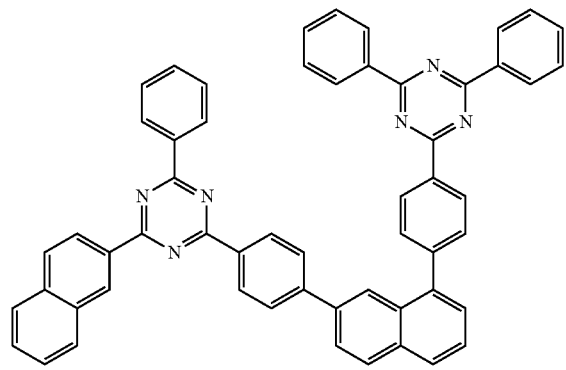
Chemcial Formula 2-a-4
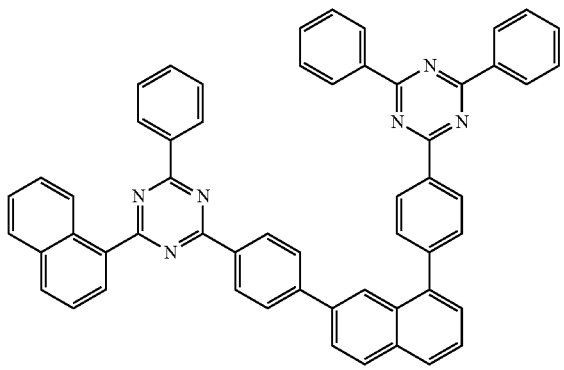
Chemical Formula 2-a-5
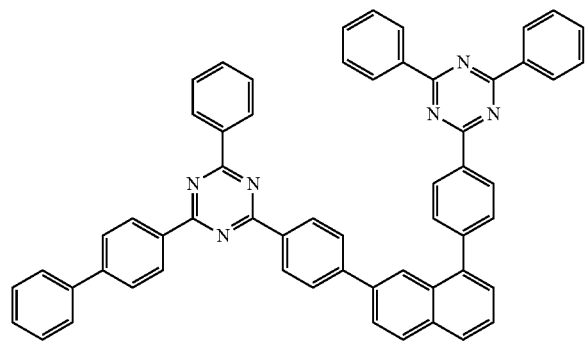
Chemical Formula 2-a-6
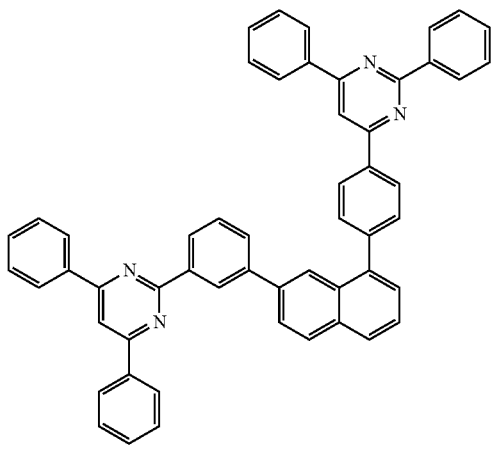
Chemical Formula 2-a-7
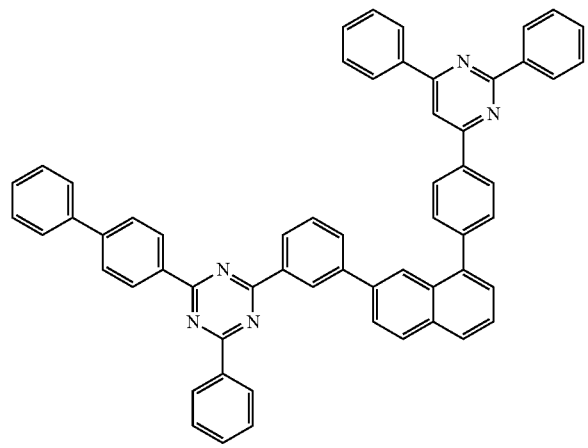
Chemcial formula 2-a-8
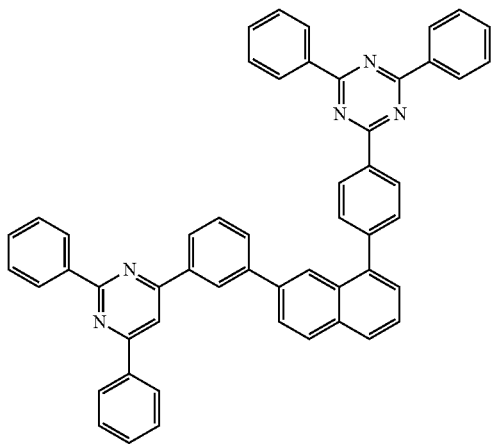

-continued
Chemical Formula 2-a-9
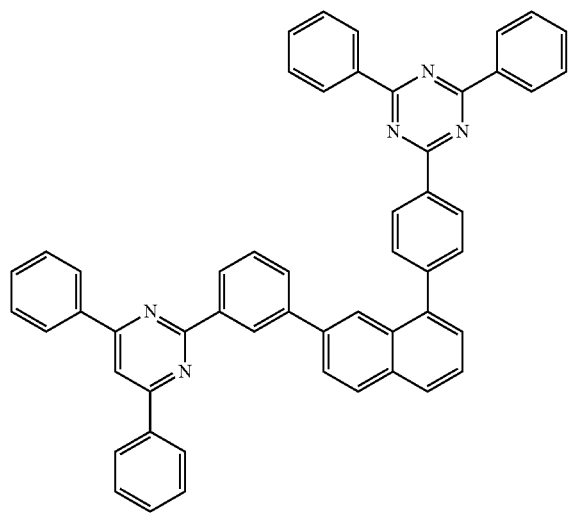
Chemical Formula 2-a-10
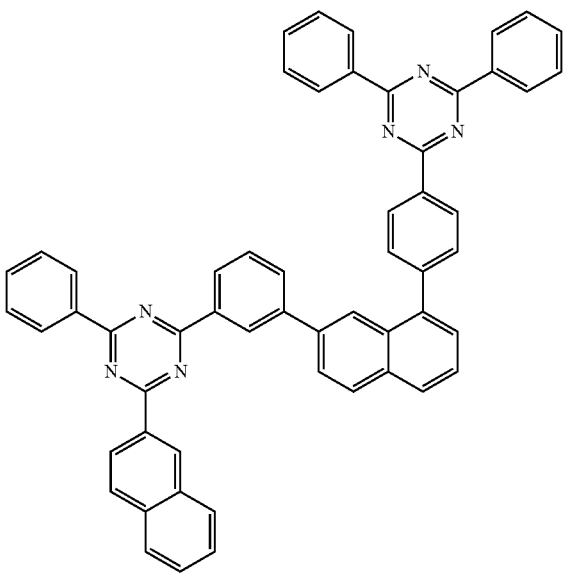
Chemical Formula 2-a-11
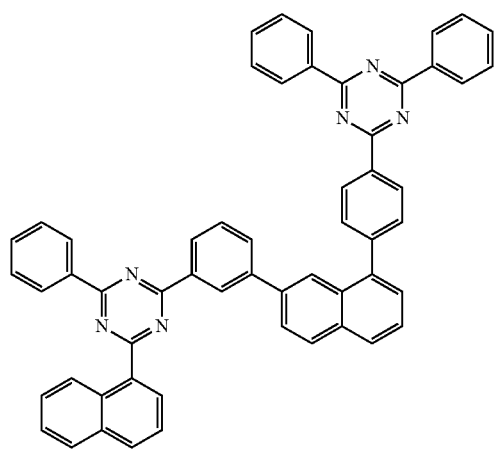
Chemical Formula 2-a-12
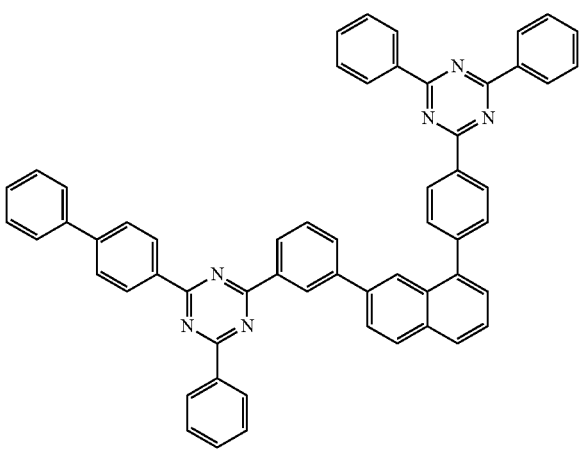
Chemical Formula 2-a-13
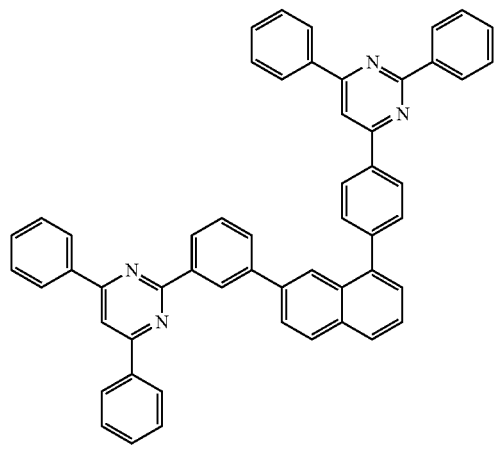
Chemical Formula 2-a-14
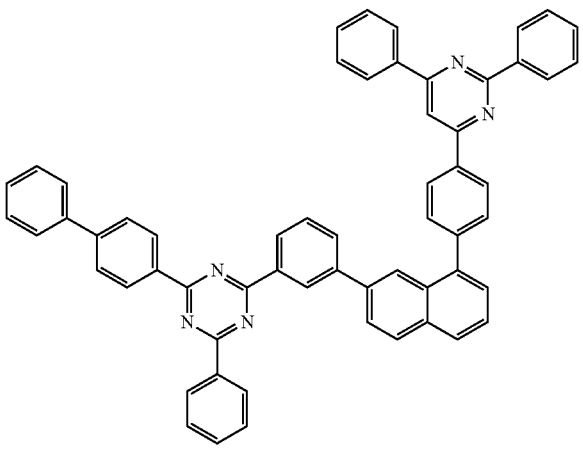

Chemical Formula 3-a-1
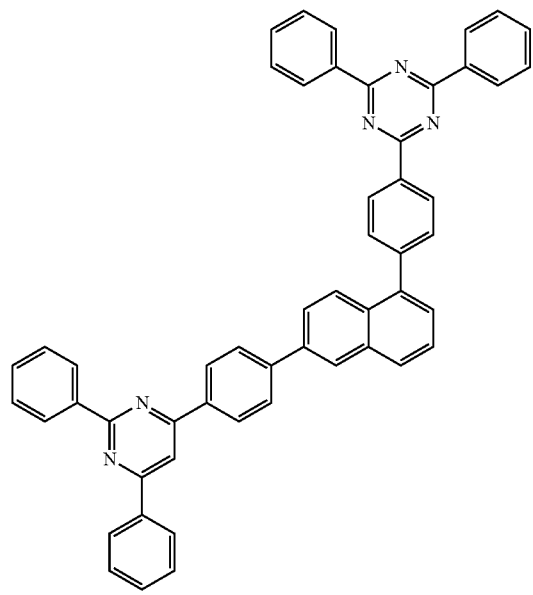
Chemical Formula 3-a-2
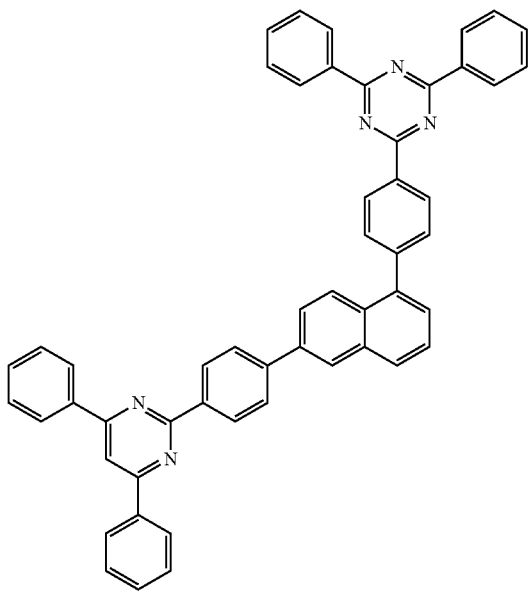
Chemical Formula 3-a-3
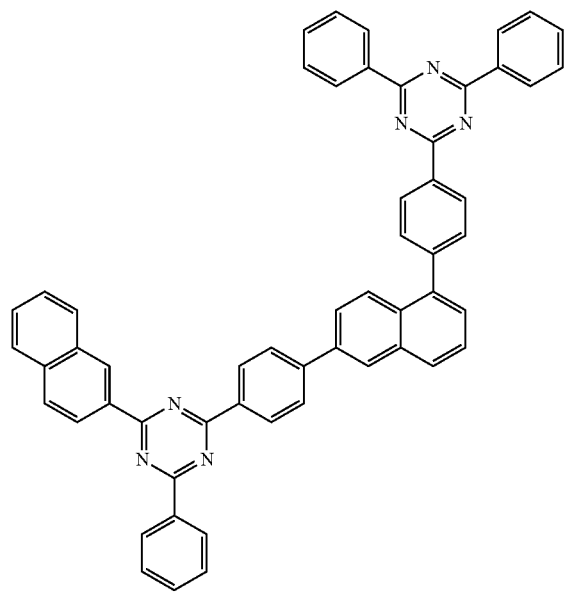
Chemical Formula 3-a-4
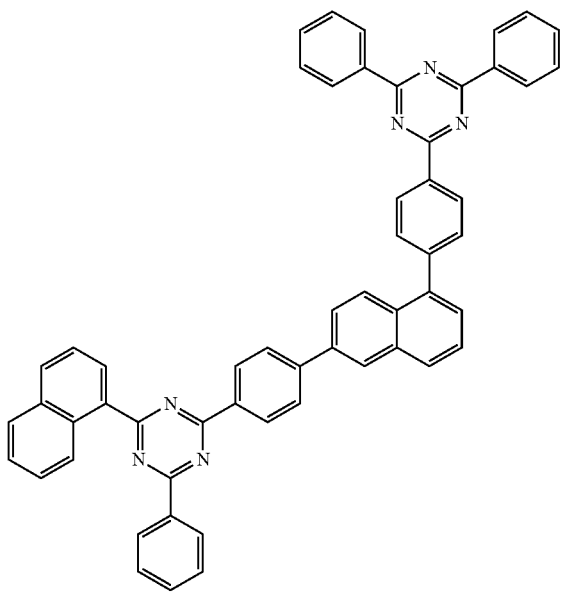

-continued
Chemical Formula 3-a-5
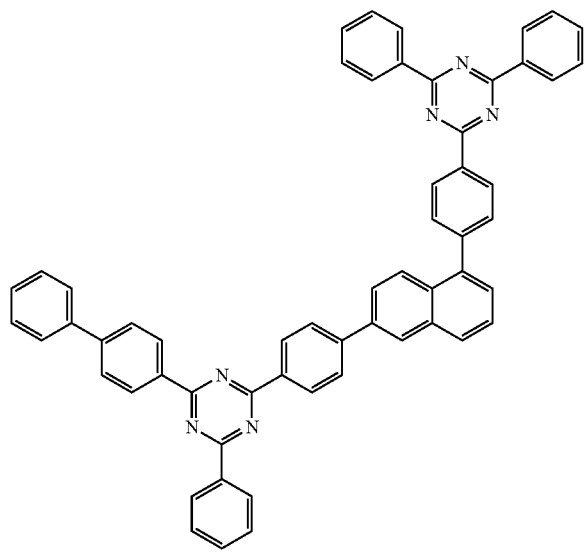
Chemical Formula 3-a-6
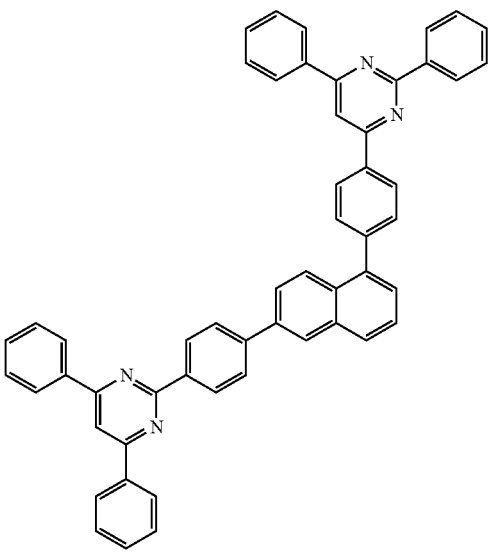
Chemical Formula 3-a-7
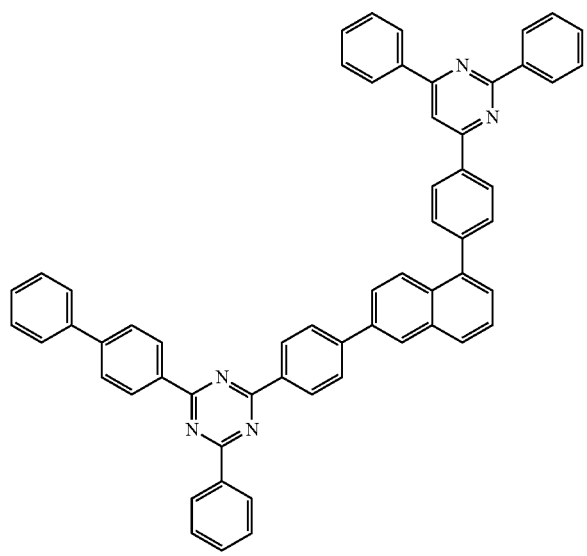
Chemical Formula 3-a-8
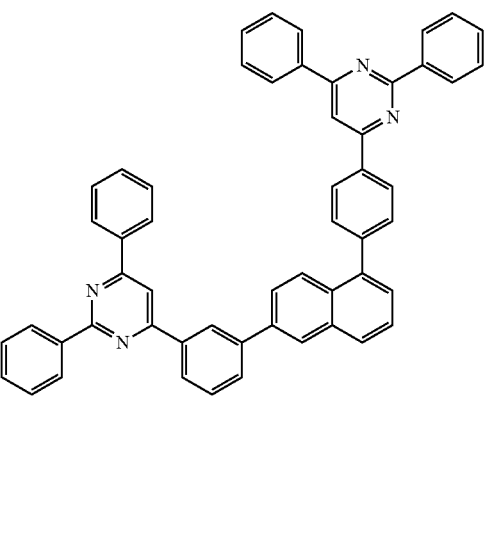
Chemical Formula 3-a-9
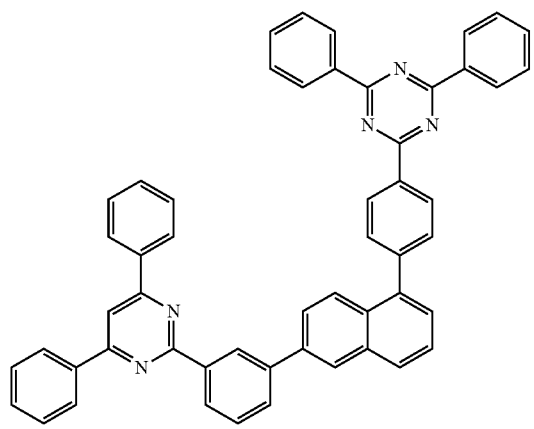
Chemical Formula 3-a-10
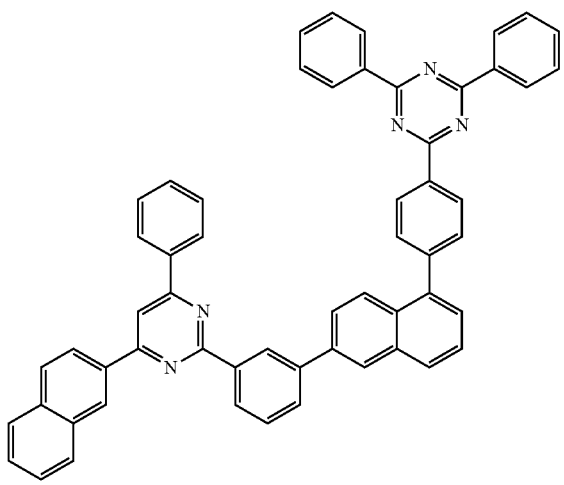

-continued
Chemical Formula 3-a-11
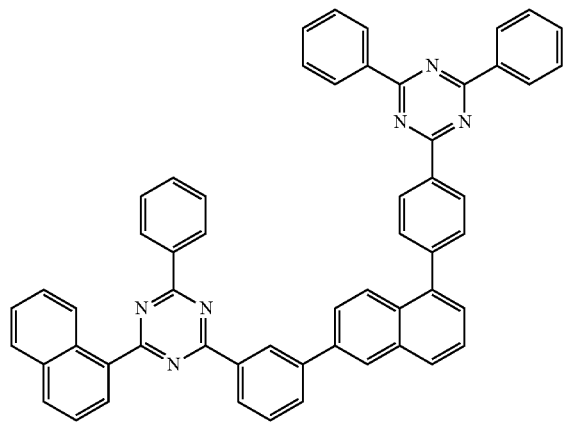
Chemical Formula 3-a-12
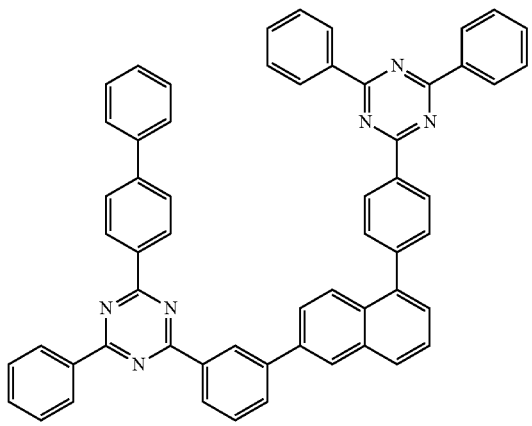
Chemical Formula 3-a-13
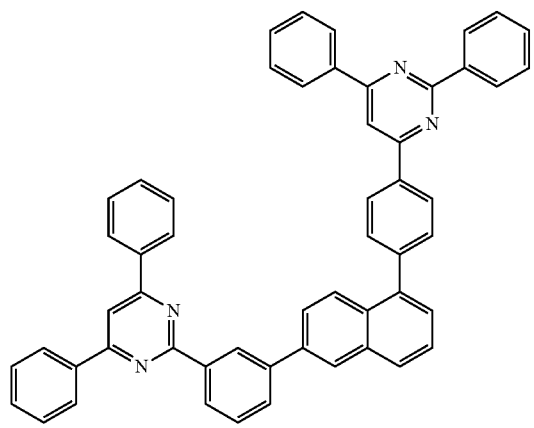
Chemical Formula 3-a-14
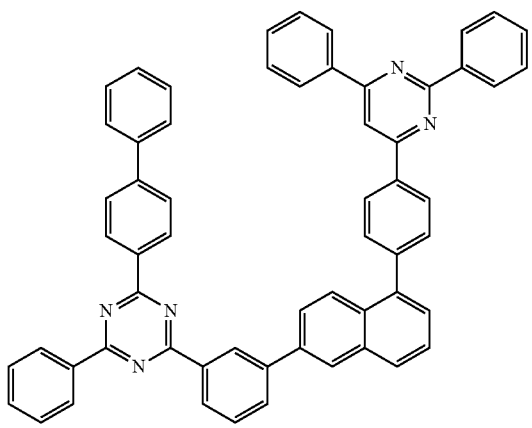
Chemical Formula 4-a-1
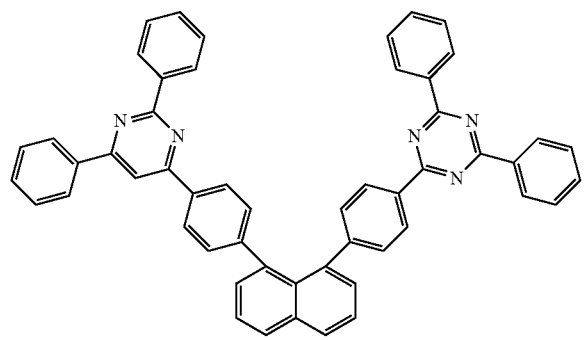
Chemical Formula 4-a-2
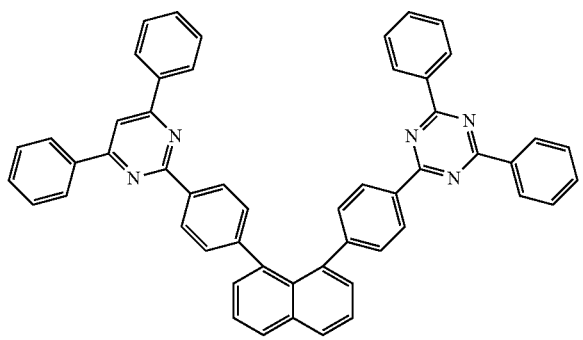
Chemical Formula 4-a-3
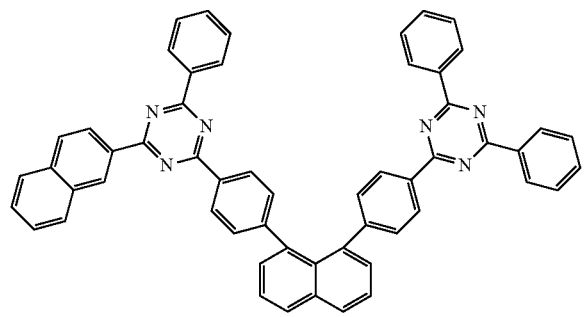
Chemical Formula 4-a-4
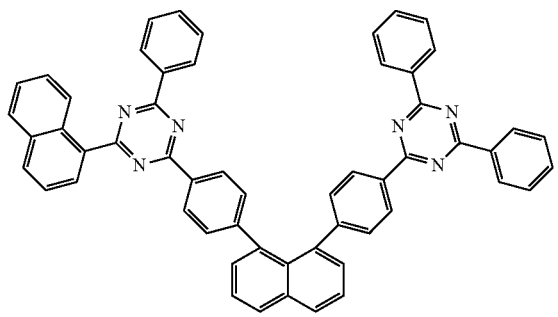

Chemical Formula 4-a-5
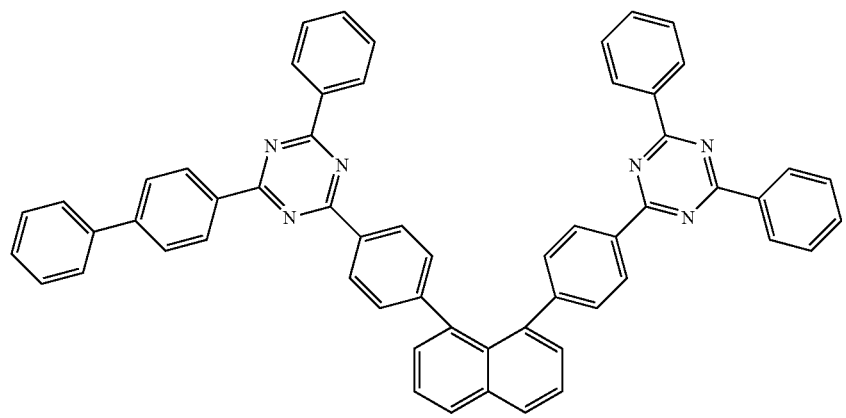
Chemical Formula 4-a-6
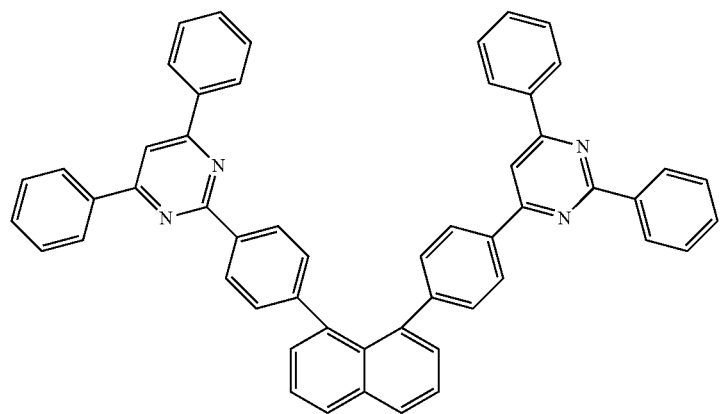
Chemical Formula 4-a-7
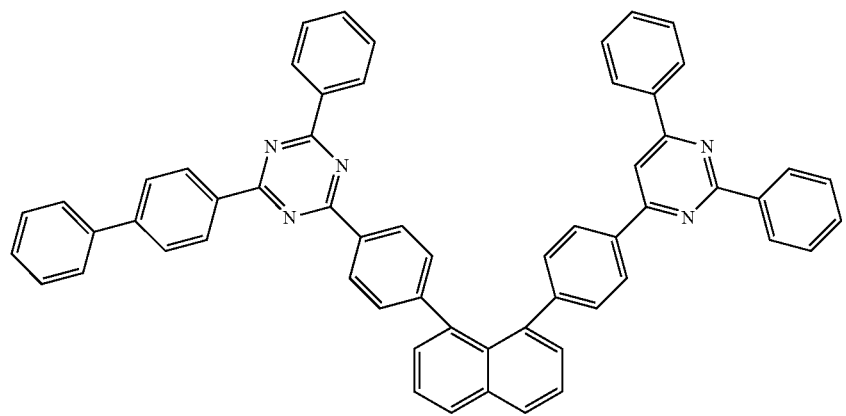

Chemical Formula 4-a-8
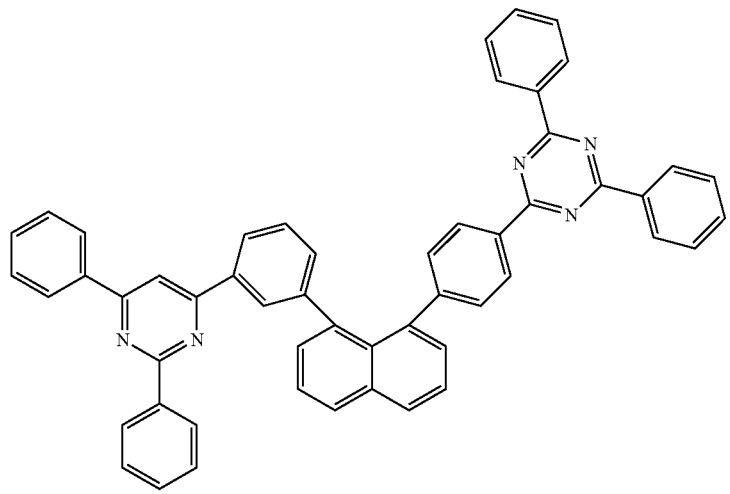
Chemical Formula 4-a-9
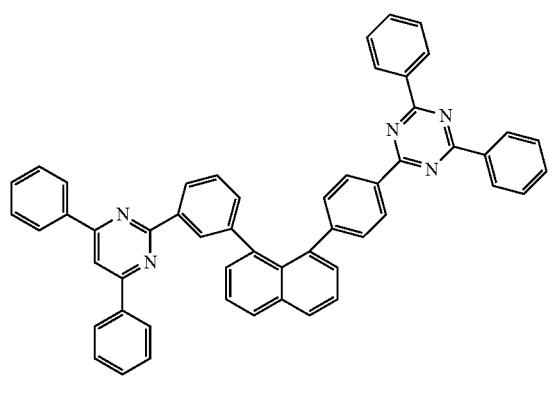
Chemical Formula 4-a-10
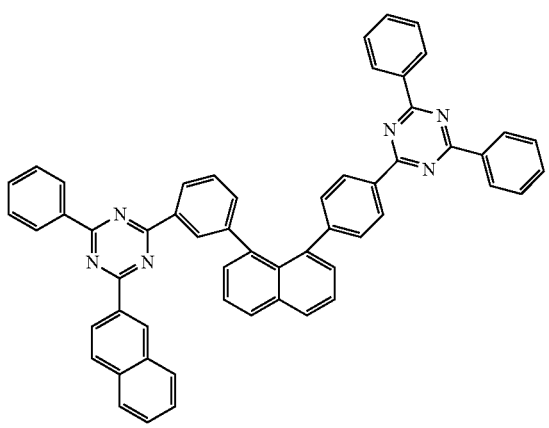
Chemical Formula 4-a-11
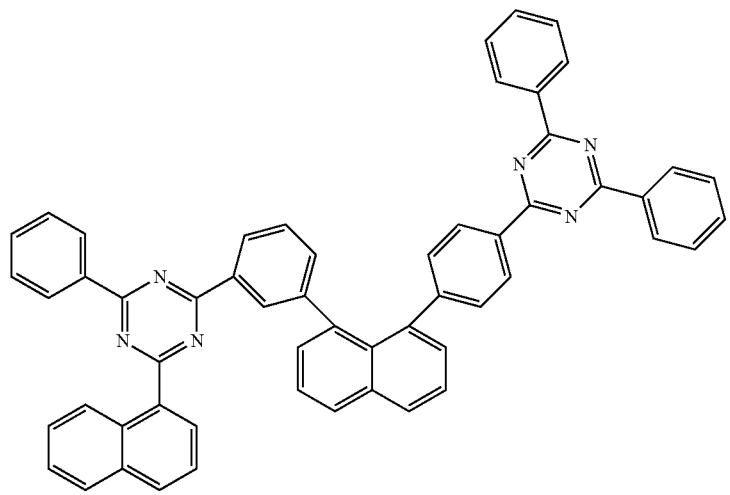

Chemical Formula 4-a-12
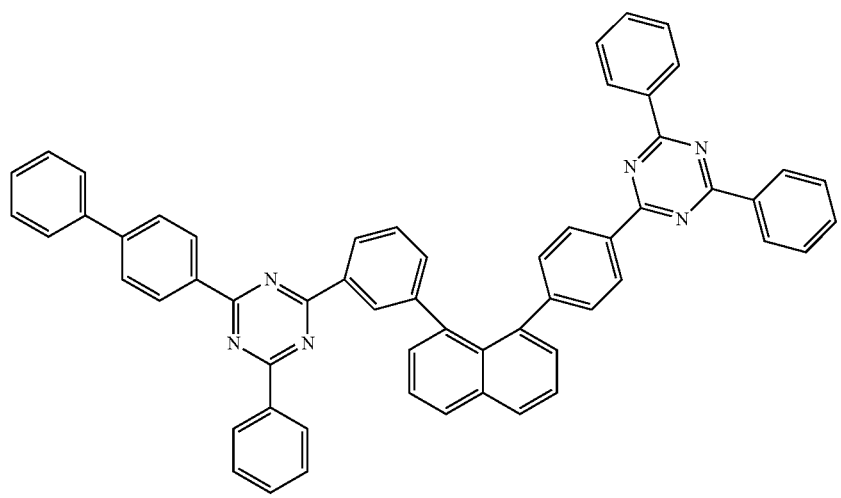
Chemical Formula 4-a-13
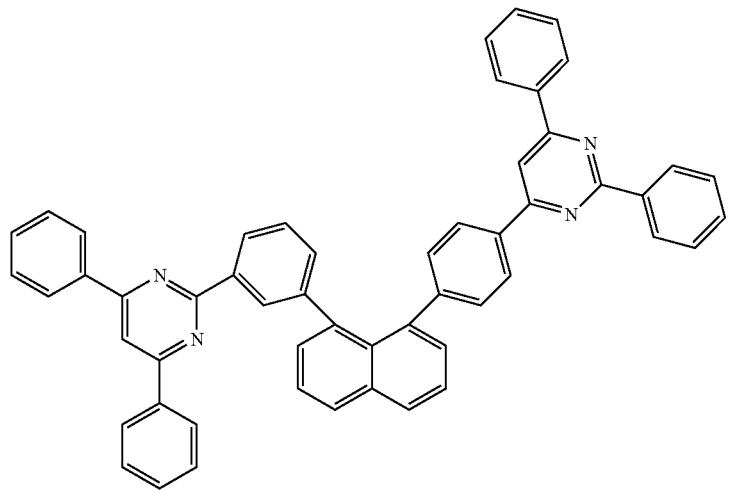
Chemical Formula 4-a-14
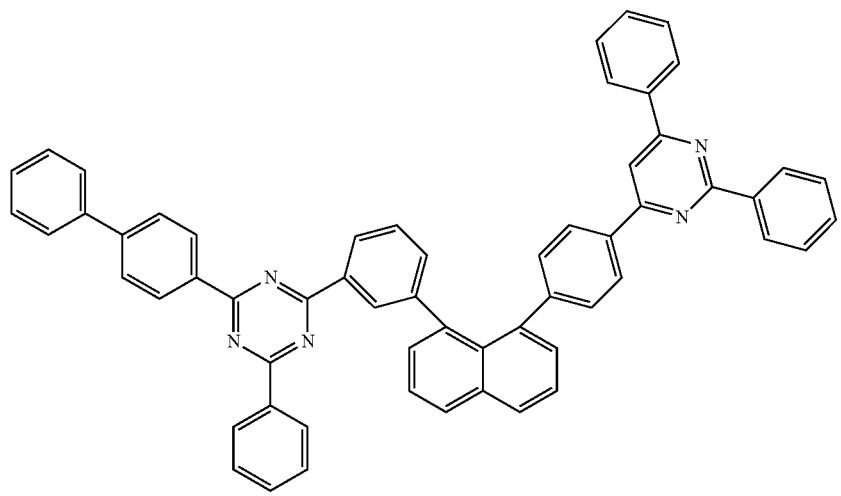

8. The hetero-cyclic compound of claim 1, wherein the compound represented by Chemical Formula 1 is represented by any one of the following Chemical Formulae 1-b-1 to 1-b-26, 2-b-1 to 2-b-26, 3-b-1 to 3-b-26, and 4-b-1 to 4-b-26:
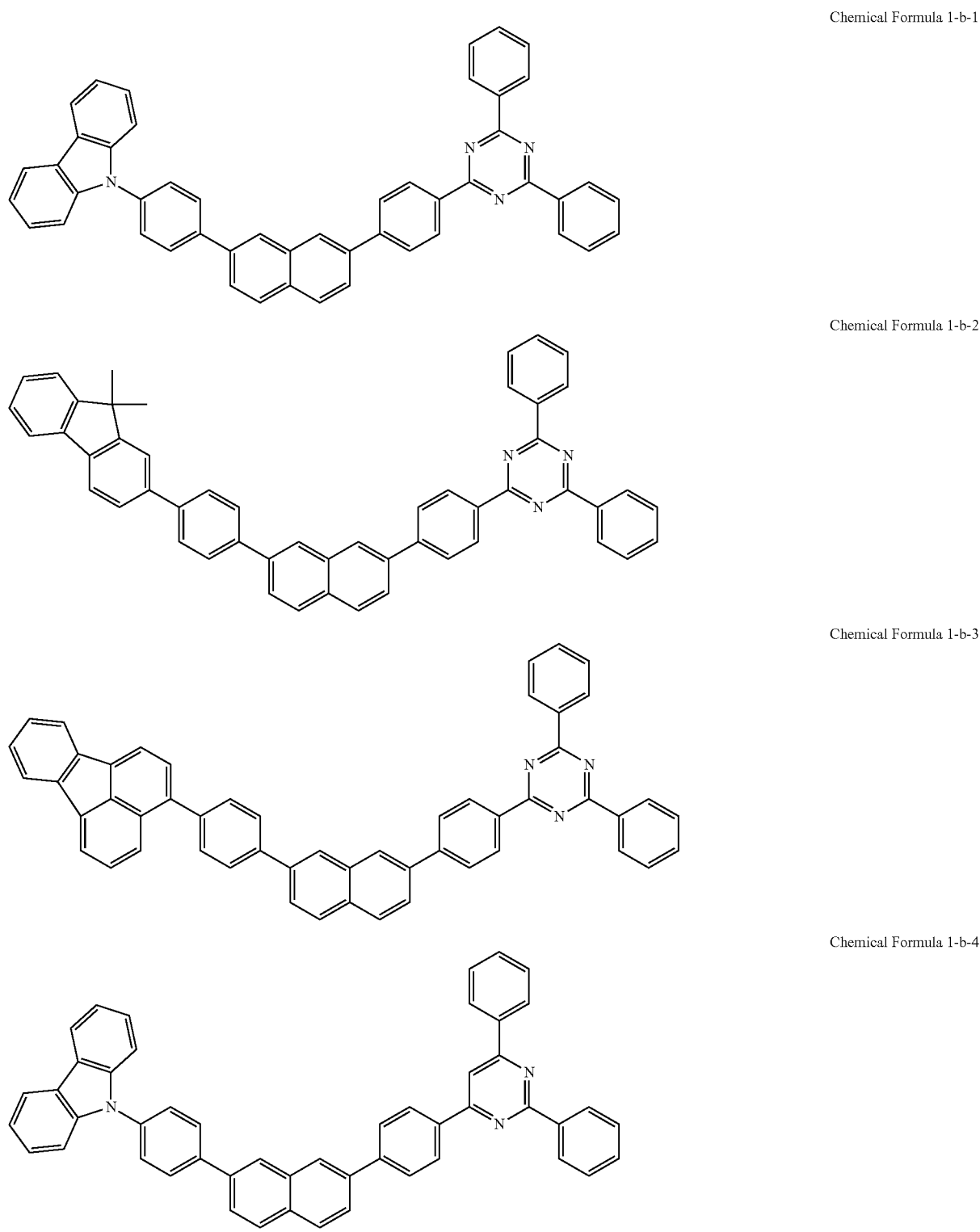
Chemical Formula 1-b-1
Chemical Formula 1-b-2
Chemical Formula 1-b-3
Chemical Formula 1-b-4

Chemical Formula 1-b-5
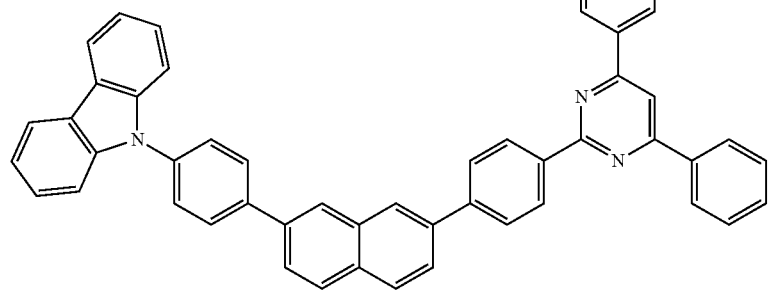
Chemical Formula 1-b-6
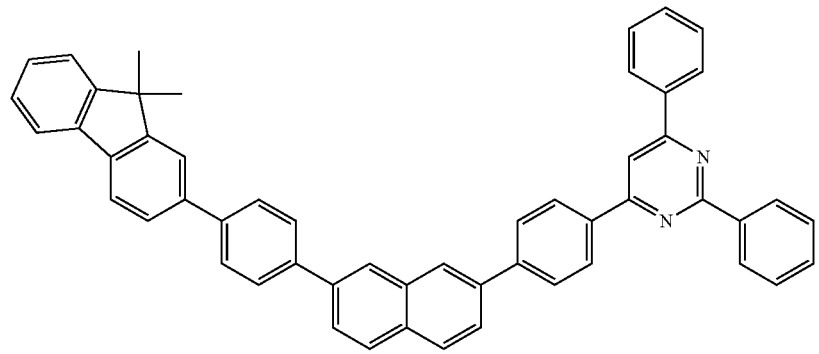
Chemical Formula 1-b-7
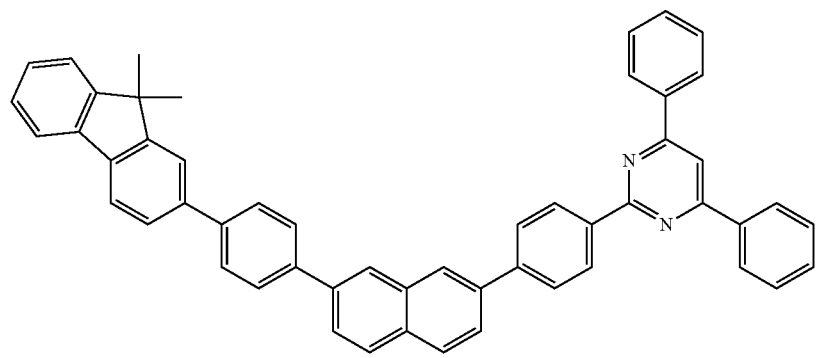
Chemical Formula 1-b-8
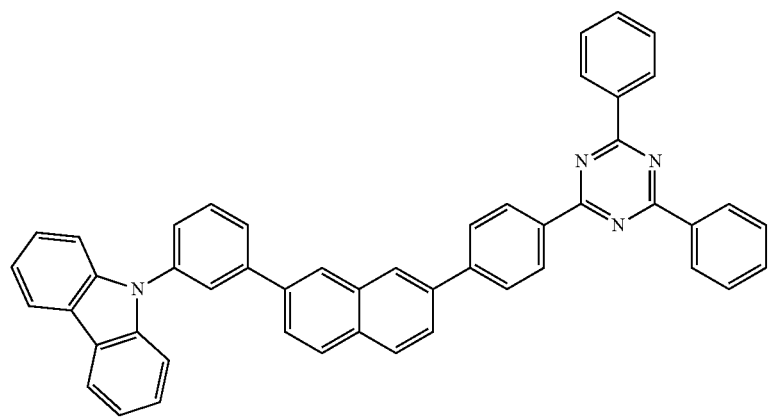

-continued
Chemical Formula 1-b-9
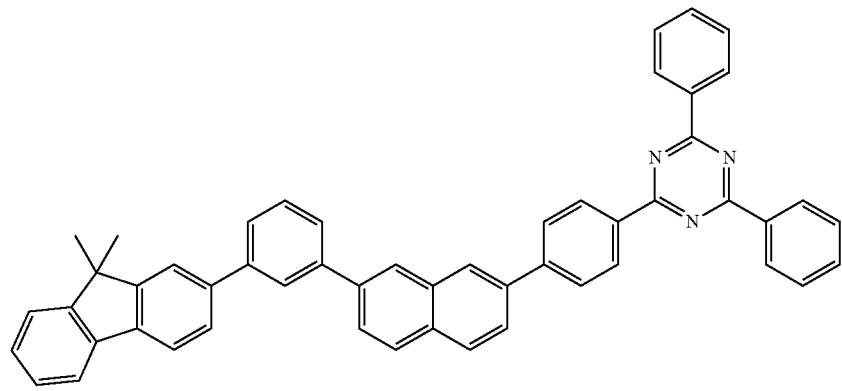
Chemical Formula 1-b-10
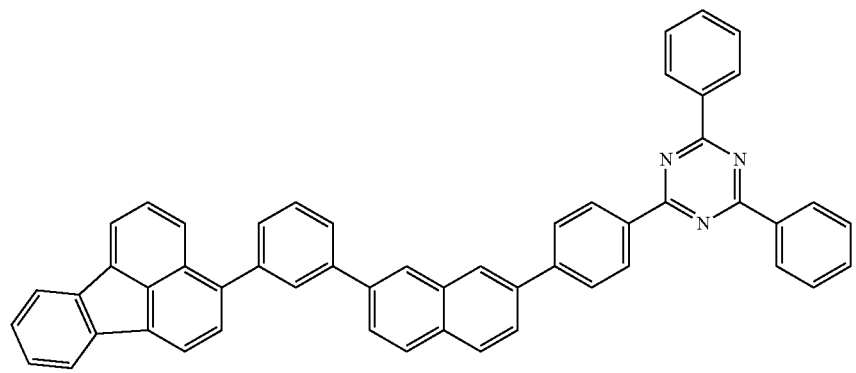
Chemical Formula 1-b-11
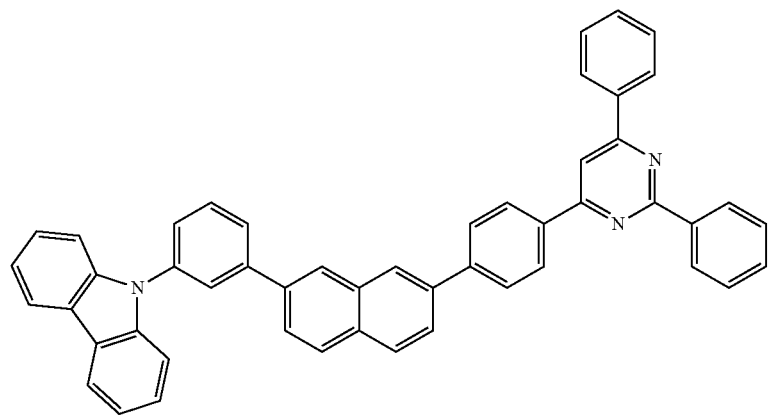
Chemical Formula 1-b-12
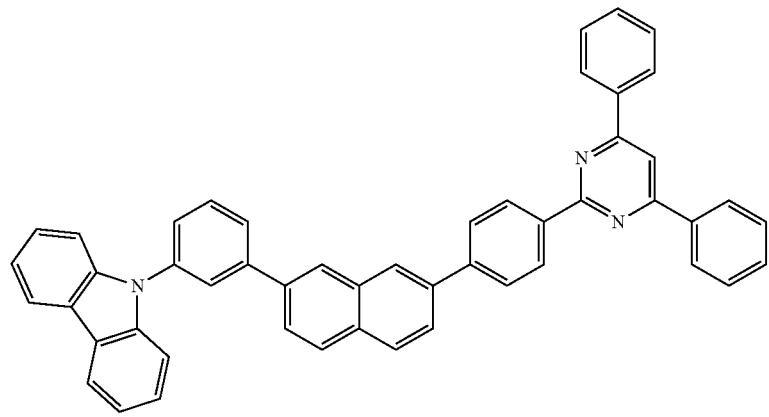

Chemical Formula 1-b-13
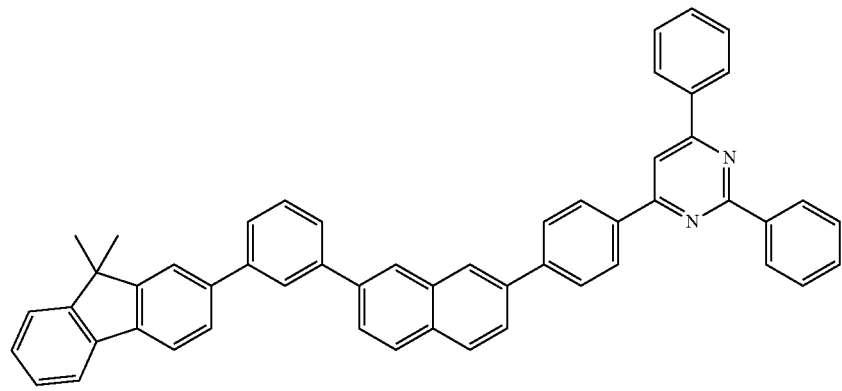
Chemical Formula 1-b-14
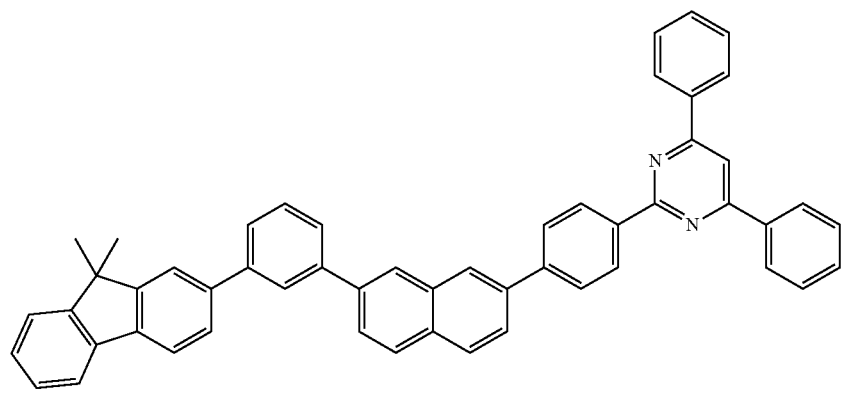
Chemical Formula 1-b-15
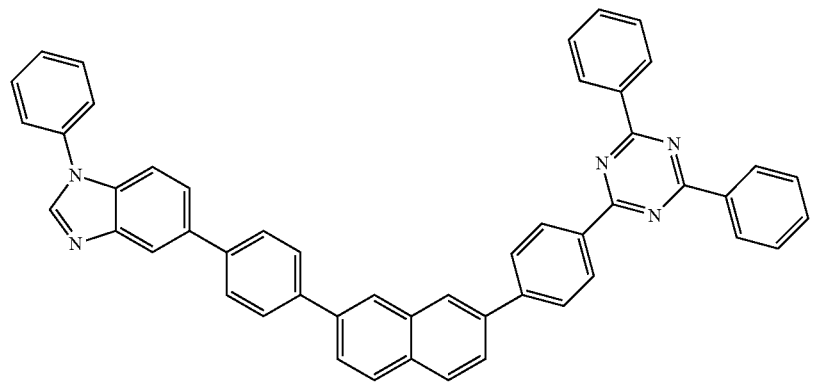
Chemical Formula 1-b-16
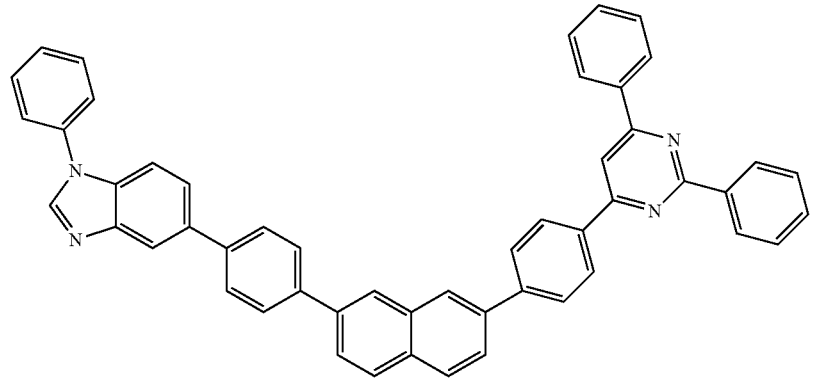

Chemical Formula 1-b-17
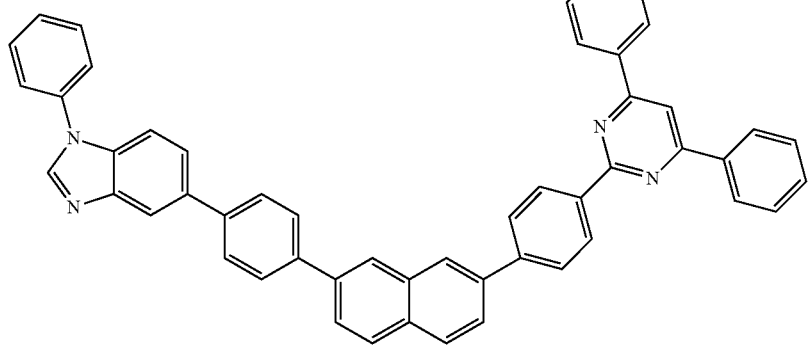
Chemical Formula 1-b-18
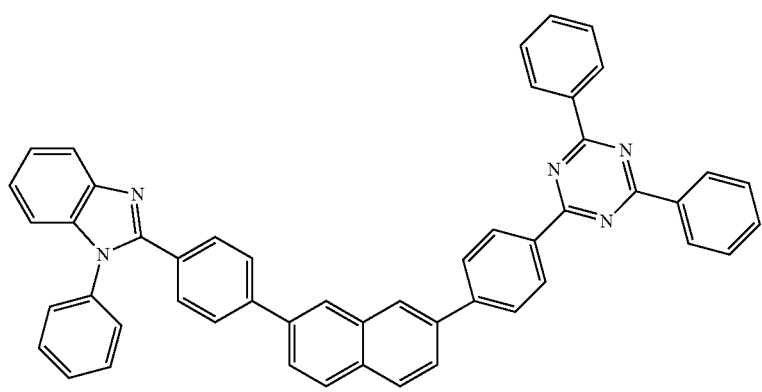
Chemical Formula 1-b-19
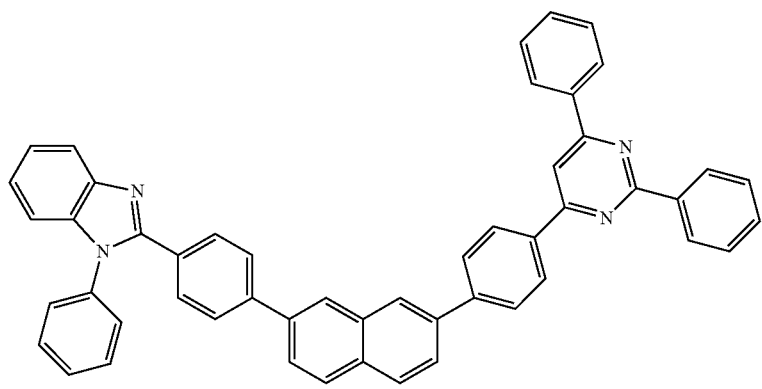
Chemical Formula 1-b-20
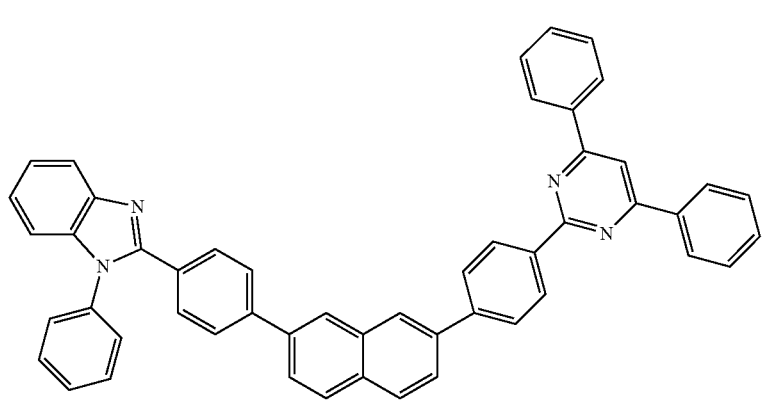

-continued
Chemical Formula 1-b-21
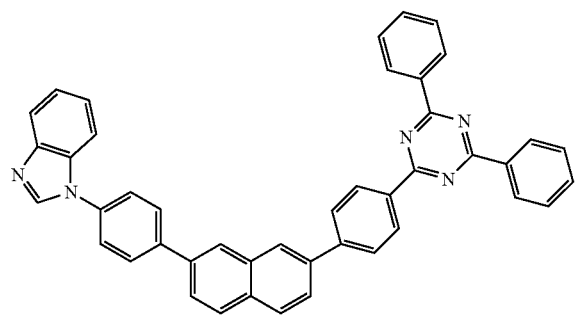
Chemical Formula 1-b-22
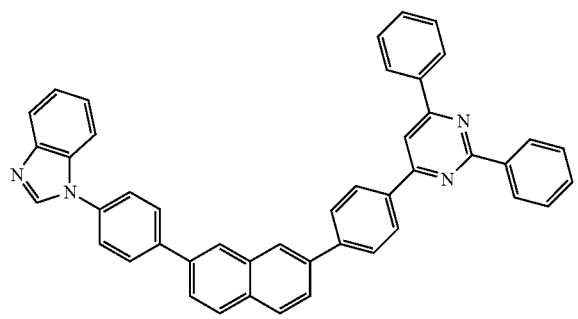
Chemical Formula 1-b-23
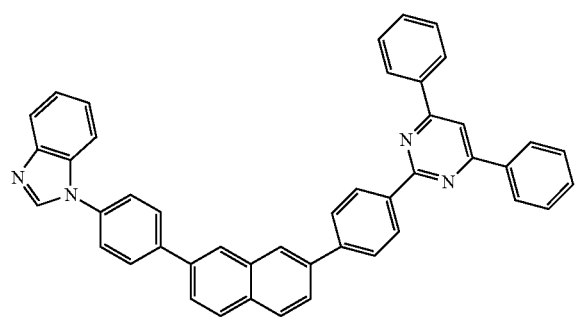
Chemical Formula 1-b-24
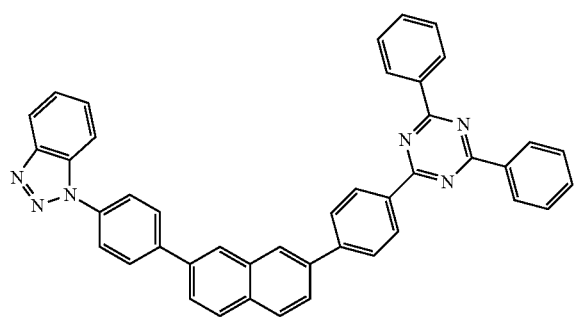
Chemical Formula 1-b-25
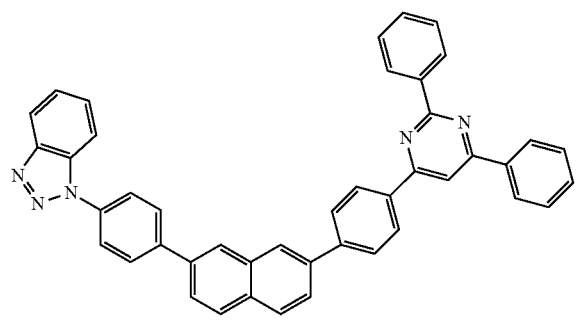
Chemical Formula 1-b-26
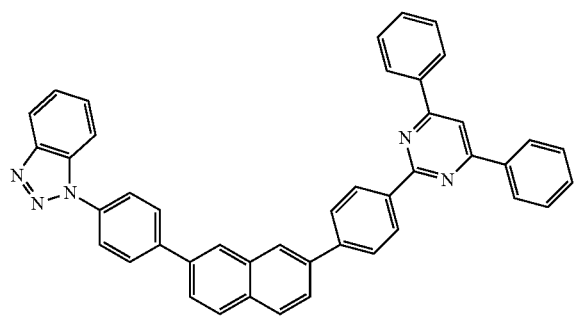
Chemical Formula 2-b-1
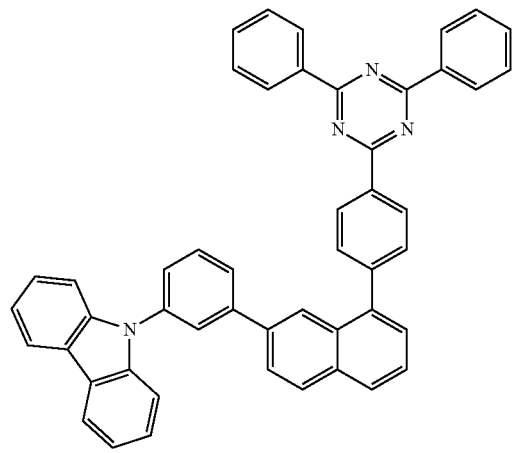
Chemical Formula 2-b-2
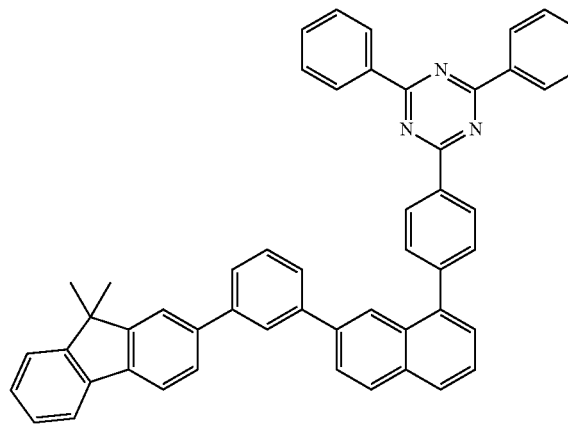

-continued
Chemical Formula 2-b-3
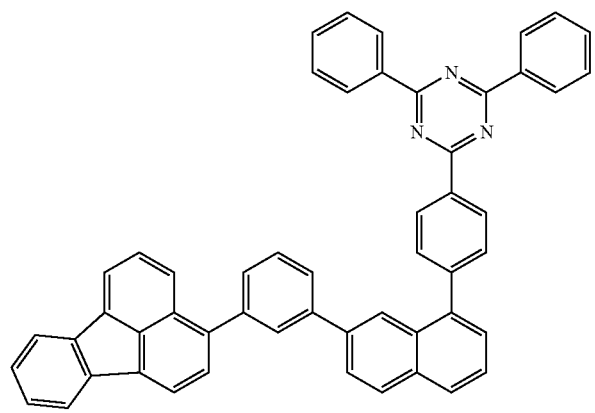
Chemical Formula 2-b-4
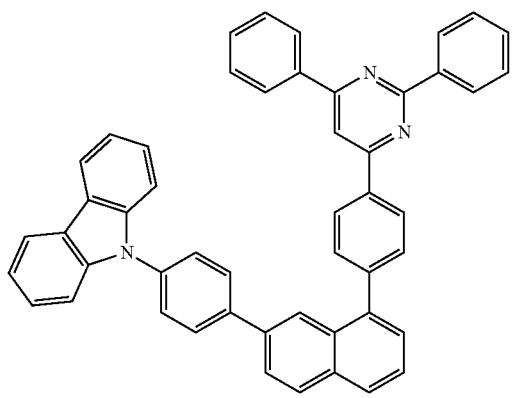
Chemical Formula 2-b-5
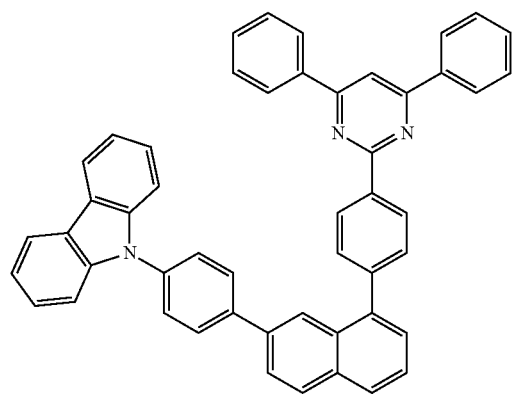
Chemical Formula 2-b-6
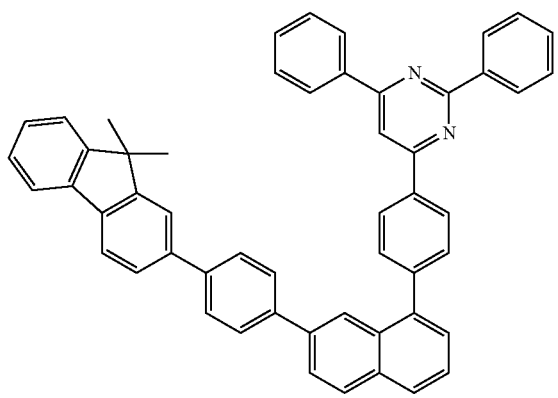
Chemical Formula 2-b-7
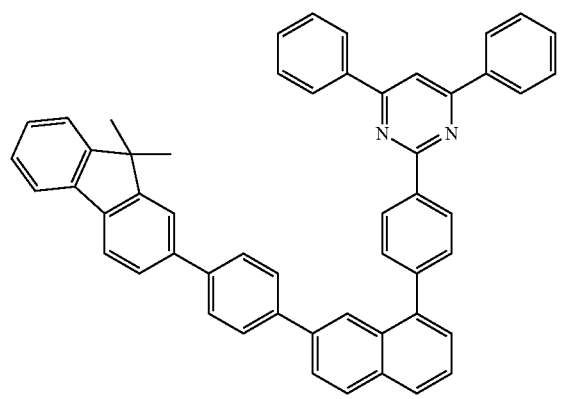
Chemical Formula 2-b-8
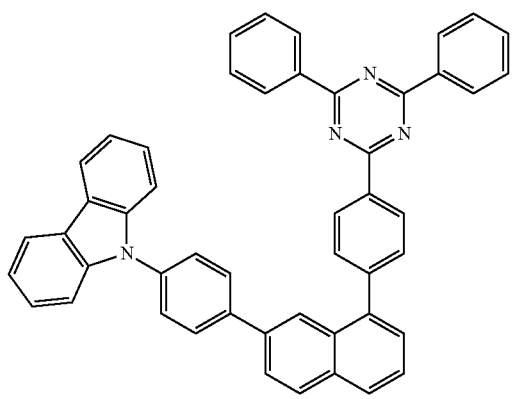

-continued
Chemical Formula 2-b-9
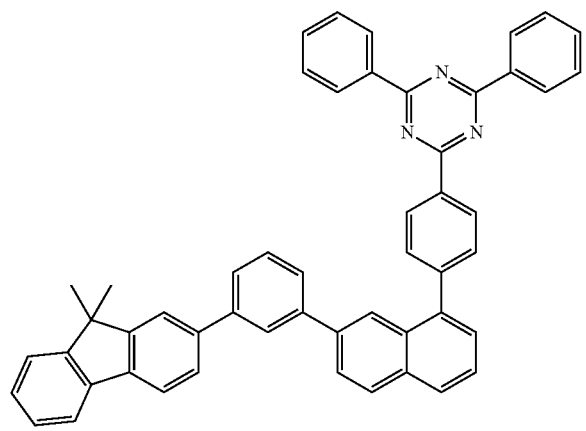
Chemical Formula 2-b-10
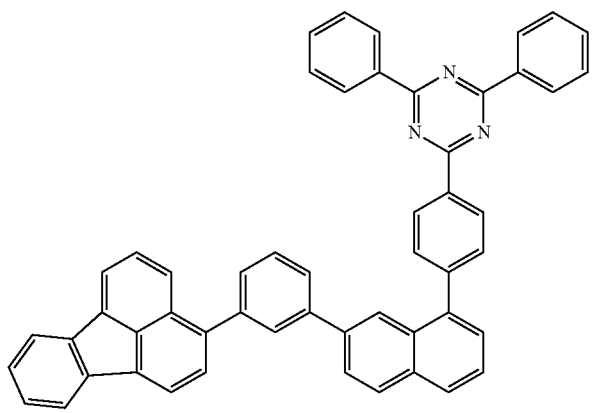
Chemical Formula 2-b-11
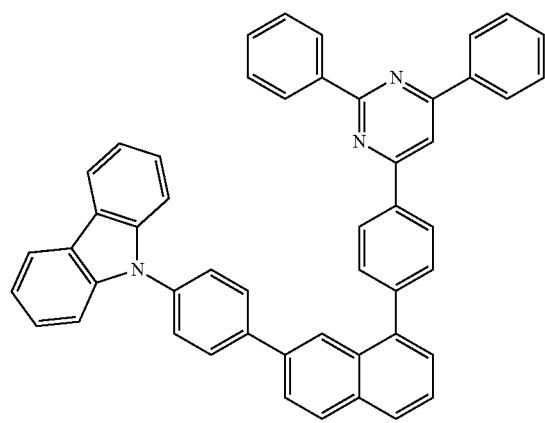
Chemical Formula 2-b-12
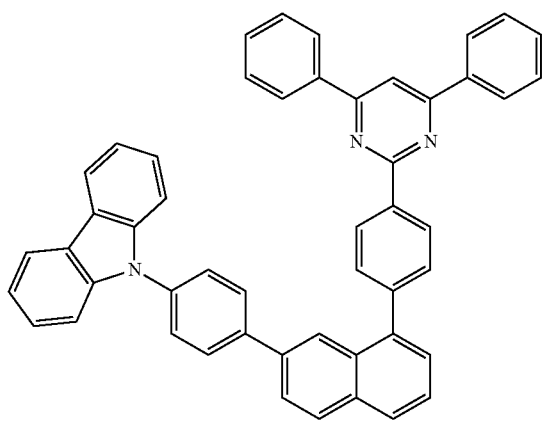
Chemical Formula 2-b-13
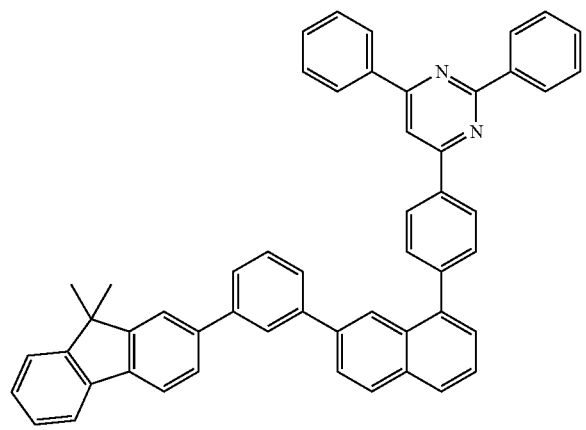
Chemical Formula 2-b-14
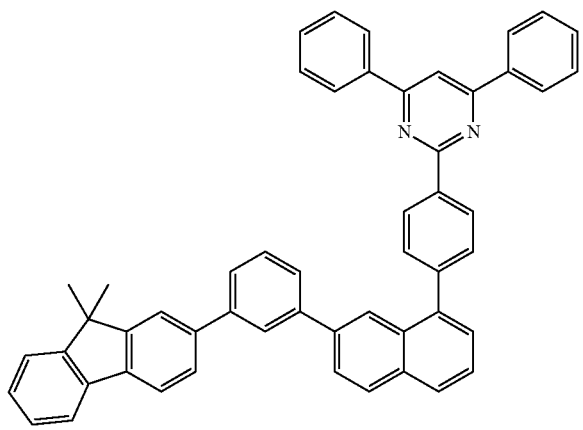

-continued
Chemical Formula 2-b-15
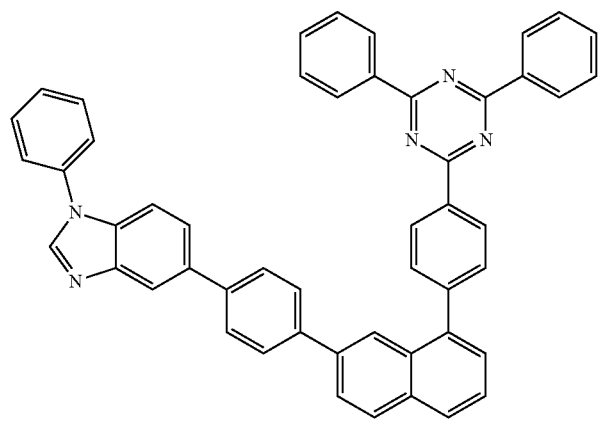
Chemical Formula 2-b-16
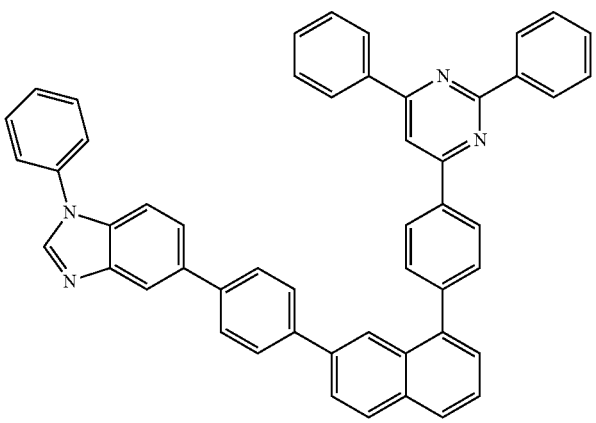
Chemical Formula 2-b-17
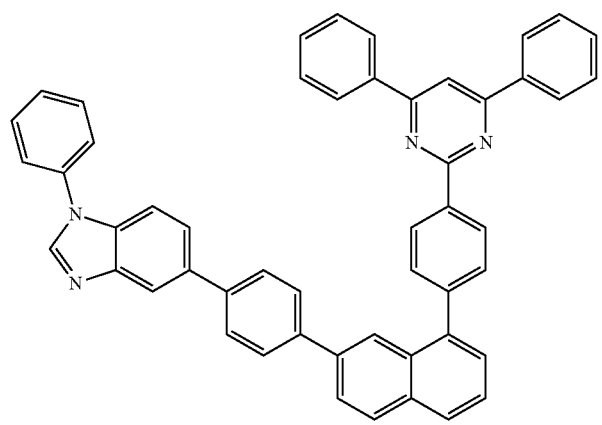
Chemical Formula 2-b-18
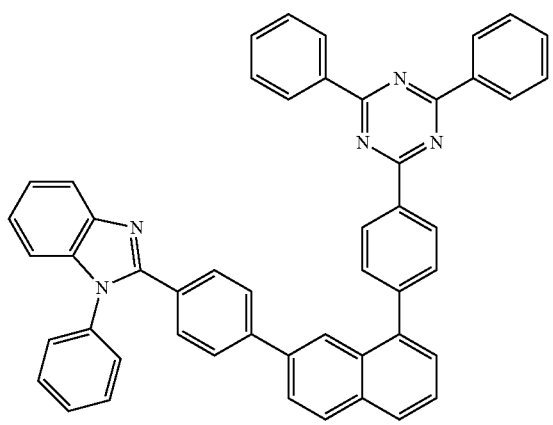
Chemical Formula 2-b-19
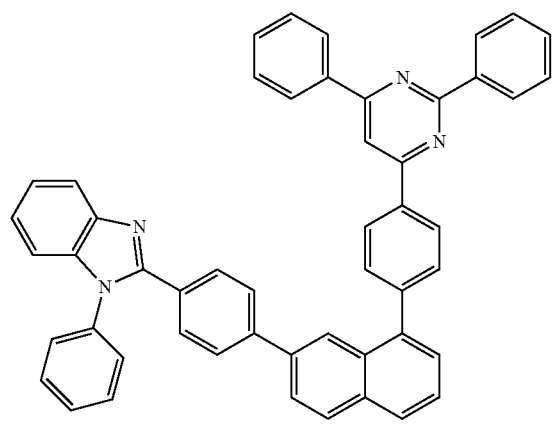
Chemical Formula 2-b-20
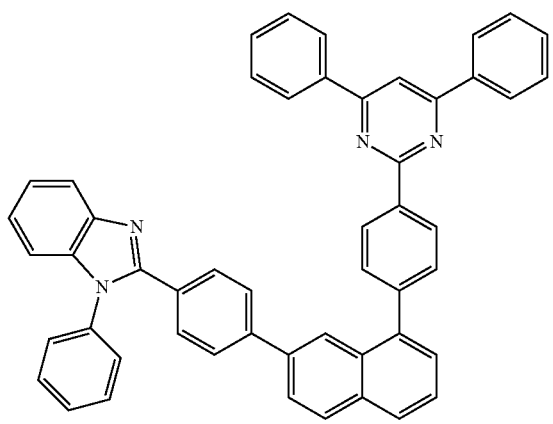

-continued
Chemical Formula 2-b-21
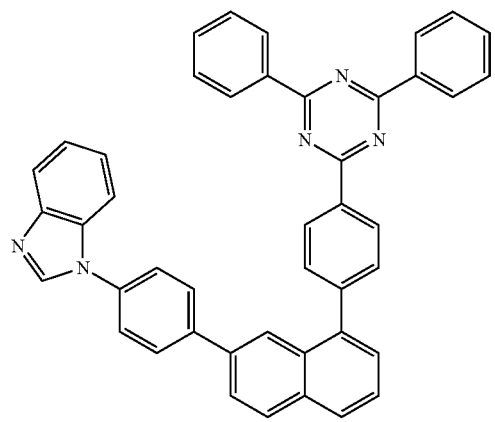
Chemical Formula 2-b-22
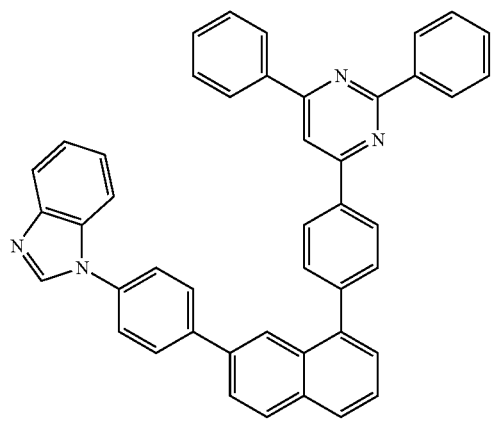
Chemical Formula 2-b-23
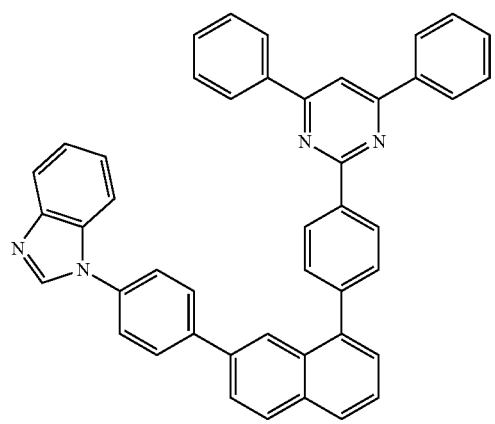
Chemical Formula 2-b-24
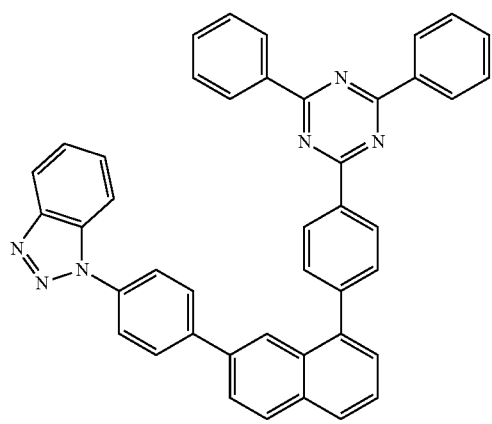
Chemical Formula 2-b-25
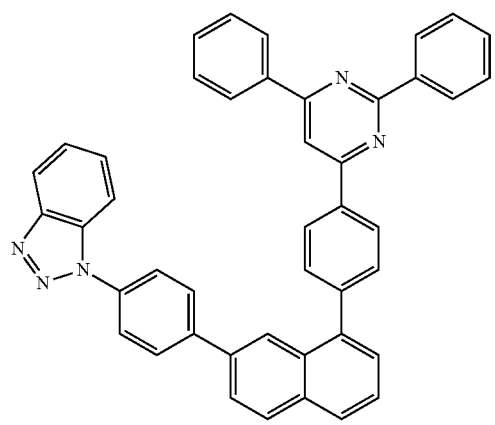
Chemical Formula 2-b-26
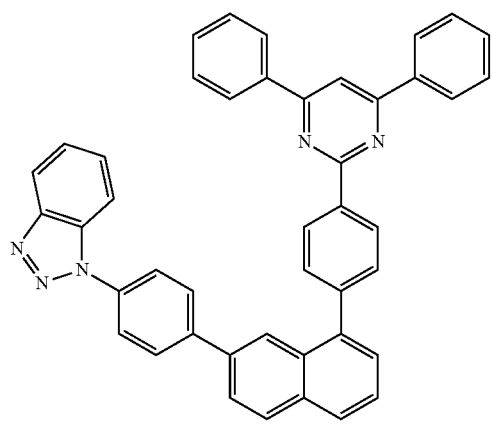

-continued
Chemical Formula 3-b-1
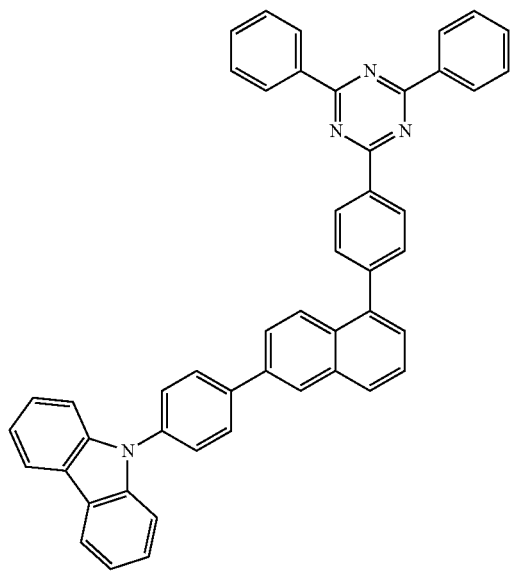
Chemical Formula 3-b-2
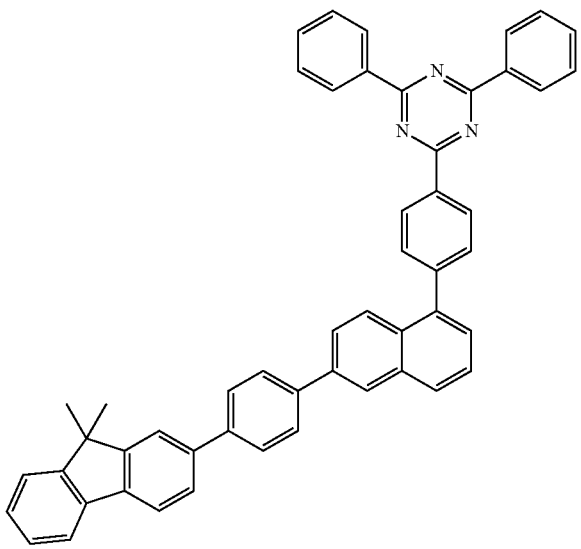
Chemical Formula 3-b-3
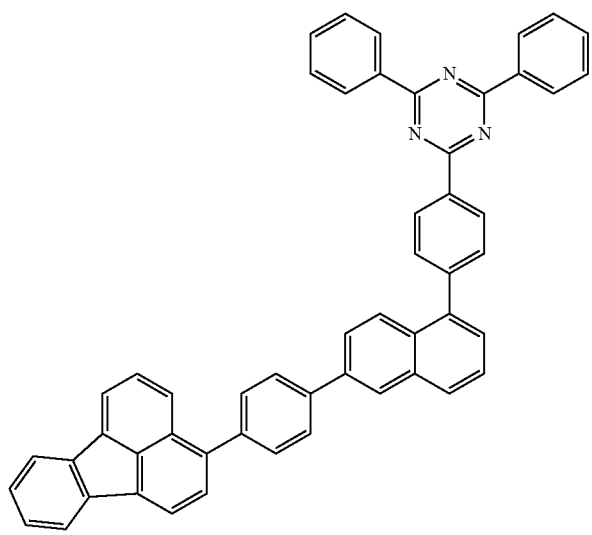
Chemical Formula 3-b-4
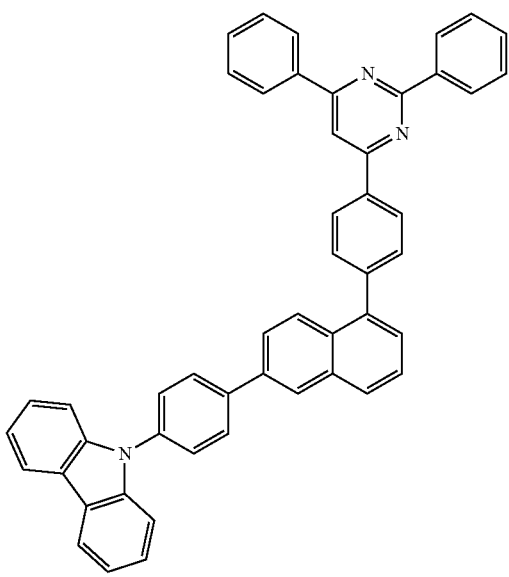

-continued
Chemical Formula 3-b-5
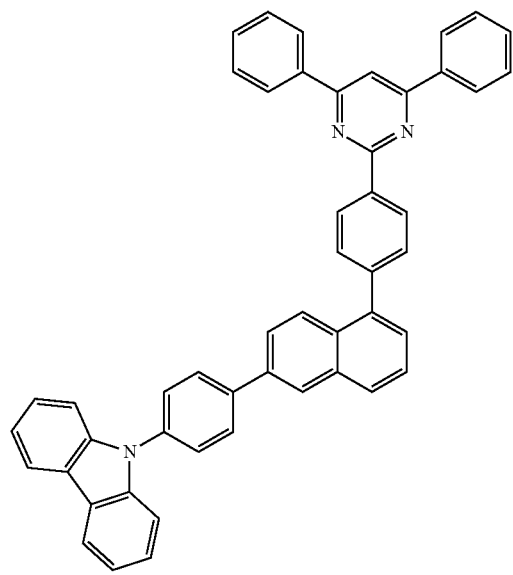
Chemical Formula 3-b-6
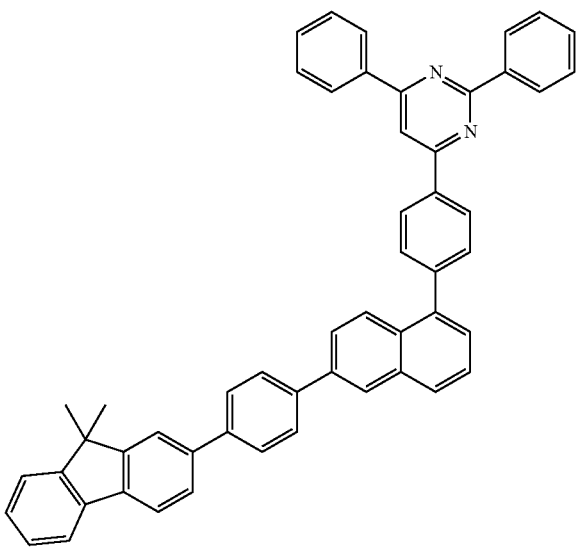
Chemical Formula 3-b-7
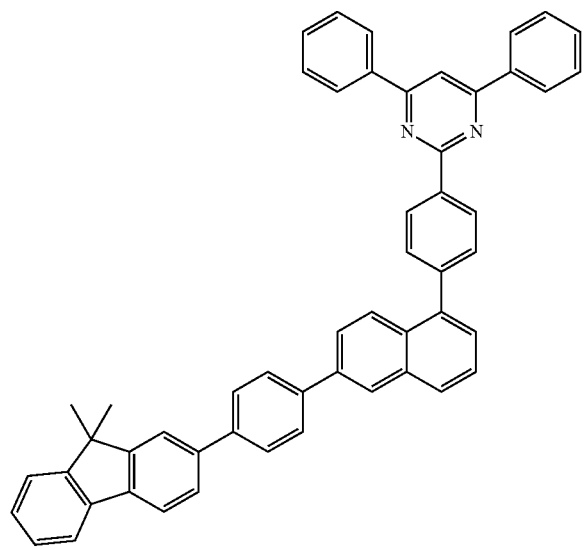
Chemical Formula 3-b-8
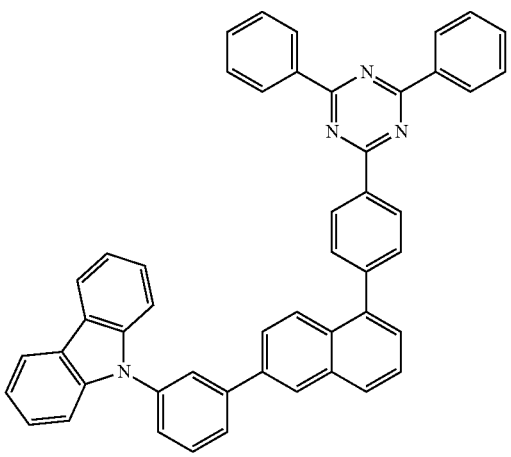
Chemical Formula 3-b-9
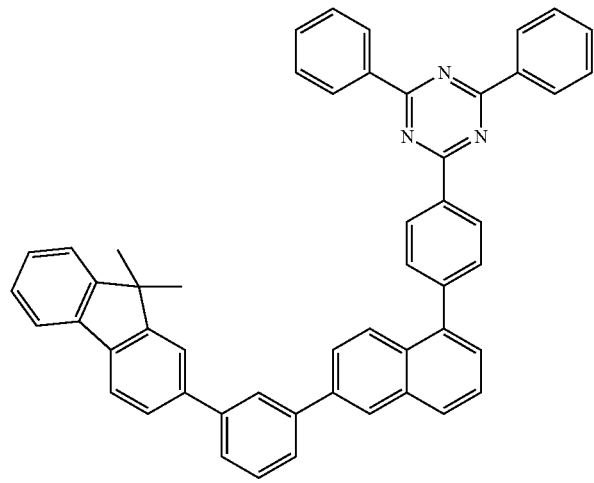
Chemical Formula 3-b-10
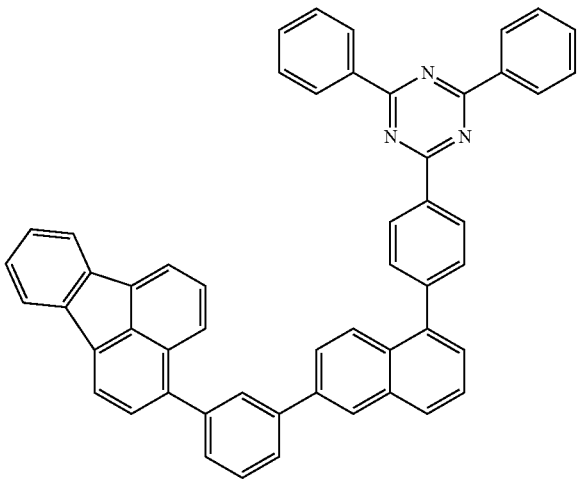

-continued
Chemical Formula 3-b-11
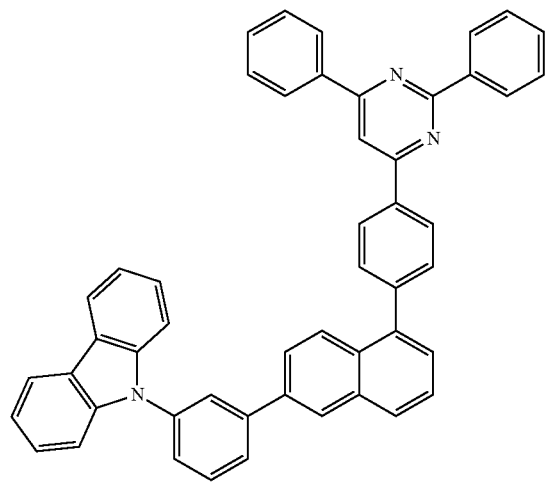
Chemical Formula 3-b-12
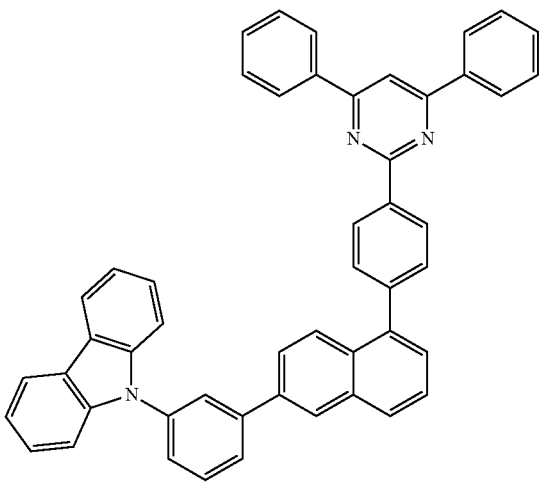
Chemical Formula 3-b-13
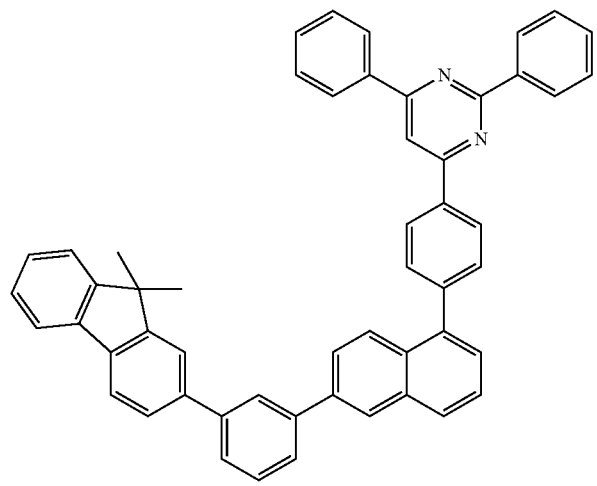
Chemical Formula 3-b-14
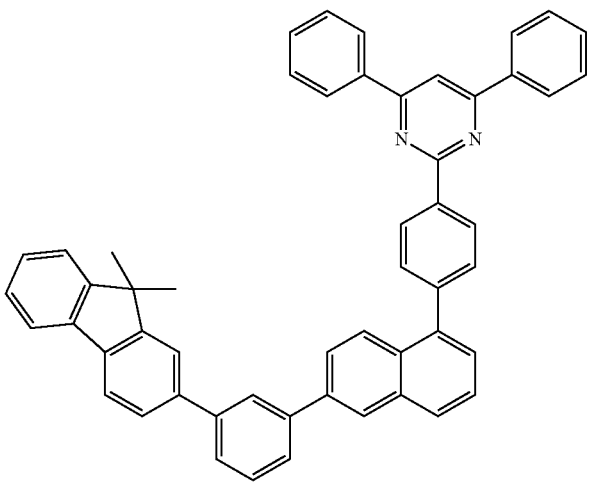
Chemical Formula 3-b-15
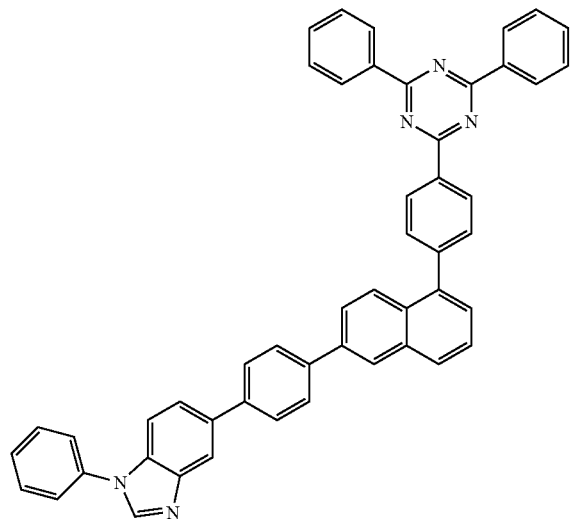
Chemical Formula 3-b-16
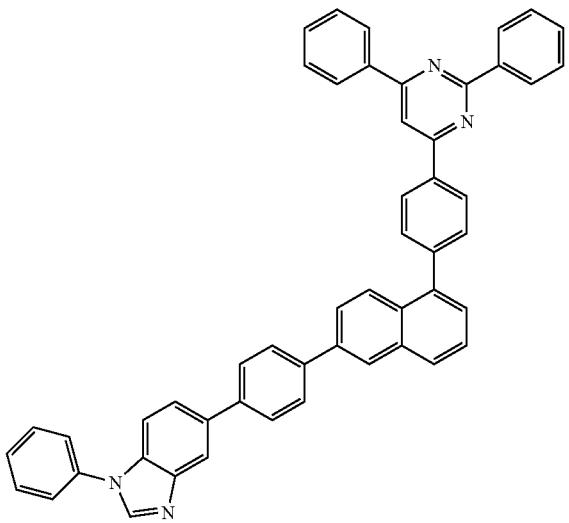

-continued
Chemical Formula 3-b-17
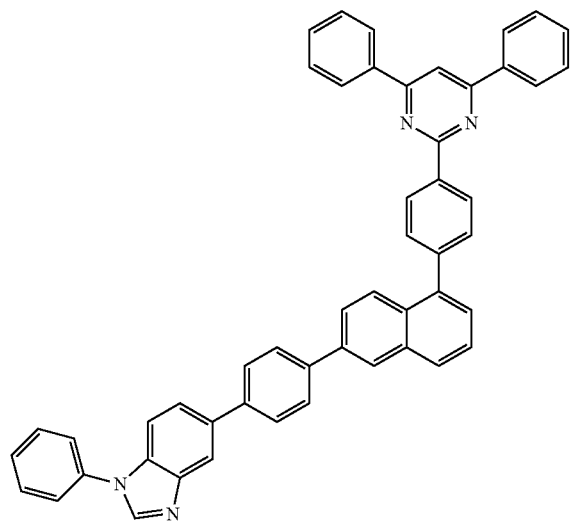
Chemical Formula 3-b-18
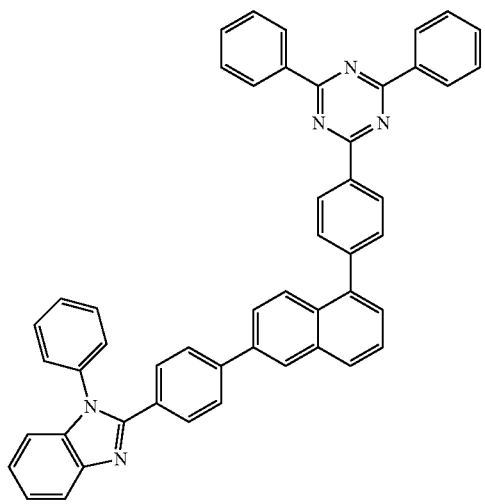
Chemical Formula 3-b-19
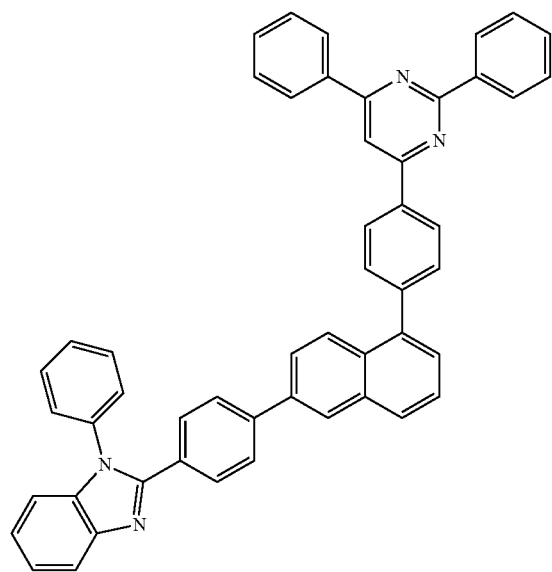
Chemical Formula 3-b-20
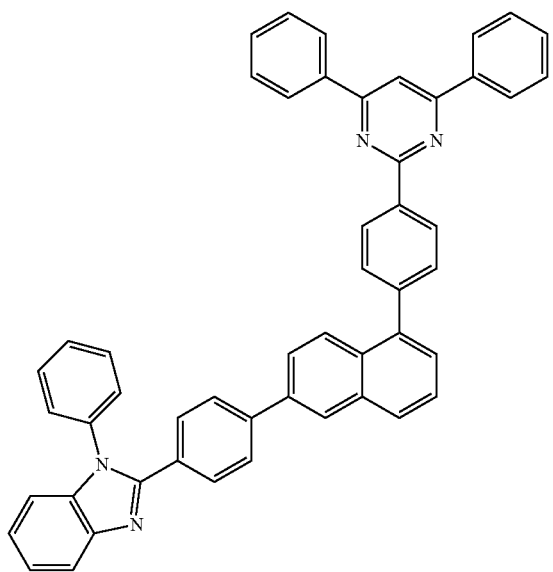

Chemical Formula 3-b-21
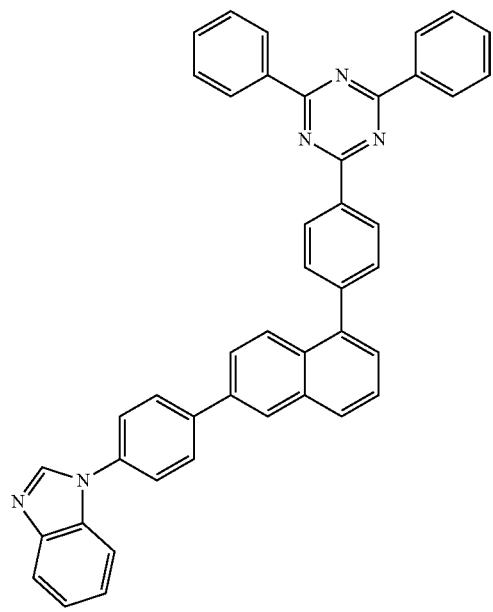
Chemical Formula 3-b-22
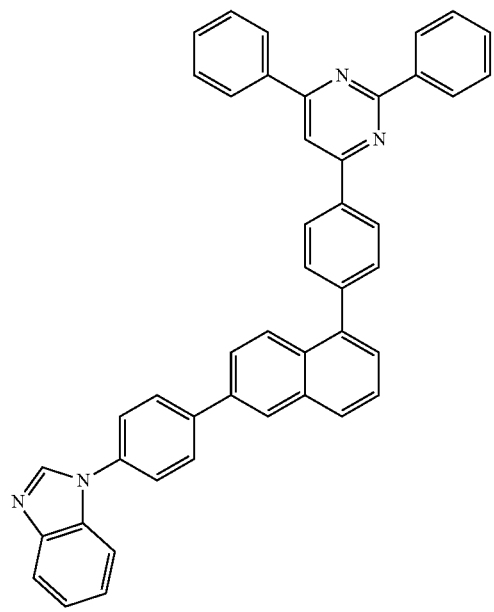
Chemical Formula 3-b-23
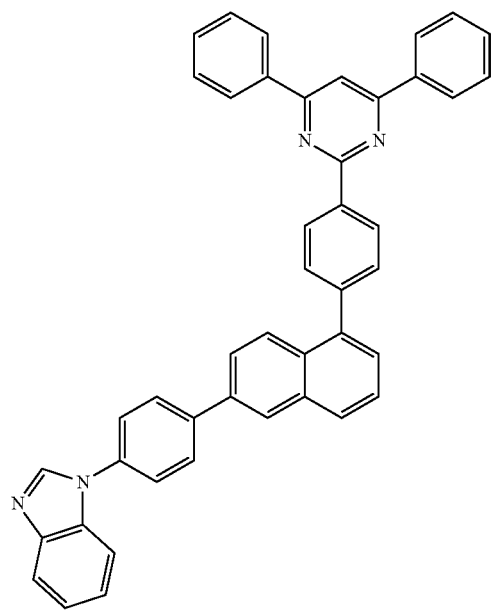
Chemical Formula 3-b-24
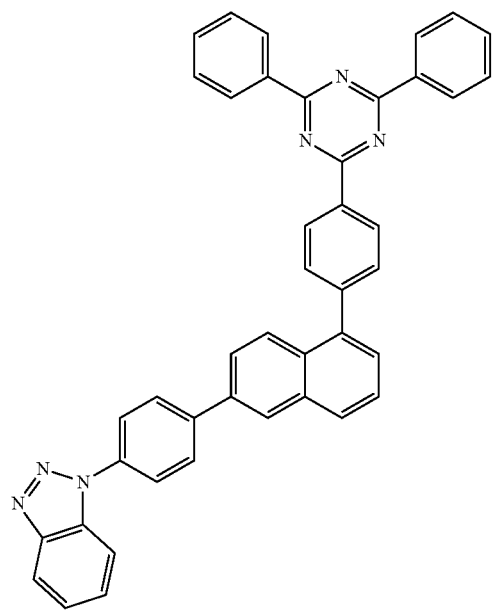

-continued
Chemical Formula 3-b-25
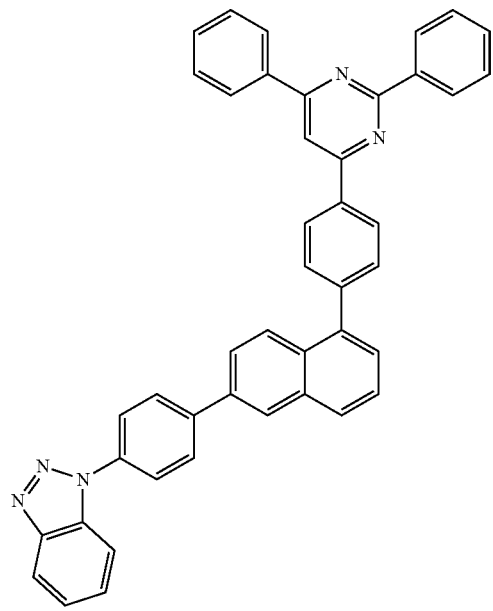
Chemical Formula 3-b-26
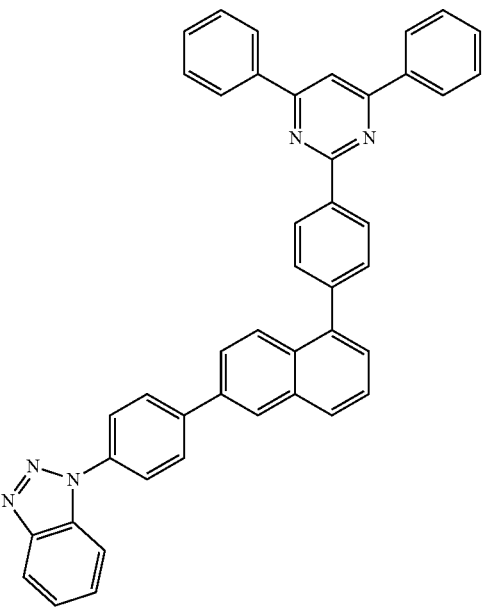
Chemical Formula 4-b-1
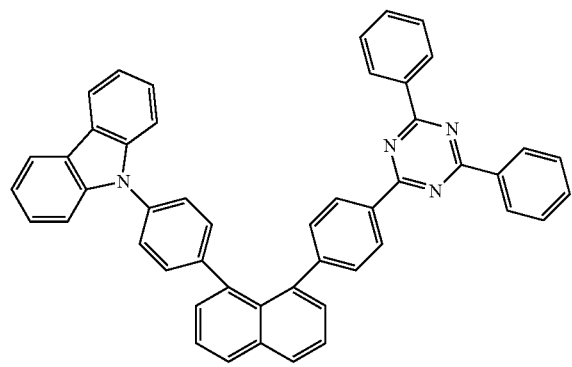
Chemical Formula 4-b-2
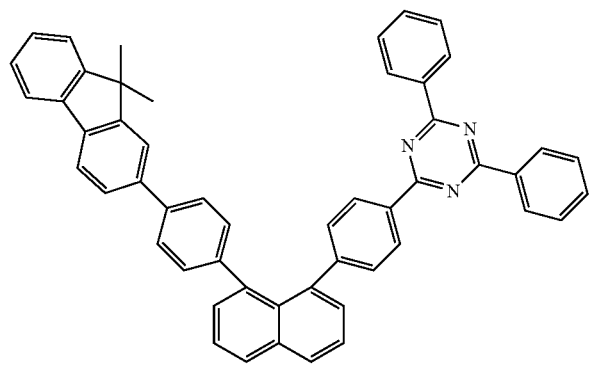
Chemical Formula 4-b-3
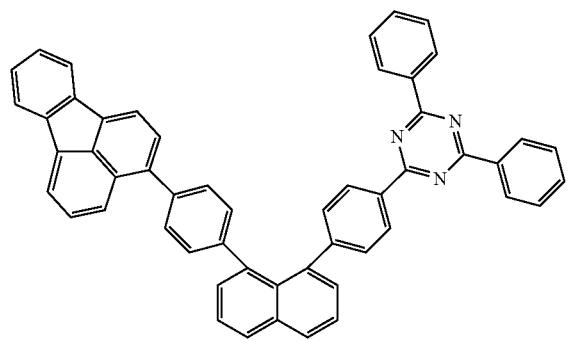
Chemical Formula 4-b-4
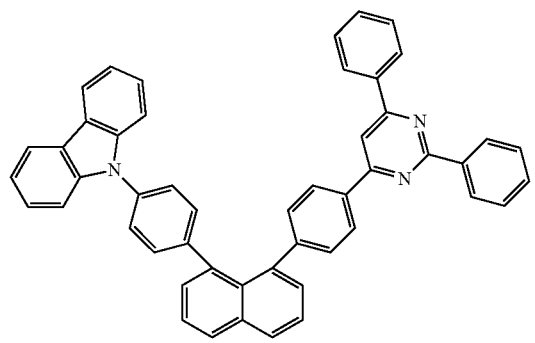

-continued
Chemical Formula 4-b-5
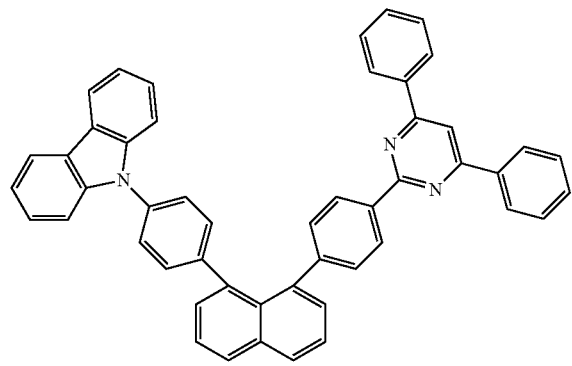
Chemical Formula 4-b-6
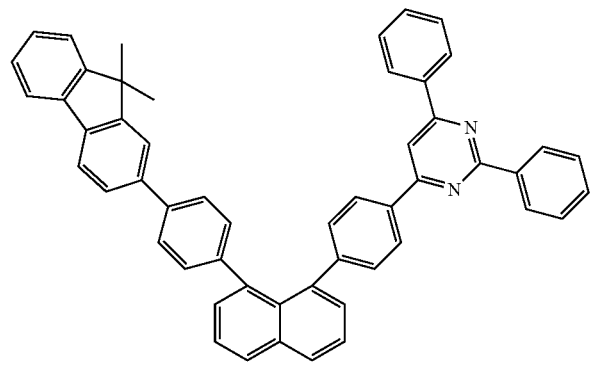
Chemical Formula 4-b-7
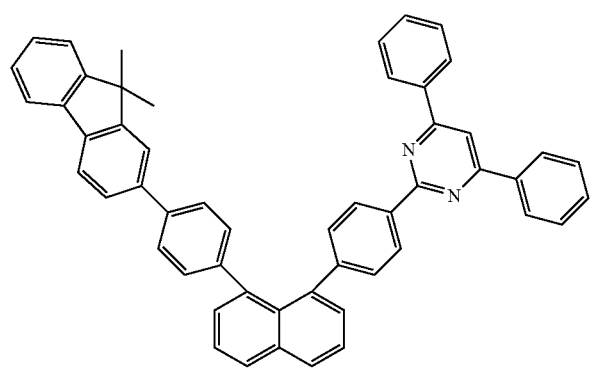
Chemical Formula 4-b-8
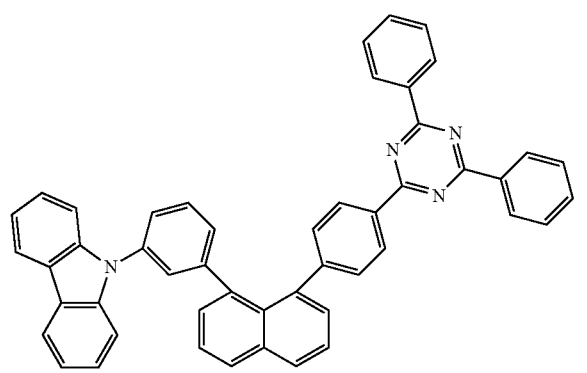
Chemical Formula 4-b-9
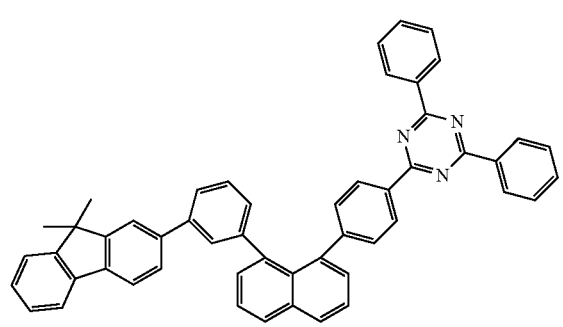
Chemical Formula 4-b-10
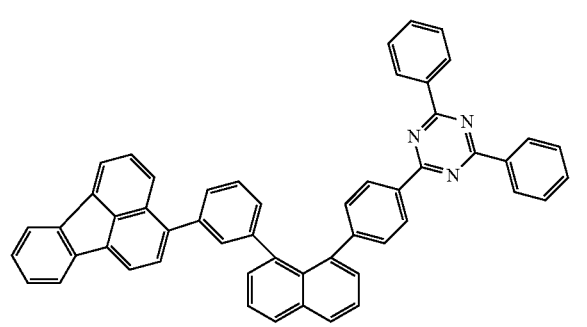
Chemical Formula 4-b-11
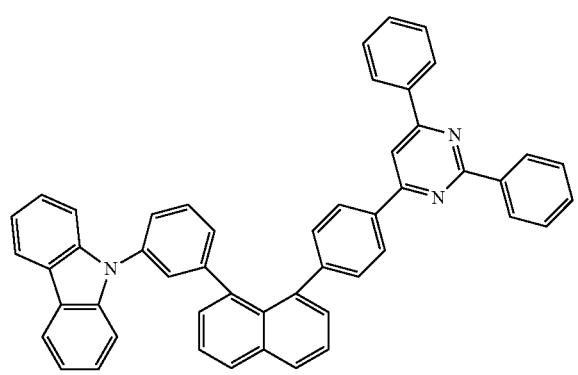
Chemical Formula 4-b-12
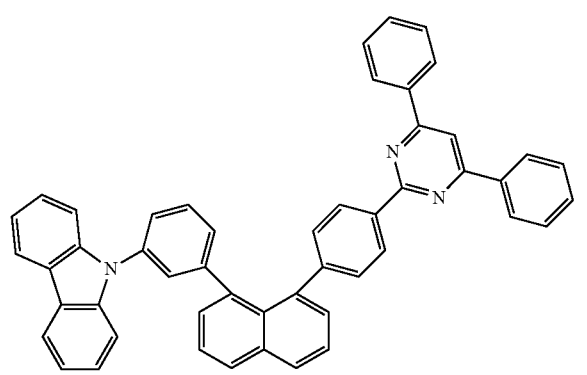

-continued
Chemical Formula 4-b-13
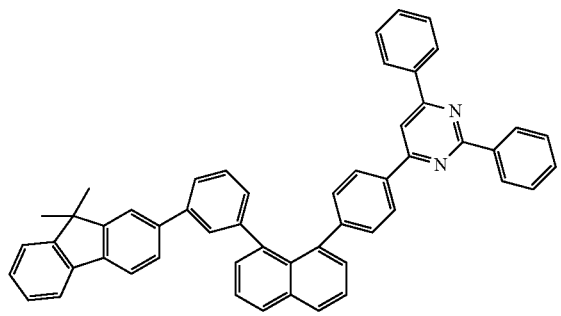
Chemical Formula 4-b-14
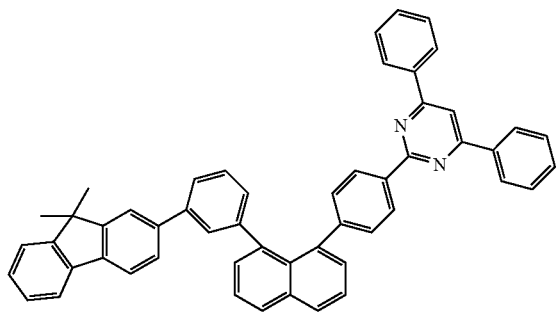
Chemical Formula 4-b-15
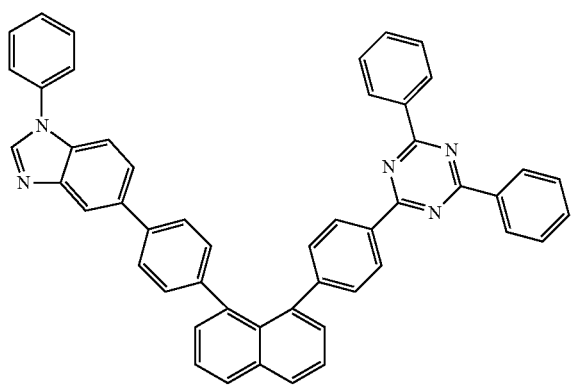
Chemical Formula 4-b-16
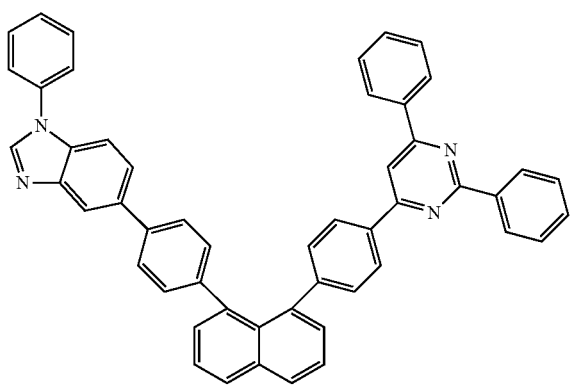
Chemical Formula 4-b-17
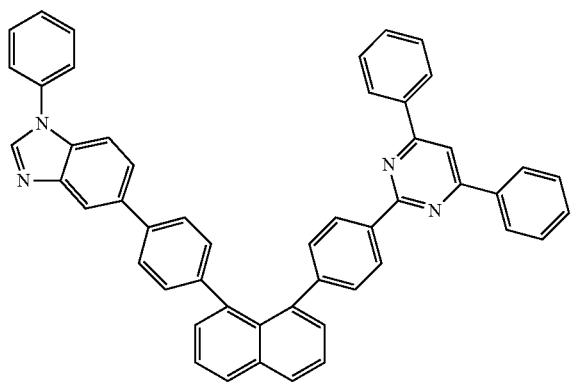
Chemical Formula 4-b-18
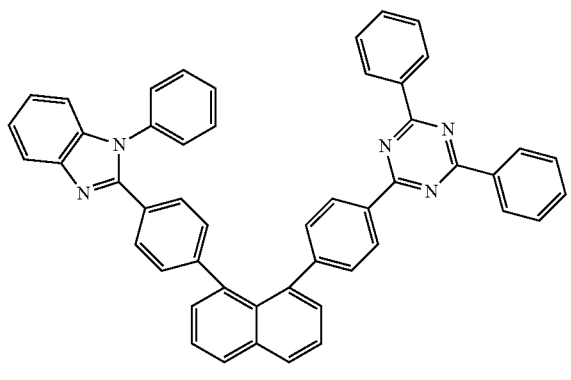
Chemical Formula 4-b-19
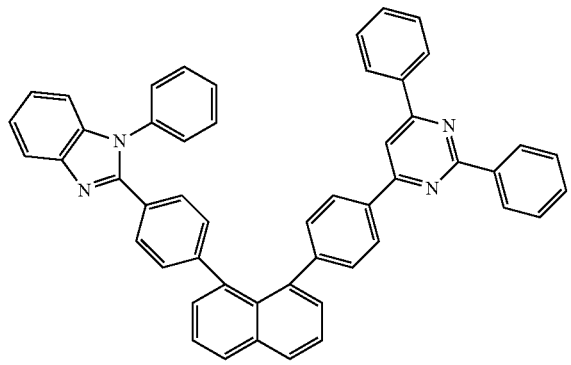
Chemical Formula 4-b-20
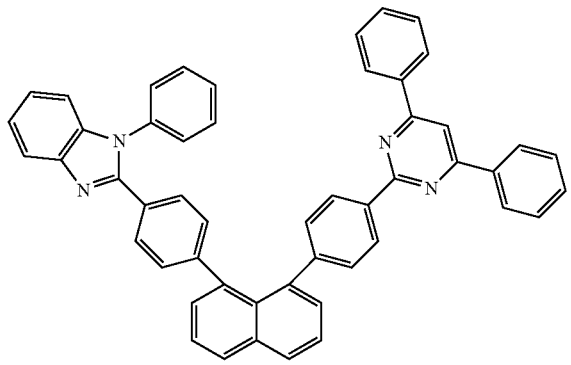

-continued

Chemical Formula 4-b-21

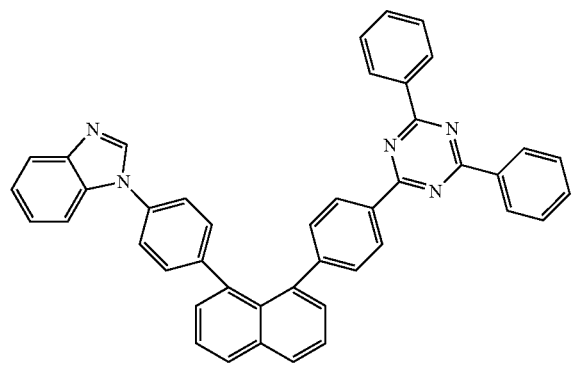

Chemical Formula 4-b-22

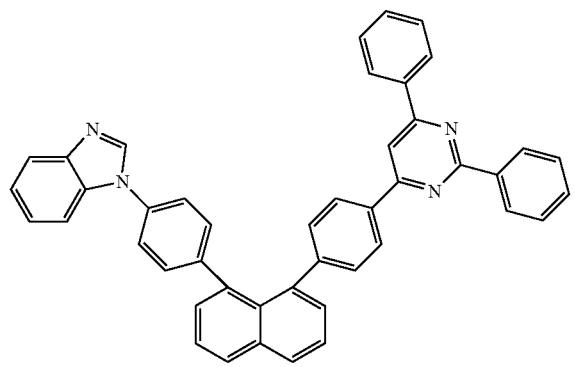

Chemical Formula 4-b-23

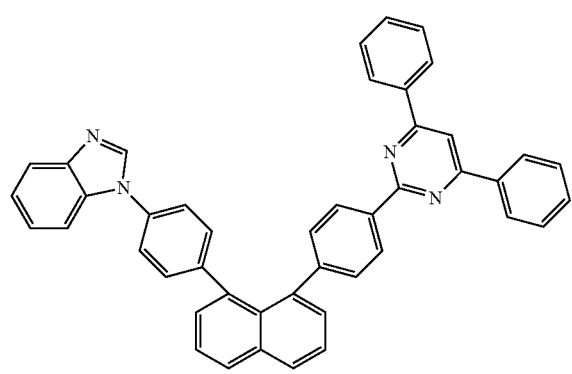

Chemical Formula 4-b-24

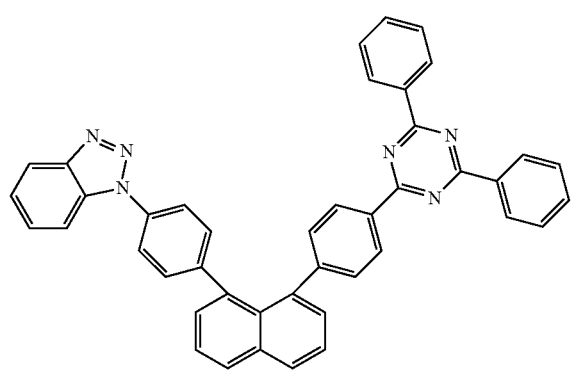

Chemical Formula 4-b-25

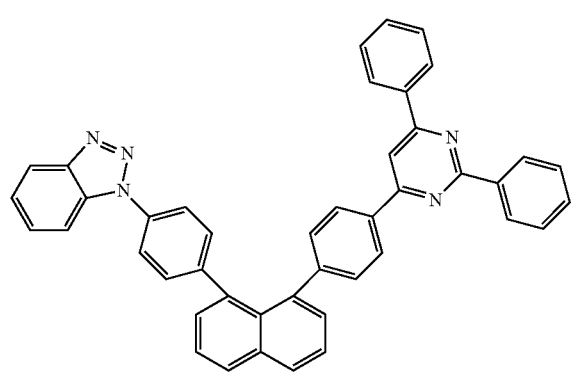

Chemical Formula 4-b-26

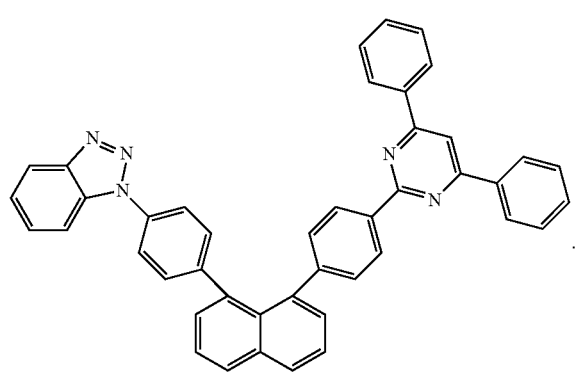

9. An organic light emitting device comprising:
a first electrode;
a second electrode provided opposite to the first electrode; and
an organic material layer having one or more layers provided between the first electrode and the second electrode,
wherein the one or more layers of the organic material layer include the hetero-cyclic compound according to claim 1.

10. The organic light emitting device of claim 9, wherein the organic material layer includes a hole injection layer or a hole transfer layer; and
the hole injection layer or the hole transfer layer includes the hetero-cyclic compound.

11. The organic light emitting device of claim 9, wherein the organic material layer includes a light emitting layer; and the light emitting layer includes the hetero-cyclic compound as a host of the light emitting layer.

12. The organic light emitting device of claim 9, wherein the organic material layer includes an electron transfer layer or an electron injection layer; and
the electron transfer layer or the electron injection layer includes the hetero-cyclic compound.

13. The organic light emitting device of claim 9, wherein the organic material layer further includes a hole injection layer or a hole transfer layer including an arylamino group, a carbazole group or a benzocarbazole group, in addition to the organic material layer including the hetero-cyclic compound.

14. The organic light emitting device of claim 9, wherein the organic material layer including the hetero-cyclic compound includes the hetero-cyclic compound as a host, and other organic compounds, metals or metal compounds as a dopant.

* * * * *